United States Patent [19]
Traynor-Kaplan et al.

[11] Patent Number: 5,977,078
[45] Date of Patent: *Nov. 2, 1999

[54] INOSITOL POLYPHOSPHATE DERIVATIVES AND METHODS OF USING SAME

[75] Inventors: Alexis Traynor-Kaplan, North Bend, Wash.; Carsten Schultz; Stefan Roemer, both of Bremen, Germany; Christoph Stadler, Bremen; Marco Rudolf, Hemslingen, both of Germany

[73] Assignee: The Regents of the Univesity of California, Oakland, Calif.

[*] Notice: This patent is subject to a terminal disclaimer.

[21] Appl. No.: 08/934,450

[22] Filed: Sep. 19, 1997

Related U.S. Application Data

[63] Continuation-in-part of application No. 08/926,831, Sep. 10, 1997, Pat. No. 5,880,099
[60] Provisional application No. 60/077,178, Sep. 20, 1996.

[51] Int. Cl.$^6$ .................................................. A61K 31/70
[52] U.S. Cl. ............................................. 514/23; 514/851
[58] Field of Search ...................................... 514/23, 851

[56] References Cited

U.S. PATENT DOCUMENTS 5,693,521  12/1997  Tsien et al. ........................... 435/240.1

OTHER PUBLICATIONS

Berger et al., "Therapeutical Efficacy of a Novel Chloride Transport Blocker and an IP$_3$–Analogue in Vasogenic Brain Edema," *Acta Neurochir Supp.* 60:534–537 (1994).
Ho et al., "Ins(3,4,5,6)P$_4$ specifically inhibits a receptor–mediated Ca$^{2+}$–dependent Cl$^-$ current in CFPAC–1 cells," *Am. J. Physiol.* 272:C1160–C1168 (1997).
Ismailov et al., "A biologic function for an "orphan" messenger: D–myo–Inositol 3,4,5,6–tetrakisphosphate selectively blocks epithelial calcium–activated chloride channels," *Proc. Natl. Acad. Sci USA* 93:10505–10509 (1996).
Kachintorn et al., "Elevation of inositol tetrakisphosphate parallels inhibition of Ca$^{2+}$–dependent Cl$^-$ secretion in T84 cell," *Am. J. Physiol.* 264 (3 Pt 1):C671–C676 (1993).
Kruppa et al., "Bioactivatable derivatives of 8–Substituted cAMP–analogues," *Bioorganic & Medicinal Chemistry Letters* 7(7):945–948 (1997).
Li et al., "Membrane–permeant esters of inositol polyphosphates, chemical syntheses and biological applications," *Tetrahedron* 53(35):12017–12040 (1997).
Roemer et al., "Synthesis of D–myo–Inositol 3,4,5,6–and 1,4,5,6–Tetrakisphosphate Analogues and their Membrane–permeant Derivatives," *J. Chem. Soc., Chem. Commun.* N4:411–412 (1995).
Roemer et al., "Membrane–permeant analogues of the putative second messenger myo–inositol 3,4,5,6–tetrakisphosphate," *J. Chem. Soc., Perkin Trans. 1* N14:1683–1694 (1996).
Schultz et al., "Membrane–permeant derivatives of cyclic AMP optimized for high potency, prolonged activity, or rapid reversibility," *Molecular Pharmacology* 46:702–708 (1994).
Schultz et al., "Acetoxymethyl esters of phosphates, enhancement of the permeability and potency of cAMP," *J. Biol. Chem.* 268(9):6316–6322 (1993).
Staub et al., "Treatment of Vasogenic Brain Edema with the Novel Cl$^-$ Transport Inhibitor Torasemide," *J. of Neurotrauma* 11(6):679–690 (1994).
Tan et al., "Properties of the Inositol 3,4,5,6–tetrakisphosphate 1–Kinase Purified from Rat Liver," *J. Biol. Chem.* 272(4):2285–2290 (1997).
Uribe et al., "Phosphatidylinositol 3–Kinase Mediates the Inhibitory Effect of Epidermal Growth Factor on Calcium–dependent Chloride Secretion," *J. Biol. Chem.* 271(43):26588–26595 (1996).
Uribe et al., "Epidermal growth factor inhibits Ca$^{2+}$–dependent Cl$^-$ transport in T84 human colonic epithelial cells," *Am. J. Physiol.* 271(3 Pt 1):C914–C922 (1996).
Vajanaphanich et al., "Long–term uncoupling of chloride secretion from intracellular calcium levels by Ins(3,4,5,6)P$_4$," *Nature* 371:711–714 (1994).
Roemer et al., "Antagonists of the novel second messenger Ins(3,4,5,6)P$_4$," Symposium on Hormones and Cell Regulation, Sep., 1996.
Schultz et al., "Membrane–permeant derivatives of inositol polyphosphates: effects on cytosolic Ca$^{2+}$ and Ca$^{2+}$–regulated processes," Calcium Signaling: 20th Karolinska Institute Nobel Conference, Saltsjöbaden, Sweden (1992).
Vajanaphanich et al., "Cross–talk between calcium and cAMP–dependent intracellular signaling pathways," *J. Clin. Invest.* 96:386–393 (1995).
Xie et al., "Inositol 3,4,5,6–Tetrakisphosphate Inhibits the Calmodulin–dependent Protein Kinase II–activated Chloride Conductance in T84 Colonic Epithelial Cells," *J. Biol. Chem.* 271(24):14092–14097 (1996).
Zhuo et al., "Role of guanylyl cyclase and cGMP–dependent protein kinase in long–term potentiation," *Nature* 368:635–639 (1994).

*Primary Examiner*—Kevin E. Weddington
*Attorney, Agent, or Firm*—Campbell & Flores LLP

[57] ABSTRACT

The present invention provides compositions that are cell permeable antagonists of inositol polyphosphates. In addition, the invention provides methods for enhancing chloride ion secretion from a cell by contacting the cells with cell permeable antagonists of inositol polyphosphates. The invention also provides methods for enhancing chloride ion secretion in an individual by administering cell permeable antagonists of inositol polyphosphates to the individual. The invention additionally provides methods for alleviating a sign or symptom associated with cystic fibrosis in an individual by administering a cell permeable antagonist of inositol polyphosphates to the individual. The invention also provides compositions that are cell permeable agonists of inositol polyphosphates. In addition, the invention provides methods for decreasing chloride ion secretion from a cell by contacting the cell with cell permeable agonists of inositol polyphosphates. The invention also provides methods for decreasing chloride ion secretion in an individual by administering cell permeable agonists of inositol polyphosphates to the individual. The invention additionally provides methods for alleviating a sign or symptom associated with secretory diarrhea in an individual by administering cell permeable agonists of inositol polyphosphates to the individual.

72 Claims, 22 Drawing Sheets

*myo*-inositol

*scyllo*-inositol

2-O-butyryl-1-O-methyl-*myo*-Ins(3,4,5,6)P$_4$/AM

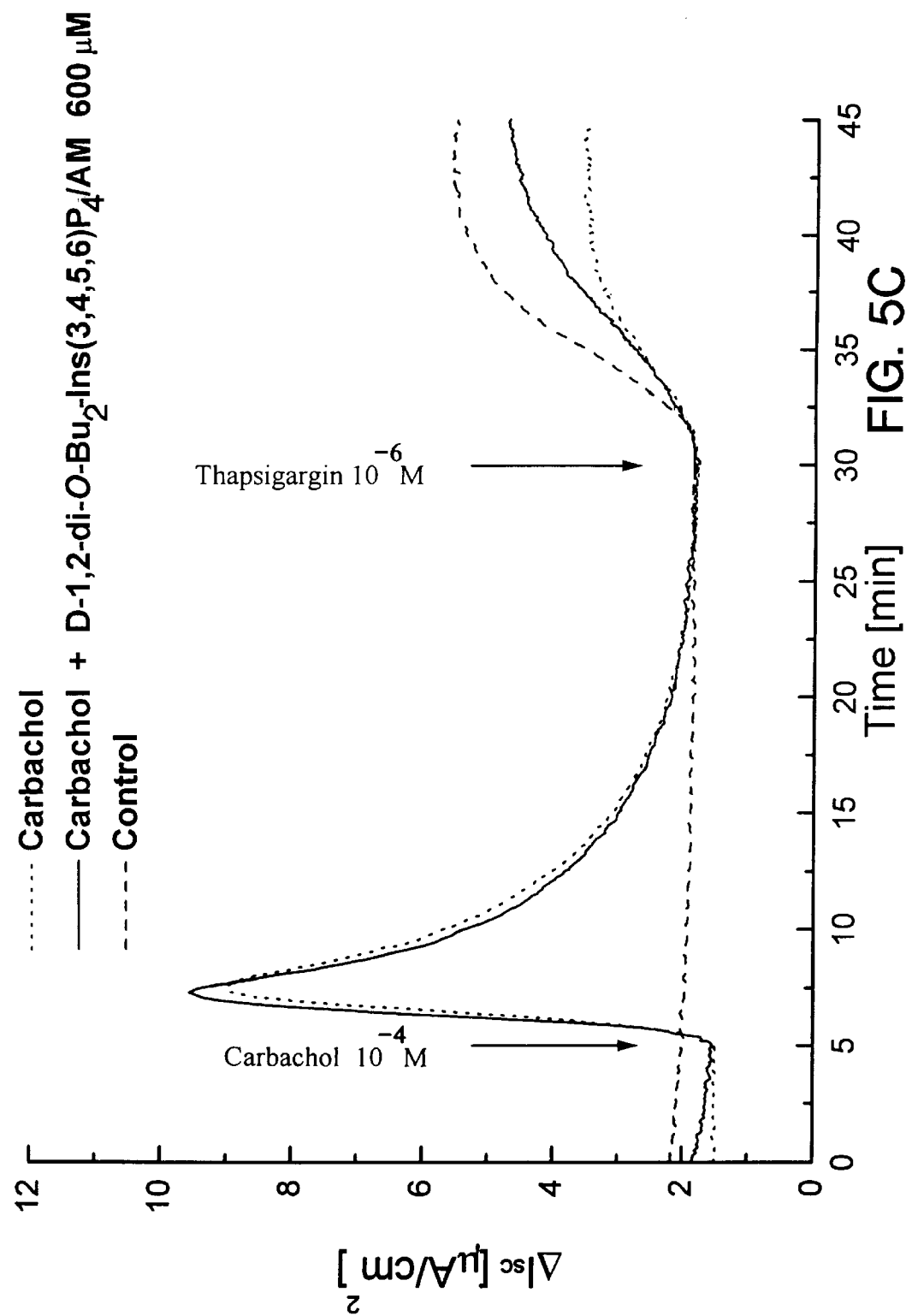

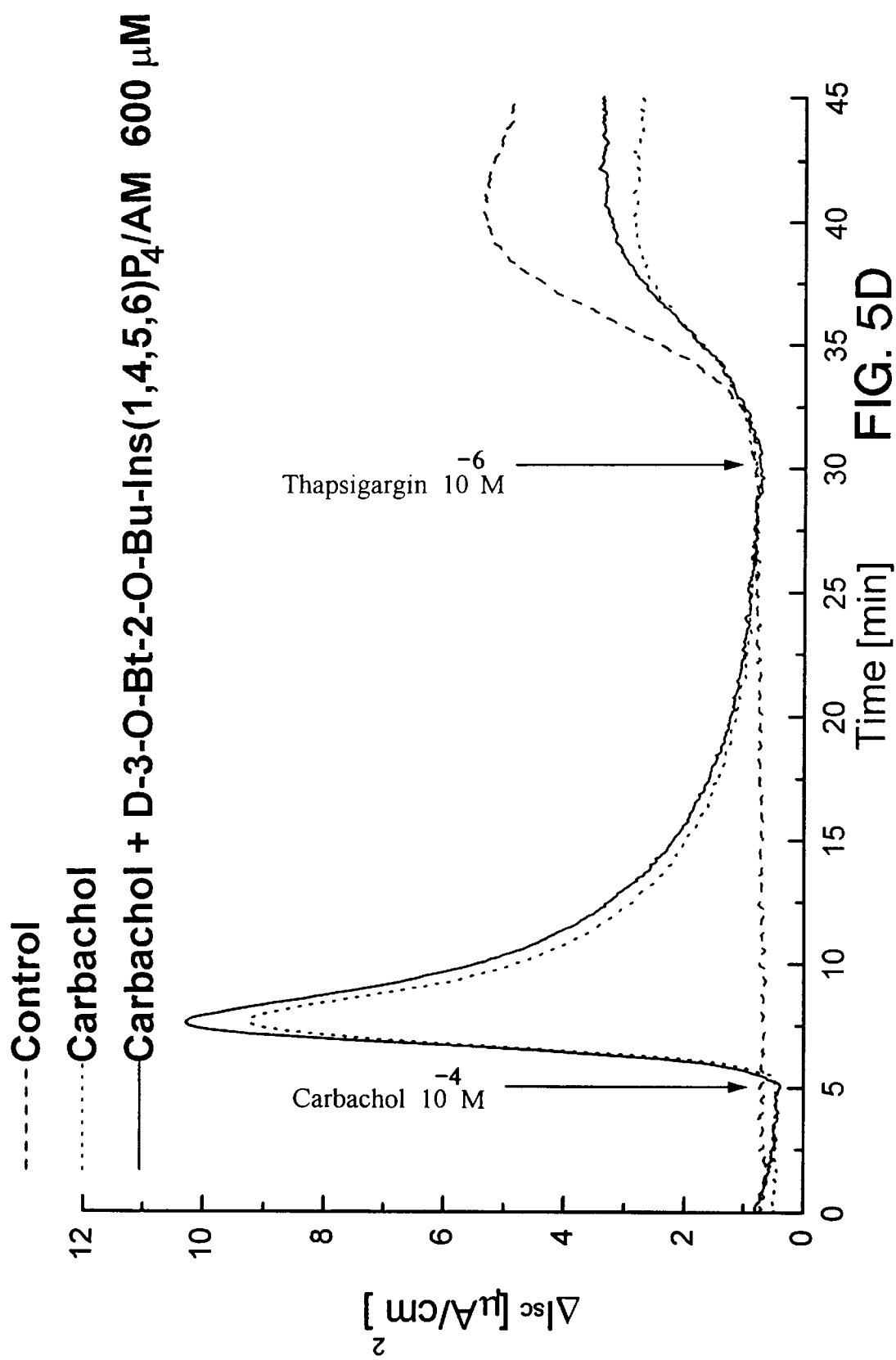

PIP₃ and a membrane-permeant derivative

Synthetic pathway to PIP$_3$/AM

Synthetic pathway to PIP$_3$/AM

Synthetic pathway to 1,2-cyclohexylidene-Ins(3,4,5,6)P$_4$/AM

INOSITOL POLYPHOSPHATE DERIVATIVES AND METHODS OF USING SAME

This application is a continuation-in-part of U.S. Ser. No. 08/926,831, filed Sep. 10, 1997, now U.S. Pat. No. 5,880,099 and claims the benefit of priority of U.S. provisional application No. 60/077,178, which was converted from U.S. Ser. No. 08/717,122, filed Sep. 20, 1996, the entire contents of which is incorporated herein by reference.

This invention was made with government support under grant number R01 DK47240-01A1 awarded by National Institutes of Health. The government has certain rights in the invention.

BACKGROUND OF THE INVENTION

1. Field of the Invention

The present invention relates generally to compounds and methods for modulating chloride ion transport, and, more specifically, to antagonists and agonists of inositol polyphosphates.

2. Background Information

All living organisms are made of cells. The boundary of a cell is determined by the plasma membrane which serves to segregate materials on the inside from those on the outside. The cell membrane functions by regulating the passage of materials such as nutrients into or out of the cell. The transport of ions across cell membranes serves many important functions in a cell, including the regulation of oncotic pressure of the cell. The regulation of ion transport provides cells with the appropriate concentration of ions to maintain their integrity and function. Under inappropriate conditions, for example, if the ion concentration inside the cell is too high, water moves into the cell and causes it to swell or burst. If the ion concentration in the cell is too low, the cell shrinks.

Organisms exploit the cell membrane ion transport properties to regulate fluids in particular tissue types. For example, cells lining the intestine regulate water uptake using ion transport. One particularly important ion transported by cells is chloride ion. Chloride ion transport plays a key role in a variety of cellular functions such as osmoregulation, intracellular pH regulation, and salt and fluid secretion.

In the intestine, high levels of chloride ion secretion are associated with diseases such as secretory diarrhea. Secretory diarrhea has many causes, including infection by microorganisms such as Salmonella, Shigella, and certain strains of *Escherichia coli*. Other conditions associated with the regulation of fluid levels in tissues and chloride ion secretion include tissue swelling associated with inflammation, infection or trauma. Thus, methods for inhibiting undesirable levels of chloride ion secretion could be used to alleviate symptoms of these pathologies.

Cystic fibrosis is the most common lethal genetic disease in Caucasians, affecting approximately one in 2,000 births among Americans of European descent. It is characterized by abnormally viscous mucous secretions, which lead to chronic pulmonary disease, pancreatic insufficiency and intestinal obstructions. In the United States, approximately 30,000 people have cystic fibrosis and about 1,000 new cases are diagnosed every year. Although, in the past, afflicted children often died as infants, individuals can now survive into their twenties and thirties. Nevertheless, there is no cure for cystic fibrosis and current therapies do not correct the underlying cellular defect but only manage the symptoms of the disease.

Current treatments for cystic fibrosis are largely confined to symptom management or control of opportunistic infections. For example, the use of vaccinations for viral pathogens and culture-specific antibiotics for bacterial infections can be used to prevent infection. Corticosteroids are sometimes useful in the treatment of the inflammatory response to infections but have a variety of undesirable long term side effects. Other treatments focus on the symptoms of chronic pulmonary disease associated with abnormally viscous mucous secretions in the lung. For example, physical assistance such as chest percussion and postural drainage aids in clearing the secretions from the lungs. Bronchodilators have been beneficial in some patients, but in others have resulted in decreased gas exchange. Other symptoms associated with abnormally viscous mucous secretions include intestinal obstructions and pancreatic insufficiency. Intestinal obstructions occur in 20% of adults and are treated with enemas, or, where enemas are not effective, by surgery.

Pancreatic insufficiency occurs in 80 to 90% of the patients and is caused by decreased secretion of bicarbonate ions and fluid due to impaired recycling of chloride ions out of the cell. The corresponding pancreatic fluid becomes hyperconcentrated in protein and becomes inspissated, causing obstruction of the pancreatic ducts and subsequent atrophy of pancreatic acini. Pancreatic insufficiency is treated with enzyme supplementation, which usually restores adequate digestive and absorptive functions, thereby correcting symptoms of malnourishment. However, the underlying disease persists, often causing recurrent bouts of pancreatitis that can lead to atrophy of the pancreas.

A treatment that restores normal pulmonary function, normal secretory function to the colon or normal pancreatic function would provide a great advantage over currently available therapies. Gene therapy has been used on cystic fibrosis patients. However, attempts at gene therapy have been unsuccessful for a variety of reasons, including the extraordinary size of the gene, immune reactions to adenovirus vectors used to transfer the gene and the rapid turnover of epithelial tissue.

Thus, there exists a need for a means to alter chloride ion secretion so as to ameliorate the symptoms of pathologies such as cystic fibrosis and secretory diarrhea which are associated with abnormal chloride transport. The present invention satisfies this need and provides related advantages as well.

SUMMARY OF THE INVENTION

The present invention provides compositions that are cell permeable antagonists of inositol polyphosphates. For example, the invention provides antagonists of myo-inositol 3,4,5,6-tetrakisphosphate and phosphatidylinositol trisphosphate. In addition, the invention provides methods for enhancing chloride ion secretion from a cell by contacting the cells with cell permeable antagonists of inositol polyphosphates. The invention also provides methods for enhancing chloride ion secretion in an individual by administering cell permeable antagonists of inositol polyphosphates to the individual. The invention additionally provides methods for alleviating a sign or symptom associated with cystic fibrosis in an individual by administering a cell permeable antagonist of inositol polyphosphates to the individual.

The invention also provides compositions that are cell permeable agonists of inositol polyphosphates. For example, the invention provides agonists of myo-inositol 3,4,5,6-tetrakisphosphate and phosphatidylinositol trisphosphate. In addition, the invention provides methods for decreasing chloride ion secretion from a cell by contacting the cell with cell permeable agonists of inositol polyphosphates. The invention also provides methods for decreasing chloride ion secretion in an individual by administering cell permeable agonists of inositol polyphosphates to the individual. The invention additionally provides methods for alleviating a sign or symptom associated with secretory diarrhea in an individual by administering cell permeable agonists of inositol polyphosphates to the individual.

DETAILED DESCRIPTION OF THE INVENTION

Figure 1:
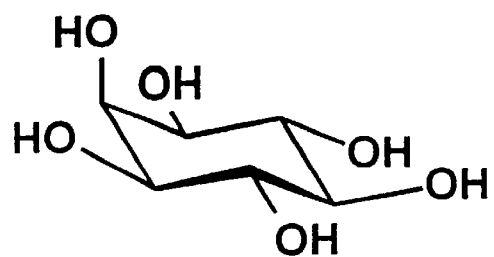
FIG. 1 shows the structures of myo-inositol, scyllo-inositol and a representative cell permeable inositol polyphosphate derivative, 2-Bt-1-Me-Ins(3,4,5,6)$P_4$/AM.
Figure 1:
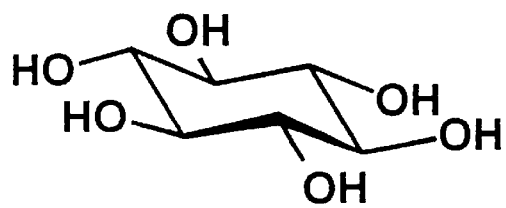
Figure 1:
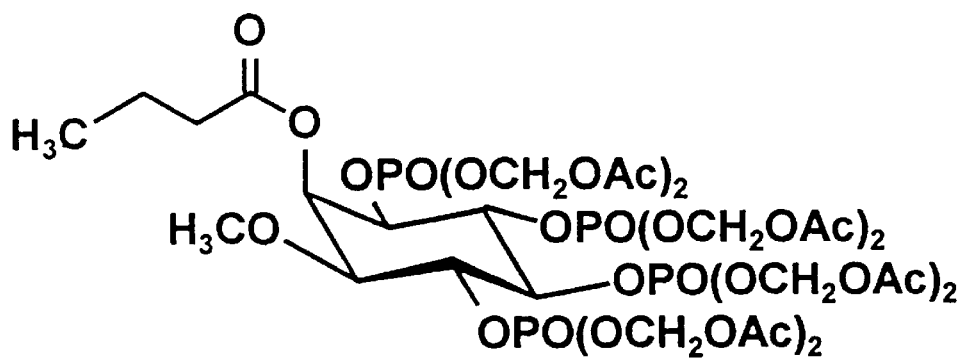

The invention provides compositions and methods for altering chloride ion secretion by contacting cells with cell permeable compounds that are antagonists or agonists of inositol polyphosphates. As used herein, the term "altering" refers to enhancing or decreasing chloride ion secretion such that the level of chloride ion transport into or out of a cell is different than the level of secretion in cells not treated with an agonist or antagonist of the invention. As used herein, the term "antagonist" means that a compound has the function of reducing the physiological activity of another compound. For example, an antagonist of a compound that inhibits chloride ion secretion reverses that inhibition. Similarly, the term "agonist" means that a compound has the function of mimicking the physiological activity of another compound.

An antagonist of the invention enhances chloride ion secretion from cells. As used herein, the term "enhancing," when used in reference to increasing chloride ion secretion, means that the level of chloride ion transport out of a cell is higher than the level of secretion in corresponding cells not treated with an antagonist. Conversely, the term "decreasing," when used in reference to inhibiting chloride ion secretion, means that the level of chloride ion transport out of a cell is lower than the level of secretion in corresponding cells not treated with an agonist. As used herein, the term "contacting" refers to incubating or exposing a cell to a cell permeable compound such that the compound can pass through the cell membrane.

Abnormal chloride ion secretion is associated with various pathological conditions. Accordingly, the compounds of the invention are useful for enhancing or decreasing chloride ion secretion, thereby alleviating symptoms of such diseases. In certain pathological conditions, such as cystic fibrosis, enhancement of chloride ion secretion can be useful for alleviating symptoms of the disease, whereas, in other pathological conditions, such as secretory diarrhea, decreasing chloride secretion can alleviate the symptoms. As used herein, the term "alleviating" refers to relieving or lessening a symptom of a disease. Thus, depending on the chloride ion secretion abnormality, the invention provides compositions and methods to compensate for abnormal chloride ion secretion associated with a particular disease.

The invention provides compounds that are agonists or antagonists of inositol polyphosphates. Inositol polyphosphate derivatives can function as inositol polyphosphate agonists and antagonists. The effects of compounds of the invention on Ins(3,4,5,6)$P_4$- and PtdInsP$_3$-mediated inhibition of calcium-mediated chloride ion secretion are described in the Examples and summarized in Table I.

The invention provides cell permeable compounds that regulate chloride ion secretion through calcium-dependent chloride ion channels by mimicking or antagonizing the activity of the endogenous inhibitors of calcium-mediated chloride ion secretion, Ins(3,4,5,6)$P_4$ or PtdInsP$_3$. As disclosed herein, compounds that increase the intracellular concentration of Ins(3,4,5,6)$P_4$ or PtdInsP$_3$ are useful for inhibiting chloride ion secretion. In contrast, compounds that antagonize the effect of Ins(3,4,5,6)$P_4$ or PtdInsP$_3$ are useful for enhancing chloride ion secretion.

TABLE I

The Effects of Inositol Polyphosphate Derivatives on Chloride Ion Secretion

| Derivative[1] | Abbreviation[2] | Inhibition of Cl⁻ Secretion | Ability to Block Inhibition | Mechanism and Inositol Polyphosphate Pathway Affected |
|---|---|---|---|---|
| 1,2-di-O-butyryl myo-inositol 3,4,5,6-Tkphosphate oct (acetoxymethyl) ester | $Bt_2$—Ins(3,4,5,6)$P_4$/AM | + |  | Agonist of Ins(3,4,5,6)$P_4$ |
| 2-O-butyryl-1-O-methyl-myo-inositol 3,4,5,6-TKphosphate oct (acetoxymethyl) ester | 2-Bt-1-Me—Ins(3,4,5,6)$P_4$/AM | − | + | Antagonist of Ins(3,4,5,6)$P_4$ |
| 1,2-di-O-methyl-myo-inositol 3,4,5,6-Tkphosphate oct (acetoxymethyl-) ester | $Me_2$—Ins(3,4,5,6)$P_4$/AM | − | + | Antagonist of Ins(3,4,5,6)$P_4$ |

TABLE I-continued

The Effects of Inositol Polyphosphate Derivatives on Chloride Ion Secretion

| Derivative[1] | Abbreviation[2] | Inhibition of Cl$^-$ Secretion | Ability to Block Inhibition | Mechanism and Inositol Polyphosphate Pathway Affected |
|---|---|---|---|---|
| D,L-1;2-dicyclohexylidene-myo-inositol 3,4,5,6-TKphosphate oct (acetoxymethyl) ester | D,L-1,2-cyclohexylidene-Ins(3,4,5,6) P$_4$/AM | | + | Antagonist of Ins(3,4,5,6) P$_4$ |
| 1-O-butyl-2-O-butyryl-myo-inositol 3,4,5,6-TKphosphate oct (acetoxymethyl) ester | 1-Bu-2-Bt—Ins(3,4,5,6) P$_4$/AM | | + | Antagonist of Ins(3,4,5,6) P$_4$ |
| 1,2-di-O-butyl-myo-inositol 3,4,5,6-TKphosphate oct (acetoxymethyl) ester | Bu$_2$—Ins(3,4,5,6) P$_4$/AM | | + | Antagonist of Ins (3,4,5,6)P$_4$ |
| 1-O-butyryl-2-O-butyl-myo-inositol 3,4,5,6-TKphosphate oct (acetoxymethyl) ester | 1-Bt-2-Bu-Ins(3,4,5,6) P$_4$/AM | – | | |
| 2,3-di-O-methyl-myo-inositol 3,4,5,6-TKphosphate oct (acetoxymethyl) ester | Me$_2$—Ins(1,4,5,6) P$_4$/AM | – | – | |
| 2-O-butyryl-3-O-methyl-myo-inositol 3,4,5,6-TKphosphate oct (acetoxymethyl) ester | 2-Bt-3-Me—Ins(1,4,5,6) P$_4$/AM | – | – | |
| D,L-1,2-O-butyrl-scyllo-inositol 3,4,5,6-TKphosphate oct (acetoxymethyl) ester | D,L-Bt$_2$—scyllo-Ins (3,4,5,6) P$_4$/AM | + | | Agonist of Ins(3,4,5,6) P$_4$ |
| D,L-1-0-butyryl-2-O-methyl-myo-inositol 3,4,5,6-TKphosphate oct (acetoxymethyl) ester | D,L-1-Bt-2-Me—Ins(3,4,5,6) P$_4$/AM | + | | Agonist of Ins(3,4,5,6) P$_4$ |
| D,L-1,2-dichloro-1,2-dideoxy-myo-inositol 3,4,5,6-TKphosphate oct (acetoxymethyl) ester | D,L-1,2 Cl$_2$—1,2 dideoxy-Ins(3,4,5,6) P$_4$/AM | – | | |
| 3-O-butyryl-2-O-butyl-myo-inositol 1,4,5,6-Tkphosphate oct (acetoxymethyl) ester | 3-Bt-2-Bu—Ins(1,4,5,6) P$_4$/AM | – | | |
| 2,3-di-O-butyl-myo-inositol 1,4,5,6-TKphosphate oct (acetoxymethyl) ester | Bu$_2$—Ins(1,4,5,6) P$_4$/AM | – | | |
| 3-O-butyl-2-O-butyryl-myo-inositol 1,4,5,6-TKphosphate oct (acetoxymethyl) ester | 3-Bu-2-Bt—Ins(1,4,5,6) P$_4$/AM | – | | |
| D,L-2,5,6-tri-O-butyryl-myo-inositol 1,3,4-trisphosphate hex (acetoxymethyl) ester | D,L-Bt$_3$—Ins(1,3,4) P$_3$/AM | + | | Agonist of Ins(3,4, 5, 6) P$_4$ |
| 2,3-di-O butyryl-myo-inositol 1,4,5,6-TKphosphate oct (acetoxymethyl) ester | Bt$_2$—Ins(1,4,5,6) P$_4$/AM | | + | Antagonist of PtdInsP$_3$ |
| sn-di-O-palmitoyl-D,L-6-O-butyryl-phosphatidyl-inositol 3,4,5-trisphosphate hepta (acetoxymethyl) ester | diC$_{16}$—Bt—PtdIns P$_3$/AM | | + | Agonist of PtdInsP$_3$ |
| sn-di-O-octanoyl-D,L-6-O-butyryl-phosphatidyl-inositol-3,4,5-trisphosphate hepta (acetoxymethyl) ester | diC$_8$—Bt—PtdIns (3,4,5) P$_3$/AM | | + | Agonist of PtdInsP$_3$ |
| D,L-1-0-butyryl-2-0-deoxy-inositol 3,4,5,6-TKphosphate oct (acetoxymethyl) ester | D,L-1-Bt-2-deoxy-Ins (3,4,5,6) P$_4$/AM | | | Agonist of Ins(3,4,5,6) P$_4$ |

[1]Derivatives listed use the following abbreviations: TK, tetrakisphosphate; oct, octakis, hex, hexakis. Unless otherwise indicated, all compounds are the D form.
[2]Abbreviations used in the table and throughout the application: Ins, inositol; P, phosphate; P$_n$, n designates the number of phosphates; AM, acetoxymethyl ester; Bt, butyryl; Me, methyl; Bu, butyl; C$_{16}$, palmitoyl; C$_8$, octanoyl; PtdIns, phosphatidylinositol.
Unless otherwise indicated, all derivatives are myoinositol derivatives.

The cell permeable compounds of the invention, which readily pass through the plasma membrane, can be useful for directly increasing the intracellular concentration of Ins(3,4,5,6)P$_4$ or PtdInsP$_3$ or for mimicking the effects of Ins(3,4,5,6)P$_4$ or PtdInsP$_3$ due to structural similarities.

Alternatively, the cell permeable compounds of the invention are useful for antagonizing the effects of Ins(3,4,5,6)$P_4$ or PtdInsP$_3$. As disclosed herein, inositol polyphosphate derivatives can function as cell permeable agonists or antagonists of Ins(3,4,5,6)$P_4$ or PtdInsP$_3$.

Cell permeable inositol polyphosphate derivatives were synthesized as described in Example XI. These compounds are cell permeable because the charged phosphate groups are masked by acetoxymethyl ester groups and the hydroxyl groups are masked by hydrophobic chemical groups (see FIG. 1). A hydrophobic chemical group useful for masking a hydrophilic group can be, for example, an acyl group, an alkyl group, an alkylidene group, or any hydrophobic chemical group that can mask hydrophilic groups on inositol polyphosphates. The alkyl groups include methyl, ethyl, propyl, iso-propyl, butyl, iso-butyl, tert-butyl, sec-butyl, 1-methylbutyl, 2,2-dimethylbutyl, 2-methylpentyl, 2,2-dimethylpropyl, pentyl and hexyl as well as alkylene groups, cyclic chains of carbon atoms such cyclohexyl and cyclopentyl groups, as well as combinations of linear or branched chains and cyclic chains of carbon atoms such as a methyl-cyclohexyl or cyclopropyl-methylene group. With respect to methyl derivatives, however, 2-Bt-1-Me-Ins(3,4,5,6)$P_4$/AM, Me$_2$-Ins(3,4,5,6)$P_4$/AM, Me$_2$-Ins(1,4,5,6)$P_4$/AM, 2-Bt-3-Me-Ins(1,4,5,6)$P_4$/AM and D,L-1-Bt-2-Me-Ins(3,4,5,6)$P_4$/AM are not within the claimed compositions. In addition, it should be recognized that an alkyl as defined herein can be substituted with a substituent. The alkylidene groups, which are acetal groups, include, for example, methylidene, ethylidene, propylidene, butylidene, pentylidene, hexylidene, cyclobutylidene, cyclopentylidene, cyclohexylidene and cycloheptylidene (Kemp and Vellaccio, *Organic Chemistry*, Worth Publishers, New York (1980)), which is incorporated herein by reference. The acyl groups include, for example, acetyl, propanyl, butyryl, hexanoyl and valeryl. With respect to acyl derivatives, however, Bt$_2$-Ins(3,4,5,6)$P_4$/AM, D,L-Bt$_2$-scyllo-Ins(3,4,5,6)$P_4$/AM and Bt$_2$-Ins(1,4,5,6)$P_4$/AM are not within the claimed compositions. Once inside the cell, butyryl and acetoxymethyl ester groups are cleaved by intracellular esterases. Thus, modification with these hydrophobic functional groups allows compounds to cross the cell membrane where they are hydrolyzed to expose hydrophilic groups of the non-derivatized compound. The alkyl and alkylidene groups, in contrast, are non-hydrolyzable and thus are retained on the derivative after crossing the cell membrane.

Additional modifications of inositol polyphosphates provide cell permeable derivatives. For example, Ins(3,4,5,6)$P_4$ derivatives, including
1,2-dideoxy-Ins(3,4,5,6)$P_4$/AM,
1-Bt-2-deoxy-Ins(3,4,5,6)$P_4$/AM,
2-Bt-1-deoxy-Ins(3,4,5,6)$P_4$/AM and
1,2-dichloro-1,2-dideoxy-myo-Ins(3,4,5,6)$P_4$/AM, also are cell permeable derivatives (see Table I). In addition, cell permeable PtdInsP$_3$ derivatives include, for example,
diC$_{16}$-6-O-Bt-PtdIns(3,4,5)$P_3$/AM and
diC$_8$-6-O-Bt-PtdIns(3,4,5)$P_3$/AM, as well as
diC$_{16}$-2-O-Bt-PtdIns(3,4,5)$P_3$/AM,
diC$_8$-2-O-Bt-PtdIns(3,4,5)$P_3$/AM,
diC$_{16}$-2,6-O-Bt$_2$-PtdIns(3,4,5)$P_3$/AM and
diC$_8$-2,6-O-Bt$_2$-PtdIns(3,4,5)$P_3$/AM. Methods for synthesizing the acylated and acetoxymethyl ester derivatives are described by Roemer et al. (*J. Chem. Soc., Chem. Commun.* N4:411 (fat 1995); *J. Chem. Soc., Perkins Trans.* 1 N14:1683 (fat 1996)), each of which is incorporated herein by reference.

The invention provides cell permeable compounds that are antagonists of inositol polyphosphates. In one embodiment, the cell permeable compounds are Ins(3,4,5,6)$P_4$ antagonists. As disclosed herein, Ins(3,4,5,6)$P_4$ derivatives function as Ins(3,4,5,6)$P_4$ antagonists. For example, Ins(3,4,5,6)$P_4$ derivatives with alkyl groups attached to the hydroxyl group at position 1, position 2 or both function as antagonists of Ins(3,4,5,6)$P_4$ (see Table I and Examples III and IV). Particularly useful alkyl group derivatives are methyl (Me) and butyl (Bu) derivatives. For example, 2-Bt-1-Me-Ins(3,4,5,6)$P_4$/AM, Me$_2$-Ins-(3,4,5,6)$P_4$/AM, 1-Bu-2-Bt-Ins(3,4,5,6)$P_4$/AM and Bu$_2$-Ins(3,4,5,6)$P_4$/AM each reversed Ins(3,4,5,6)$P_4$-mediated inhibition of chloride ion secretion and, therefore, are Ins(3,4,5,6)$P_4$ antagonists. Other useful Ins(3,4,5,6)$P_4$ derivatives are those containing an alkylidene group on position 1 and position 2. For example, D,L-1,2-cyclohexylidene-Ins(3,4,5,6)$P_4$/AM reversed carbachol-mediated inhibition of chloride ion secretion and, therefore, is an Ins(3,4,5,6)$P_4$ antagonist. In addition, Ins(1,4,5,6)$P_4$/AM derivatives with an alkylidene group on position 2 and position 3 also can be used as an Ins(1,4,5,6)$P_4$ derivative.

In another embodiment, the cell permeable compounds are PtdInsP$_3$ antagonists. As disclosed herein, cell permeable Ins(1,4,5,6)$P_4$ derivatives are PtdInsP$_3$ antagonists. For example, Ins(1,4,5,6)$P_4$ derivatives with butyryl groups attached at positions 2 and 3 reversed EGF-mediated and PtdInsP$_3$-mediated inhibition of calcium-mediated chloride ion secretion and, therefore, are PtdInsP$_3$ antagonists (see Table I and Examples VII and VIII).

The invention also provides cell permeable compounds that are agonists of inositol polyphosphates. In one embodiment, the cell permeable compounds are Ins(3,4,5,6)$P_4$ agonists. As disclosed herein, Ins(3,4,5,6)$P_4$ derivatives are Ins(3,4,5,6)$P_4$ agonists. For example, Bt$_2$-Ins(3,4,5,6)$P_4$/AM, Bt$_2$-scyllo-Ins(3,4,5,6)$P_4$/AM and 1-Bt-2-deoxy-Ins(3,4,5,6)$P_4$/AM (36% inhibition) inhibit calcium-mediated chloride secretion by uncoupling chloride ion secretion from intracellular calcium concentrations and, therefore, are Ins(3,4,5,6)$P_4$ agonists (see Table I and Examples I to III). In addition, Ins(1,3,4)$P_3$ derivatives are Ins(3,4,5,6)$P_4$ agonists. For example, Bt$_3$-Ins(1,3,4)$P_3$/AM inhibits calcium-mediated chloride ion secretion by increasing intracellular concentrations of Ins(3,4,5,6)$P_4$ and, therefore, are Ins(3,4,5,6)$P_4$ agonists (see Example V).

In another embodiment, the cell permeable compounds are PtdInsP$_3$ agonists. As disclosed herein, PtdInsP$_3$ derivatives are PtdInsP$_3$ agonists. For example, diC$_{16}$-Bt-PtdInsP$_3$/AM and diC$_8$-Bt-PtdInsP$_3$/AM inhibited calcium-mediated chloride ion secretion and, therefore, are PtdInsP$_3$ agonists (see Table I and Example VIII).

Molecular modeling of the structure of inositol polyphosphate derivatives can be used to design synthetic compounds with structural features that mimic the desired activity of the inositol polyphosphate derivative. Alternatively, cell permeable synthetic compounds that act as agonists or antagonists of inositol polyphosphates can be identified, for example, by screening a combinatorial chemistry library. Using the methods described herein, synthetic compounds can be screened for the desired activity of mimicking or antagonizing the effect of a given inositol polyphosphate on calcium-mediated chloride ion secretion. Methods for making and screening combinatorial chemistry libraries are well known to those skilled in the art (*Combinatorial Peptide and Nonpeptide Libraries: A Handbook*, Jung, ed., VCH, New York (1996)), which is incorporated herein by reference.

The invention additionally provides methods for altering chloride ion secretion by contacting cells with cell permeable compounds that are antagonists or agonists of inositol polyphosphates. Movement of chloride ions is used by cells to regulate water flow within the body of an organism. Cells have specific chloride ion channels that only allow chloride ions to pass through the membrane when the channels are open. These channels are especially important in cells in mucous membranes, which secrete mucins and regulate water flow. When water flow into and out of cells is deficient, mucin secretion results in viscous plugs, which obstruct airways in the lungs and the mucosal lining of the intestine in diseases such as cystic fibrosis. Not all chloride ion channels are the same, however, and different channels are regulated in different ways.

A specific group of chloride ion channels, the calcium-dependent chloride ion channels, are linked to calcium ion flux. When the intracellular concentration of calcium ions increases, chloride ion secretion increases. As used herein, the term "chloride ion secretion" refers to the transport of chloride ions across the plasma membrane of a cell. Treatment of cells with certain compounds such as histamine, a physiologically relevant agonist that does not have a measurable long term effect on inositol polyphosphate metabolism, causes an increase in intracellular calcium ion concentration that results in increased chloride ion secretion.

Carbachol, a muscarinic cholinergic compound, also increases intracellular calcium ion concentration and stimulates chloride ion secretion with short term treatment. However, following long-term treatment of colonic epithelial $T_{84}$ cells with carbachol, increased concentrations of intracellular calcium ions no longer stimulate chloride ion secretion (Kachintorn et al., *Am. J. Physiol. Cell* 264:C671 (1993)), which is incorporated herein by reference. Long-term treatment with carbachol leads to a slow and prolonged rise of intracellular Ins(3,4,5,6)$P_4$ levels (Vajanaphanich, et al., *Nature* 371:711 (1994)), which is incorporated herein by reference. Treatment of $T_{84}$ cells with a mixture of $Bt_2$-Ins (3,4,5,6)$P_4$/AM and $Bt_2$-Ins(1,4,5,6)$P_4$/AM inhibited chloride ion secretion in response to increased concentrations of intracellular calcium induced by thapsigargin whereas $Bt_2$-Ins(1,4,5,6)$P_4$/AM had no effect. As exemplified herein, enantiomerically pure $Bt_2$-Ins(3,4,5,6)$P_4$/AM inhibited chloride ion secretion in response to increased concentrations of intracellular calcium (see Example I). Thus, Ins(3,4,5,6)$P_4$ is an endogenous negative regulator of calcium-mediated chloride ion secretion because it uncouples chloride ion secretion from calcium ion concentration.

Another mechanism for inhibiting calcium-mediated chloride ion secretion distinct from that mediated by Ins(3,4,5,6)$P_4$ is by increasing levels of PtdInsP$_3$. EGF inhibits calcium-mediated chloride ion secretion induced by carbachol and thapsigargin in $T_{84}$ cells (Uribe et al., *Am. J. Physiol.* 271:C914 (1996a)). EGF triggers a 1.7-fold increase in Ins(3,4,5,6)$P_4$ levels, compared to carbachol, which triggers up to a 20-fold increase in Ins(3,4,5,6)$P_4$. These results suggest that EGF modulates calcium-mediated chloride ion secretion through a different mechanism than Ins(3,4,5,6)$P_4$.

EGF activates phosphatidylinositol 3-kinase (PI 3-kinase) and the inhibitory effect of EGF on calcium-mediated chloride ion secretion is mediated by PI 3-kinase (Uribe et al., *J. Biol. Chem.* 271:26588 (1996b)). EGF stimulated an increase in levels of the PI 3-kinase products, phosphatidylinositol 3,4-bisphosphate (PtdInsP$_2$) and PtdInsP$_3$. These PI 3-kinase products increased with a time course that paralleled EGF inhibition of chloride ion secretion. Wortmannin, which is a highly specific PI 3-kinase inhibitor, blocked formation of PtdInsP$_3$ and PtdInsP$_2$ and reversed the EGF induced inhibition of chloride ion secretion. Thus, a mechanism involving PtdInsP$_3$ was responsible for EGF induced inhibition of calcium-mediated chloride ion secretion.

Since the compounds of the invention are agonists and antagonists of inositol polyphosphates, which regulate chloride ion secretion, these compounds are useful for altering chloride ion secretion in cells. The cell permeability of the compounds allows delivery of the compounds to the cytoplasm, the site of inositol polyphosphate action, by contacting cells with the compounds.

The invention provides a method for enhancing chloride ion secretion across a cell membrane by contacting a cell with a cell permeable antagonist of an inositol polyphosphate. In one embodiment, Ins(3,4,5,6)$P_4$ antagonists are used to enhance chloride ion secretion. As disclosed herein, Ins(3,4,5,6)$P_4$ derivatives can be used as Ins(3,4,5,6)$P_4$ antagonists. In another embodiment, PtdInsP$_3$ antagonists are used to enhance chloride ion secretion. As disclosed herein, Ins(1,4,5,6)$P_4$ derivatives can be used as PtdInsP$_3$ antagonists.

The invention also provides a method for decreasing chloride ion secretion across a cell membrane by contacting a cell with a cell permeable agonist of an inositol polyphosphate. In one embodiment, Ins(3,4,5,6)$P_4$ agonists are used to decrease chloride ion secretion. As disclosed herein, Ins(3,4,5,6)$P_4$ derivatives can be used as Ins(3,4,5,6)$P_4$ agonists. In addition, Ins(1,3,4)$P_3$ derivatives can be used as Ins(3,4,5,6)$P_4$ agonists. In another embodiment, PtdInsP$_3$ agonists are used to decrease chloride ion secretion. As disclosed herein, PtdInsP$_3$ derivatives can be used as PtdInsP$_3$ agonists.

The invention provides a method for enhancing chloride ion secretion in an individual by administering to the individual an antagonist of Ins(3,4,5,6)$P_4$ or PtdInsP$_3$. As used herein, the term "individual" refers to an organism, which generally is a mammal, particularly a human, to be treated with agonistic or antagonistic compounds of the invention that enhance or decrease chloride ion secretion. The chloride ion secretion enhancement or decrease occurs in the cells comprising one or more tissue organs in the individual. As used herein, the term "administering" or "administration" refers to introducing the antagonist or agonist to an individual in a manner and form such that the antagonist or agonist is delivered to the appropriate target tissue or tissues, where it can contact the target cells, thereby altering chloride ion secretion of the cells. The invention additionally provides a method for alleviating a sign or symptom associated with cystic fibrosis by administering an antagonist of Ins(3,4,5,6)$P_4$ or PtdInsP$_3$ or both to an individual exhibiting the sign or symptom.

The invention also provides a method for decreasing chloride ion secretion in an individual by administering to the individual an agonist of Ins(3,4,5,6)$P_4$ or PtdInsP$_3$. In addition, the invention provides a method for alleviating a sign or symptom associated with secretory diarrhea by administering an agonist of Ins(3,4,5,6)$P_4$ or PtdInsP$_3$ to an individual exhibiting the sign or symptom.

An antagonist or agonist generally is administered to an individual as a pharmaceutical composition. Such a pharmaceutical composition contains the antagonist or agonist and a pharmaceutically acceptable vehicle. Pharmaceutically acceptable vehicles are well known in the art and include aqueous solutions such as physiologically buffered saline or other solvents or vehicles such as glycols, glycerol, oils such as olive oil or injectable organic esters.

A pharmaceutically acceptable vehicle can contain physiologically acceptable compounds that act, for example, to stabilize the antagonist or agonist or increase the absorption of the agent. Such physiologically acceptable compounds include, for example, carbohydrates such as glucose, sucrose or dextrans, antioxidants such as ascorbic acid or glutathione, chelating agents, low molecular weight proteins or other stabilizers or excipients. One skilled in the art would know that the choice of a pharmaceutically acceptable vehicle, including a physiologically acceptable compound, depends, for example, on the route of administration of the antagonist or agonist of the invention and the target tissue or tissues.

Several routes of administration can be used depending on the individual to be treated and the target tissue or tissues. The pharmaceutical composition can be administered by various routes, including, for example, orally, rectally, or parenterally, such as intravenously, intramuscularly, subcutaneously, intraorbitally, intracapsularly, intraperitoneally, intracisternally or by passive or facilitated absorption through the skin using, for example, a skin patch or transdermal iontophoresis, respectively. Furthermore, the composition can be administered by injection, intubation or topically, the latter of which can be passive, for example, by direct application of an ointment or powder, or active, for example, using a nasal spray or inhalant.

The total effective dose can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of the agent required to obtain an effective dose in a subject depends on many factors including the age and general health of the subject as well as the route of administration and the number of treatments to be administered. In view of these factors, the skilled artisan would adjust the particular dose so as to obtain an effective dose.

The dosage of a particular compound is determined by the intracellular concentration required to achieve the desired effect, for example, enhancing or decreasing chloride ion secretion. The effective intracellular concentration can be determined using methods as disclosed herein or otherwise known in the art. For example, the effective intracellular concentration of the agonist $Bt_2$-Ins(3,4,5,6)$P_4$/AM was determined to be about 4 $\mu$M using an in vitro Ins(1,3,4)$P_3$-5/6-kinase assay (Vajanaphanich et al. supra, 1994). Thus, for $Bt_2$-Ins(3,4,5,6)$P_4$/AM, the dosage is chosen so as to provide an intracellular derivative concentration of about 4–20 $\mu$M, preferably 4 $\mu$M. Initial studies are conducted in a model system to determine the effectiveness of particular compounds. Determination of the effective concentration necessary to treat a pathological condition in an individual is determined in Phase I and Phase II clinical trials.

The compounds of the invention can be used alone, or in combination with each other or with other therapeutic agents to treat a pathological condition associated with abnormal chloride ion secretion. For example, the treatment protocol can begin with one compound and additional compounds can be administered with the first compound as needed if the relief due to the first compound is insufficient. The treatment can also be combined with other modes of treatment, such as administration of uridine 5'-triphosphate plus amiloride (see Bennett et al., Am. J. Respir. Crit. Care Med. 153:1796 (1996)), which is incorporated herein by reference.

The compositions and methods of the invention are useful for treating various pathologies, such as cystic fibrosis or secretory diarrhea, which are characterized, in part, by abnormal chloride ion secretion. Defective chloride ion secretion occurs in cystic fibrosis due to mutations in an epithelial cell chloride ion channel, the cystic fibrosis transmembrane regulator (CFTR). Chloride ion channels associated with the apical surface of epithelial cells are the principal control point regulating salt and fluid secretion. Most cases of cystic fibrosis are the result of a single point mutation, known as the $\Delta$F508 mutation, which results in the loss of the amino acid phenylalanine at amino acid position 508. This mutation interferes with transfer of the CFTR to the cell membrane, thereby reducing chloride ion secretion by the cell.

One approach to treatment of cystic fibrosis is to artificially activate other chloride ion channels. For example, in epithelial cells, the outwardly rectifying chloride channel (ORCC) is a chloride ion channel that is regulated by cyclic AMP. However, the ORCC is also believed to be regulated by the CFTR and, therefore, is less active in cystic fibrosis (Schwiebert et al., Cell 81:1063 (1995); Egan, et al., Nature 358:581 (1992); and Gabriel, et al., Nature 363:263 1993). In contrast, calcium-dependent chloride ion channels are more abundant in cells of a mouse model of cystic fibrosis (Grubb et al., Am. J. Physiol. 266:C1478 (1994)). Because calcium-dependent chloride ion channels are distinct from CFTR and are likely more abundant in cells of patients with cystic fibrosis, it should be possible to augment flux through these channels to compensate for the lack of flux through the CFTR. As disclosed herein, one or more antagonists of Ins(3,4,5,6)$P_4$ or PtdInsP$_3$ can be used to restore chloride ion secretion in epithelial cells affected by defects in the CFTR.

Several model systems are useful for assessing the ability of inositol polyphosphate derivatives of the invention to enhance chloride ion secretion. One such model is the human colonic epithelial $T_{84}$ cell line, which 5 has been studied extensively as a model secretory epithelium (Dharmsathaphorn et al. Am. J. Physiol. 246:G204 (1984)). $T_{84}$ cells exhibit a relatively differentiated phenotype when grown to confluence on permeable supports, forming polarized monolayers with tight junctions and vectorial transport. $T_{84}$ monolayers retain many receptor-mediated chloride ion secretory mechanisms including those involving changes in free cytosolic calcium and the CFTR (Cohn et al., Proc. Natl. Acad. Sci. USA 89:2340 (1992)). Agents such as histamine, carbachol, calcium ionophores and thapsigargin elevate intracellular calcium ions and stimulate varying degrees of chloride ion secretion across $T_{84}$ monolayers (Dharmsathaphorn et al., J. Clin. Invest. 84:945 (1989); Kachintorn, et al., supra, 1993). Cyclic AMP also stimulates chloride ion secretion through the CFTR in $T_{84}$ cells (Anderson and Welsh, Proc. Natl. Acad. Sci. USA 88:6003 (1991)). Thus, $T_{84}$ cells provide an in vitro model for the regulation of chloride ion secretion in normal and pathological conditions that involve defective chloride ion transport, such as cystic fibrosis. Additionally, epithelial cells of rabbit colon also provide a model of colonic epithelial cells.

Three of the more debilitating symptoms of cystic fibrosis are chronic pulmonary disease, pancreatic insufficiency and intestinal obstructions. Several model systems are available for characterizing the therapeutic effectiveness of inositol polyphosphate derivatives of the invention for treatment of these symptoms. For example, knockout of the CFTR gene in $T_{84}$ cells (CFTR$^-$ $T_{84}$ cells) provides a model for colonic epithelial cells that have a genetic background similar to that of colonic cells of cystic fibrosis patients (see Example X). The CFTR$^-$ $T_{84}$ cell line is useful for assessing the effectiveness of compounds of the invention, which are antagonists of Ins(3,4,5,6)$P_4$ and PtdInsP$_3$, at increasing chloride ion secretion.

Primary human nasal epithelial cells are a model of respiratory epithelium for testing the effect of various compounds on chloride ion secretion. Primary human nasal epithelial cells are useful for testing the function of compounds of the invention, which are antagonists of Ins(3,4,5,6)$P_4$ and PtdInsP$_3$, on chloride ion secretion in these cells (see Example IX).

A suitable model system for studying pancreatic function uses the pancreatic duct epithelial cell FTR$^-$ cell line, CFPAC, which is a human cell line derived from a pancreatic adenocarcinoma of a patient homozygous for the ΔF508 mutation. CFPAC cells lack cAMP-stimulated channel function but exhibit calcium-activated chloride ion channel activity (Shoemacher et al., *Proc. Natl. Acad. Sci. USA* 87:4012 (1990)). Dog pancreatic duct epithelial cells also are useful for testing the function of compounds of the invention, which are antagonists of Ins(3,4,5,6)$P_4$ and PtdInsP$_3$ on chloride ion secretion in these cells (Nguyen et al., *Am. J. Physiol.* 272:G172 (1997)), which is incorporated herein by reference.

Animal models of cystic fibrosis also are available for assessing the activity of Ins(3,4,5,6)$P_4$ and PtdInsP$_3$ antagonists. For example, CFTR knockout mice have been generated that provide models of cystic fibrosis (Rozmahel et al. *Nature Gen.* 12:280 (1996); Snouwaert et al., *Science* 257:1083 (1992); Ratiff et al., *Nature Gen.* 4:35 (1992); O3 Neal et al., *Hum. Molec. Genet.* 2:1561 (1993); and Dorin et al., *Nature* 359:211 (1992)), each of which is incorporated herein by reference. Increased levels of expression of calcium-dependent chloride ion channels correspond to improved viability in CFTR knockout mice (Clarke et al., *Proc. Natl. Acad. Sci USA* 91:479 (1994); and Rozmahel, et al., supra, 1996). Animal models are used to test the efficacy of compounds of the invention, which are antagonists of Ins(3,4,5,6)$P_4$ and PtdInsP$_3$, on chloride ion secretion in these animals. Animal models also are useful for testing the effectiveness of compounds of the invention on particular tissues in the animal.

Since cystic fibrosis symptoms arise in several organ systems, one skilled in the art would select a particular route and method of administration of the compound based on the symptom to be treated. The compounds are somewhat amphipathic and are soluble in aqueous solution. Alternatively, the compounds can be dissolved in dimethyl sulfoxide containing a surfactant. The compounds also can be dissolved in a solution containing FREON (1,1,2 trichlorotrifluoromethane), which has an advantage of low viscosity, allowing access to more diseased tissue and, thus, is useful for treatment during acute inflammation or during early stages of disease. For example, in a subject suffering from respiratory pathology, an antagonist of the invention can be suspended or dissolved in the appropriate pharmaceutically acceptable carrier and administered directly into the lungs using an inhalation device such as an inhaler nebulizer or turboinhaler. Thus, to alleviate mucous accumulation in the lung, the compounds can be administered in aerosol form directly to the target lung tissue. Alternatively, the compounds can be dissolved in FREON and can be delivered by lung perfusion. Such treatment can be maintained through periodic breathing of an atomized aqueous solution.

The clinical manifestations of cystic fibrosis, such as mucous viscosity, are well known and one in the art would know how to determine if a treatment protocol is effective in alleviating or preventing these known respiratory signs and symptoms of cystic fibrosis. For example, measurement of mucociliary clearance using ($^{99M}$Tc)iron oxide particles can be used to determine the effectiveness of treatment with compounds of the invention (Bennett, supra, 1996).

Other clinical manifestations of cystic fibrosis also can be treated with antagonists of Ins(3,4,5,6)$P_4$ or PtdInsP$_3$ using appropriate modes of administration. For example, sinus complications can be treated by administering pharmaceutical compositions in a nasal spray. This treatment is advantageous over current methods for treating sinus complications which often require multiple endoscopic surgeries that can result in facial deformities in patients with cystic fibrosis. For alleviation of intestinal disorders in cystic fibrosis, the agent can be administered by suppository or enema in an appropriate pharmaceutical vehicle. Alternatively, enteric coated tablets can be administered orally. In a subject suffering from pancreatitis, a pharmaceutical composition can be administered intravenously, orally or by any other method that distributes the compound systemically, including to the pancreas.

In addition to cystic fibrosis, other pathological conditions related to fluid buildup in tissues are amenable to treatment by altering chloride ion secretion. For example, swelling associated with inflammation, infection or trauma, such as brain swelling, can be alleviated by decreasing chloride ion secretion (Berger et al., *Acta Neurochir. Suppl.* (Wien) 60:534 (1994); and Staub et al., *J. Neurotrauma* 11:679 (1994)).

In contrast to pathological conditions such as cystic fibrosis, where chloride ion secretion is abnormally low, other pathological conditions are characterized, in part, by abnormally high levels of chloride ion secretion. For example, high levels of chloride ion secretion occur in secretory diarrhea. The invasive enteric bacteria Salmonella, which causes secretory diarrhea, is one of the most important causes of childhood death in the developing world and of health problems in the developed world. More than 1.3 billion cases of gastroenteritis and approximately 3 million deaths occur each year due to Salmonella infections. Because secretory diarrhea is associated with increased chloride ion flux across the gut epithelia, decreasing chloride ion secretion can alleviate symptoms of secretory diarrhea. The skilled artisan would recognize that methods of treating individuals with agonists of inositol polyphosphates to alleviate symptoms of secretory diarrhea are similar to those described above.

The invention provides compositions and methods for altering chloride ion secretion across a cell membrane by contacting a cell with a cell permeable agonist or antagonist of inositol polyphosphates. The invention also provides methods for altering chloride ion secretion in an individual by administering to the individual an agonist or antagonist of inositol polyphosphates. The invention further provides a method for alleviating a symptom associated with pathological conditions associated with abnormal chloride ion secretion by administering a pharmaceutical composition containing an agonist or antagonist of inositol polyphosphates. Thus, the compounds of the invention are useful as medicaments for alleviating the signs and symptoms of a pathological condition characterized, in part, by abnormal chloride ion secretion.

The following examples are intended to illustrate but not limit the present invention.

EXAMPLE I

Decreased Calcium-mediated Chloride Ion Secretion by a Cell Permeable Derivative of Ins(3, 4,5,6)$P_4$ in $T_{84}$ Cells This example demonstrates that a cell permeable derivative of Ins(3,4,5,6)$P_4$ decreases calcium-mediated chloride ion secretion in the colonic epithelial $T_{84}$ cell line by increasing the intracellular concentration of $Ins(3,4,5,6)P_4$.

Enantiomerically pure 1,2-$Bt_2$-$Ins(3,4,5,6)P_4$/AM was synthesized to determine if 1,2-$Bt_2$-$Ins(3,4,5,6)P_4$/AM mediates the uncoupling of chloride ion secretion from intracellular calcium concentrations. $T_{84}$ cells (passages 18–48) were maintained as described previously (Weymer, et al., *J. Clin. Invest.* 76:1828 (1985)), which is incorporated herein by reference. After 7–10 days of incubation on SNAP-WELLS (Corning Costar; Cambridge, Mass.), monolayers had formed tight junctions. Cell monolayers were preincubated with 100, 200 or 400 $\mu$M $Bt_2$-$Ins(3,4,5,6)P_4$/AM for 30 min prior to mounting. After an additional 30 min, 0.1 mM histamine was added and chloride ion secretion was monitored. Chloride ion secretion was measured as short circuit current ($I_{SC}$) across $T_{84}$ monolayers grown to confluence and mounted in Ussing chambers equipped with voltage clamps (Physiologic Instruments; San Diego, Calif.). Data was acquired and analyzed using "Acquire and Analyze" software (Physiologic Instruments).

Maximum decreases of histamine-stimulated chloride ion secretion was attained with 200 $\mu$M 1,2-$Bt_2$-$Ins(3,4,5,6)P_4$/AM with no further decrease with 400 $\mu$M (Table II). This result is consistent with previous studies showing that intracellular levels of $Ins(3,4,5,6)P_4$ near 4 $\mu$M, equivalent to 200 $\mu$M extracellular concentration, correspond to the onset of maximum inhibition (Vajanaphanich, et al., supra, 1994).

TABLE II

Decreased Calcium-dependent Chloride Ion Secretion by a Cell Permeable $Ins(3,4,5,6)P_4$ Derivative.

| $Bt_2Ins(3,4,5,6)$ $P_4$/AM (concentration) | Peak $\Delta Isc$ (% Control) after histamine (100 $\mu$M) Mean ± SEM | n | vs control (100%) |
|---|---|---|---|
| 100 $\mu$M | 75.1 ± 7.4 | 8 | p < 0.012 |
| 200 $\mu$M | 57.2 ± 15.1 | 6 | p < 0.037 |
| 400 $\mu$M | 69.3 ± 8.7 | 4 | p < 0.041 |

In contrast to the decrease in chloride ion secretion by cell permeable derivatives of $Ins(3,4,5,6)P_4$, no inhibition of dibutyryl cyclic AMP acetoxymethyl ester stimulated chloride ion secretion was observed (peak $\Delta I_{SC}$=96.3±9.1% or control; mean±SEM; n=4). This result is consistent with the observation that cyclic AMP-mediated chloride ion secretion occurs through a chloride ion channel distinct from the channel involved in calcium-mediated chloride ion secretion (McRoberts et al., *J. Biol. Chem.* 260:14163 (1985)).

These results demonstrate that increasing the intracellular concentration of $Ins(3,4,5,6)P_4$ by exposing cells to cell permeable derivatives of $Ins(3,4,5,6)P_4$ decreases calcium-mediated chloride ion secretion by uncoupling chloride ion secretion from intracellular calcium concentrations and that cell permeable $Ins(3,4,5,6)P_4$ derivatives are agonists of $Ins(3,4,5,6)P_4$.

EXAMPLE II

Decreased Calcium-mediated Chloride Ion Secretion by a Cell Permeable $Ins(3,4,5,6)P_4$ Derivative in Rabbit Colon This example demonstrates that increasing the intracellular concentration of $Ins(3,4,5,6)P_4$ using a cell permeable derivative of $Ins(3,4,5,6)P_4$ causes decreased calcium-mediated chloride ion secretion in rabbit colonic tissue.

Figure 2:
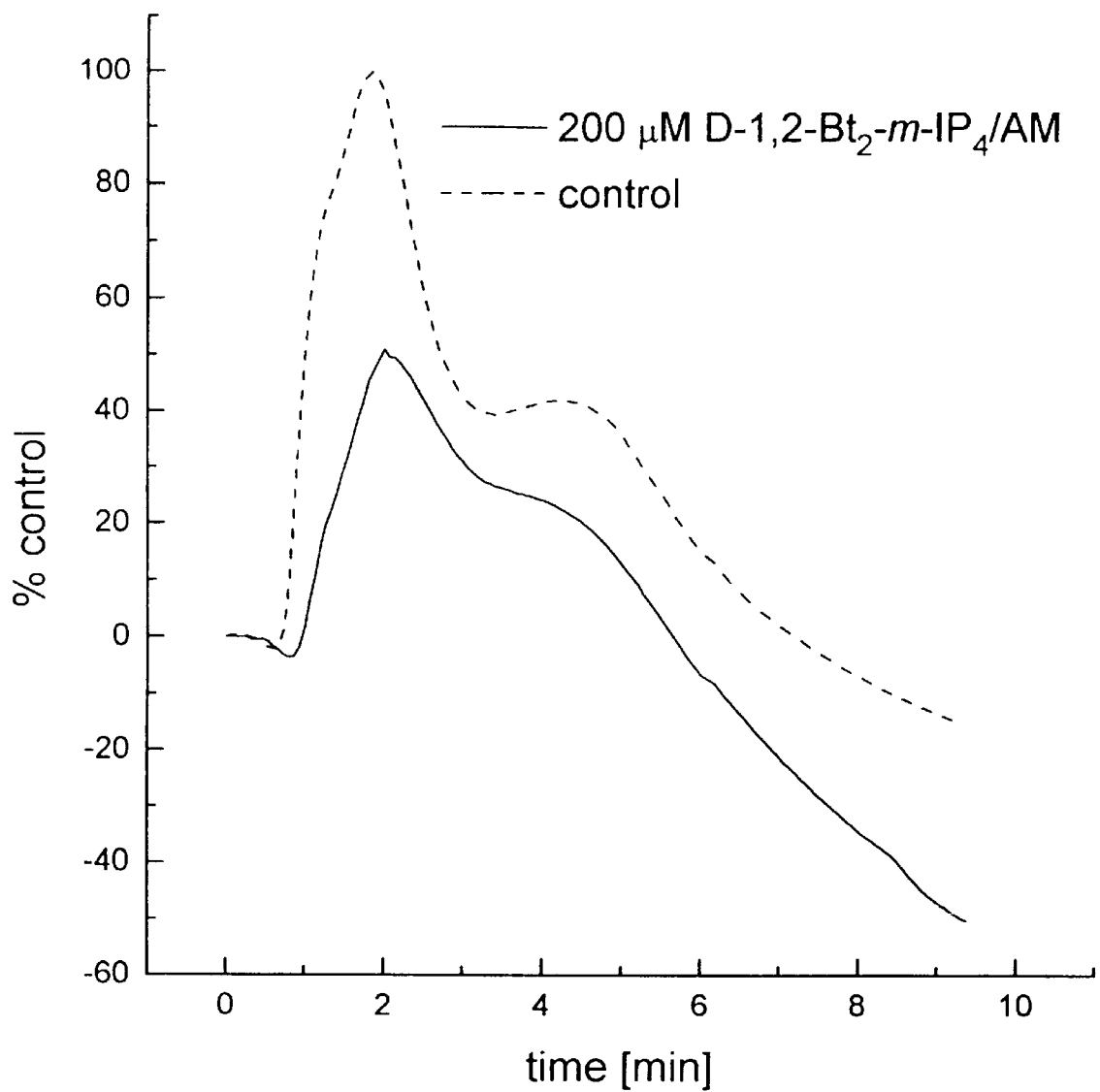
FIG. 2 shows $Bt_2$-Ins(3,4,5,6)$P_4$/AM inhibition of chloride ion secretion in rabbit colon.

The results obtained above using $T_{84}$ colonic epithelial cells in culture were confirmed using a rabbit colon model system (Frizzell et al., *J. Membrane Biol.* 27:297 (1976); and Frizzell and Schultz, *Int. Rev. Physiol.* 19:205 (1979)), each of which is incorporated herein by reference. Segments of rabbit colon were excised and used as a source of rabbit colonic epithelia. Briefly, segments of rabbit colon were washed with Ringers solution containing 141 mM $Na^+$, 5 mM $K^+$, 1.2 mM $Ca^{2+}$, 1.2 mM $Mg^{2+}$, 122 mM $Cl^-$, 25 mM $HCO_3$, 1.6 mM $HPO_4$, 0.4 mM $H_2PO_4$ and 10 mM glucose. At 37° C., this solution is pH 7.4 when gassed with 5% $CO_2$ and 95% $O_2$. Epithelium was stripped of the underlying muscle layer and mounted in modified SNAP WELLS (Frizzell et al., supra, 1976). Epithelia were preincubated with 200 $\mu$M 1,2-$Bt_2$-$Ins(3,4,5,6)P_4$/AM for 30 min at 37° C. and mounted in Ussing chambers. Short circuit current, conductance and resistance were measured at 4 sec intervals as described in Example I. Peak $I_{SC}$ was 50.9%±10.4 of controls which were incubated with vehicle (FIG. 2; mean±SEM, n=3; p<0.05 by Student's two tailed t-test). The % control shown in FIG. 2 represents $\Delta I_{SC}$ over peak $I_{SC}$ in control monolayers stimulated with histamine.

These results demonstrate that the cell permeable derivative $Bt_2$-$Ins(3,4,5,6)P_4$/AM acts as an agonist of $Ins(3,4,5,6)P_4$ by increasing the intracellular concentration of $Ins(3,4,5,6)P_4$ and decreases chloride ion secretion in rabbit colon. These results also confirm that the elevation of intracellular $Ins(3,4,5,6)P_4$ uncouples chloride ion secretion from intracellular calcium concentration in colon epithelial tissue.

EXAMPLE III

Reversal of $Ins(3,4,5,6)P_4$ Inhibition of Histamine-stimulated Chloride Ion Secretion Using $Ins(3,4,5,6)P_4$ Antagonists This example demonstrates that the inhibitory effect of $Ins(3,4,5,6)P_4$ on histamine-stimulated chloride ion secretion can be reversed by cell permeable derivatives of $Ins(3,4,5,6)P_4$ that function as antagonists of $Ins(3,4,5,6)P_4$.

The results shown in Examples I and II indicate that increasing concentrations of $Ins(3,4,5,6)P_4$ decreases calcium-mediated chloride ion secretion. Therefore, compounds that antagonize the function of $Ins(3,4,5,6)P_4$ in cells should reverse this decrease.

Initial studies were directed towards understanding structural determinants of $Ins(3,4,5,6)P_4$ responsible for the inhibitory effect on calcium-mediated chloride ion secretion. A series of cell permeable inositol polyphosphate derivatives were synthesized. These derivatives contained either one or two non-hydrolyzable chemical groups on the 1, 2 or 3 position. $T_{84}$ monolayers were preincubated for 30 minutes with 200 $\mu$M of 2-Bt-1-Me-$Ins(3,4,5,6)P_4$/AM, $Me_2$-$Ins(3,4,5,6)P_4$/AM, $Me_2$-$Ins(1,4,5,6)P_4$/AM or 2-Bt-3-Me-$Ins(1,4,5,6)P_4$/AM.

Following the incubation, cells were mounted in Ussing chambers. Calcium-mediated chloride ion secretion was stimulated with histamine ($10^{-4}$ M). Control values were the response to histamine in coincubated monolayers. Data are represented as mean peak $\Delta I_{SC}$±SEM, expressed as % control for 8 to 10 experiments. Significant differences were identified using the Student's two-tailed t test.

As shown in Table III, no inhibitory effect occurred in cells treated with any of the derivatives. These results indicate that the hydrogen-bonding donor potential at the 1 and 2 position participates in mediating the inhibitory effect of $Ins(3,4,5,6)P_4$ on calcium-mediated chloride ion secretion. The scyllo derivative of the cell permeable $Bt_2$-Ins(3, 4,5,6)$P_4$/AM was at least as effective an inhibitor as the myo derivative, indicating that the directionality of the 2-hydroxyl position is irrelevant for inhibitory activity.

Figure 3:
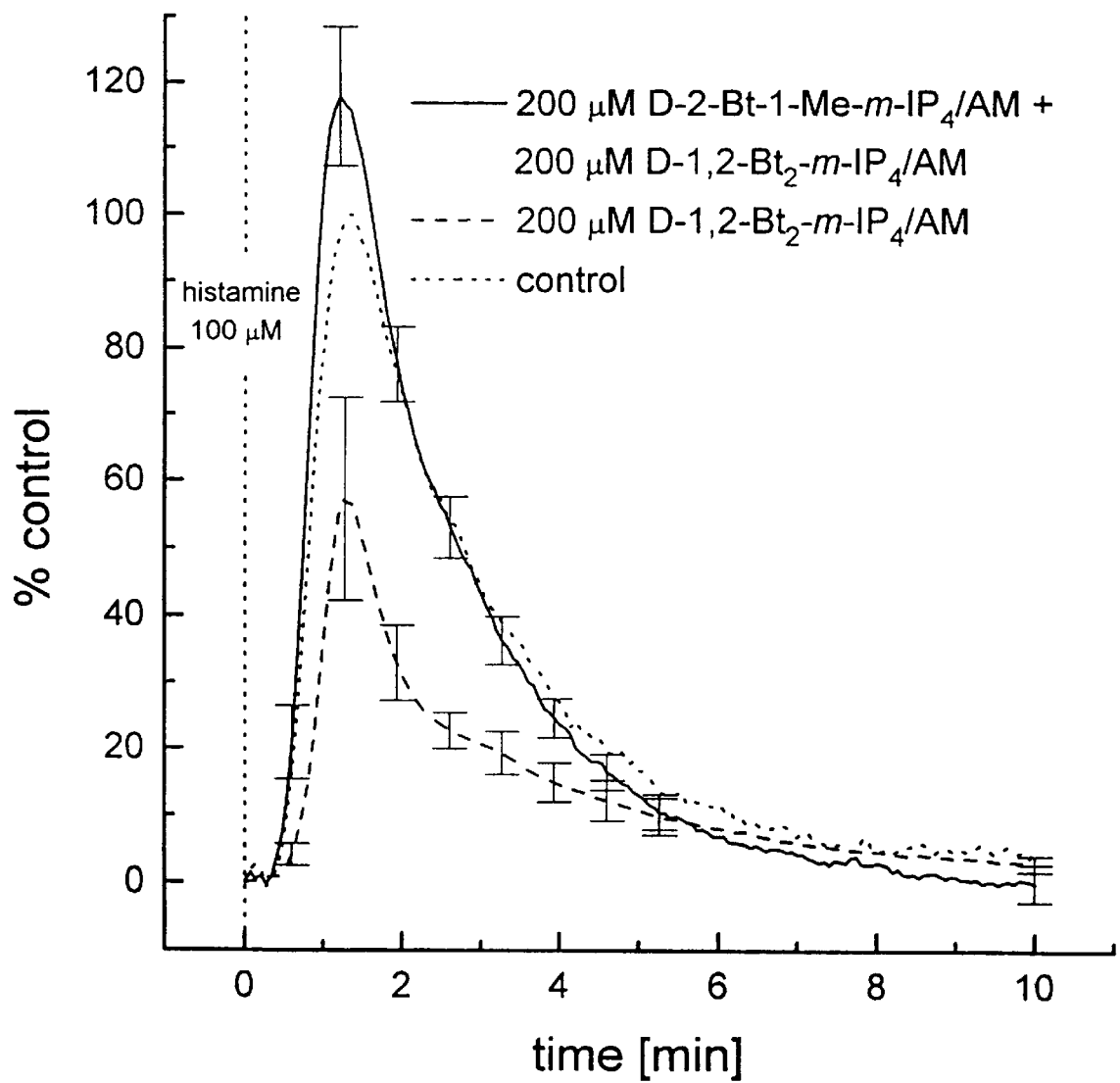
FIG. 3 shows enhanced chloride ion secretion in colonic epithelial $T_{84}$ cells treated with 200 $\mu$M 2-Bt-1-Me-Ins(3,4,5,6)$P_4$/AM due to the reversal of $Bt_2$-Ins(3,4,5,6)$P_4$/AM-mediated inhibition of histamine-stimulated chloride ion secretion.

$T_{84}$ cells were preincubated with cell permeant inositol polyphosphates as described above to determine if any of the inositol polyphosphate derivatives function as antagonists of Ins(3,4,5,6)$P_4$ inhibition of calcium-mediated chloride ion secretion. Following histamine stimulation, short circuit current was measured. As shown in FIG. 3, incubation with $Bt_2$-Ins(3,4,5,6)$P_4$/AM decreased histamine-stimulated chloride ion secretion relative to control cells. The % control shown in FIG. 3 represents $\Delta I_{SC}$ over peak $I_{SC}$ in control monolayers stimulated with histamine. However, preincubation with 2-Bt-1-Me-Ins(3,4,5,6)$P_4$/AM reversed the inhibitory effect of $Bt_2$-Ins(3,4,5,6)$P_4$/AM.

TABLE III

Reversal of Ins(3,4,5,6) $P_4$-mediated Decrease
in Chloride Ion Secretion by Derivatives of Ins(3,4,5,6) $P_4$

| $Bt_2Ins(3,4,5,6)$ $P_4/AM$ (concentration) | Antagonists | Peak $\Delta Isc$ (% Control) after histamine (100 μM) Mean ± SEM | n | vs control (100%) |
|---|---|---|---|---|
| 100 μM | | 75.1 ± 7.4 | 8 | p < 0.012 |
| 200 μM | | 57.2 ± 15.1 | 6 | p < 0.037 |
| 400 μM | | 69.3 ± 8.7 | 4 | p < 0.041 |
| — | 2-Bt-1-Me—Ins(3,4,5,6)P4/AM (200 μM) | 87.3 ± 6.6 | 8 | ns |
| — | $Me_2$-Ins(3,4,5,6) $P_4$/AM (200 μM) | 103.9 ± 11.1 | 8 | ns |
| — | $Me_2$—Ins(1,4,5,6) $P_4$/AM(200 μM) | 120.8 ± 10.6 | 8 | ns |
| — | 2-Bt-3-Me—Ins(1,4,5,6) $P_4$/AM (200 μM) | 105.5 ± 3.7 | 10 | ns |
| 200 μM | 2-Bt-1-Me—Ins (3,4,5,6) $P_4$/AM (200 μM) | 117.7 ± 10.6 | 8 | ns |
| 200 μM | $Me_2$—Ins(3,4,5,6) $P_4$/AM (200 μM) | 107.13 ± 10.2 | 8 | ns |
| 200 μM | 2-Bt-3-Me—Ins(1,4,5,6) $P_4$/AM (200 μM) | 69.7 ± 5.04 | 8 | p < 0.0005 |
| 200 μM | $Me_2$—Ins(1,4,5,6) $P_4$/AM (200 μM) | 68.4 ± 7.3 | 8 | p < 0.003 |
| — | $Bt_2$AMP/AM (2 μM) | 96.3 ± 9.1 | 4 | ns |
| — | $Bt_5$—Ins(1,4,5,6) ($P_4$/AM) (400 μM) | 137.9 ± 20.7 | 4 | ns |
| — | D,L-1-Bt-2-Me—Ins(3,4,5,6) $P_4$/AM (800 μM) | 114.2 ± 23.7 | 8 | ns |
| 200 μM | D,L-1-Bt-2-Me Ins(3,4,5,6) $P_4$/AM (400 μM) | 96.7 ± 14.8 | 3 | ns |
| — | D,L-1,2-$Cl_2$-dideoxy-Ins(3,4,5,6) $P_4$/AM (400 μM) | 89.39 ± 7.8 | 8 | ns |

The effect of various inositol polyphosphate derivatives on histamine-stimulated chloride ion secretion are shown in Table III. The Ins(3,4,5,6)$P_4$ derivatives 2-Bt-1-Me-Ins(3,4, 5,6)$P_4$/AM and $Me_2$-Ins(3,4,5,6)$P_4$/AM, reversed the inhibitory effect of $Bt_2$-Ins(3,4,5,6)$P_4$/AM on histamine-stimulated chloride ion secretion. In contrast, derivatives of Ins(1,4,5,6)$P_4$, $Me_2$-Ins(1,4,5,6)$P_4$/AM and 2-Bt-3-Me-Ins (1,4,5,6)$P_4$/AM, had essentially no effect. These results indicate that the reversal of the $Bt_2$-Ins(3,4,5,6)$P_4$/AM decrease on chloride ion secretion is stereospecific and demonstrate that these alkyl derivatives of Ins(3,4,5,6)$P_4$ function as antagonists of Ins(3,4,5,6)$P_4$.

Other derivatives were also tested. Preincubation with $Bt_2$-Ins(1,4,5,6)$P_4$/AM did not inhibit chloride ion secretion and in fact led to a slight increase in chloride ion secretion. The Ins(3,4,5,6)$P_4$ derviative, D,L-1,2-$Cl_2$-dideoxy-Ins(3,4, 5,6)$P_4$/AM had a slight inhibitory effect on chloride ion secretion. D,L-1-Bt-2-Me-Ins(3,4,5,6)$P_4$/AM did not inhibit chloride ion secretion and did not reverse the inhibition of $Bt_2$-Ins(1,4,5,6)$P_4$/AM.

Figure 4A:
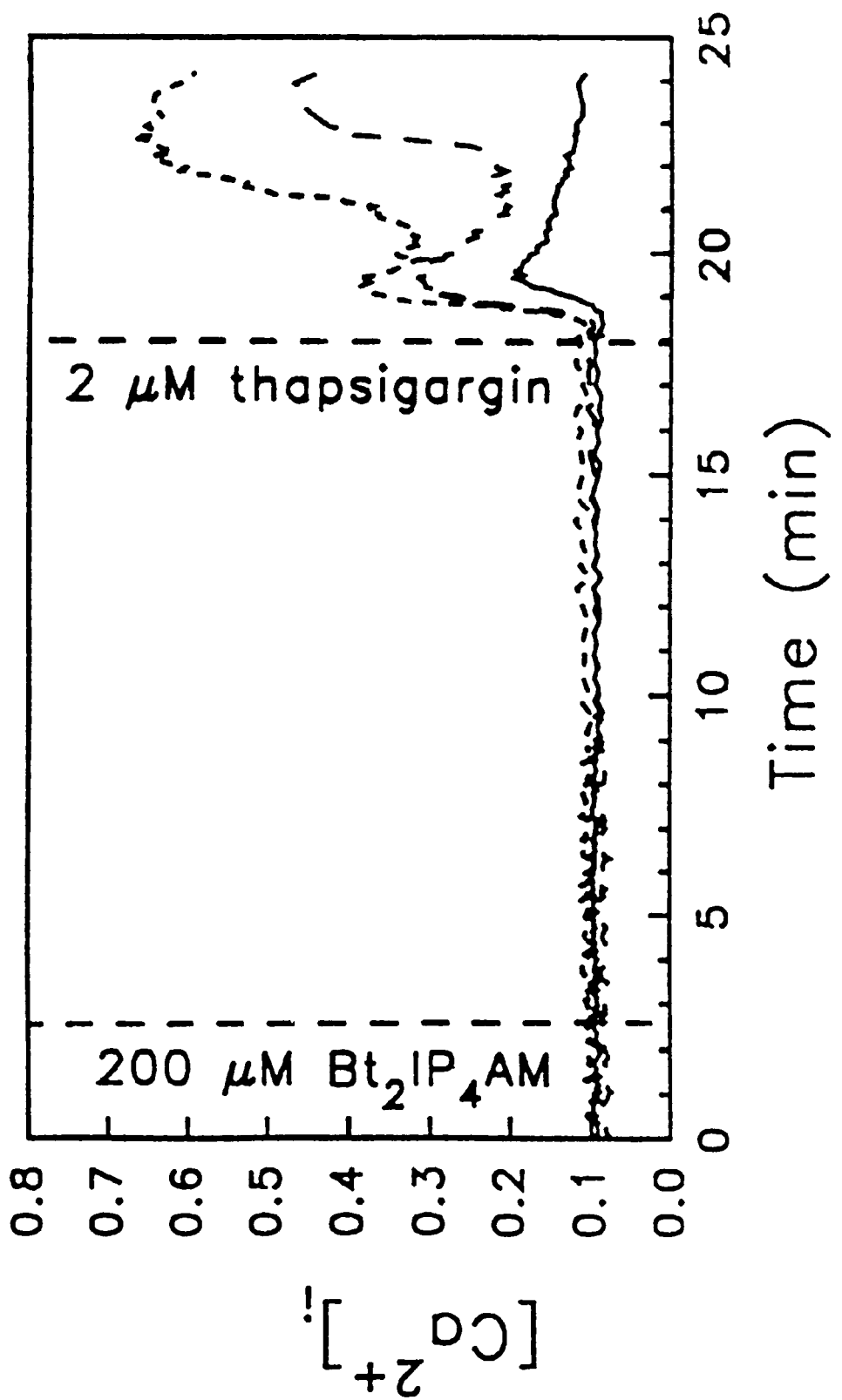
FIG. 4 shows that $Bt_2$-Ins(3,4,5,6)$P_4$/AM does not increase intracellular calcium and does not affect calcium response to thapsigargin.
Figure 4B:
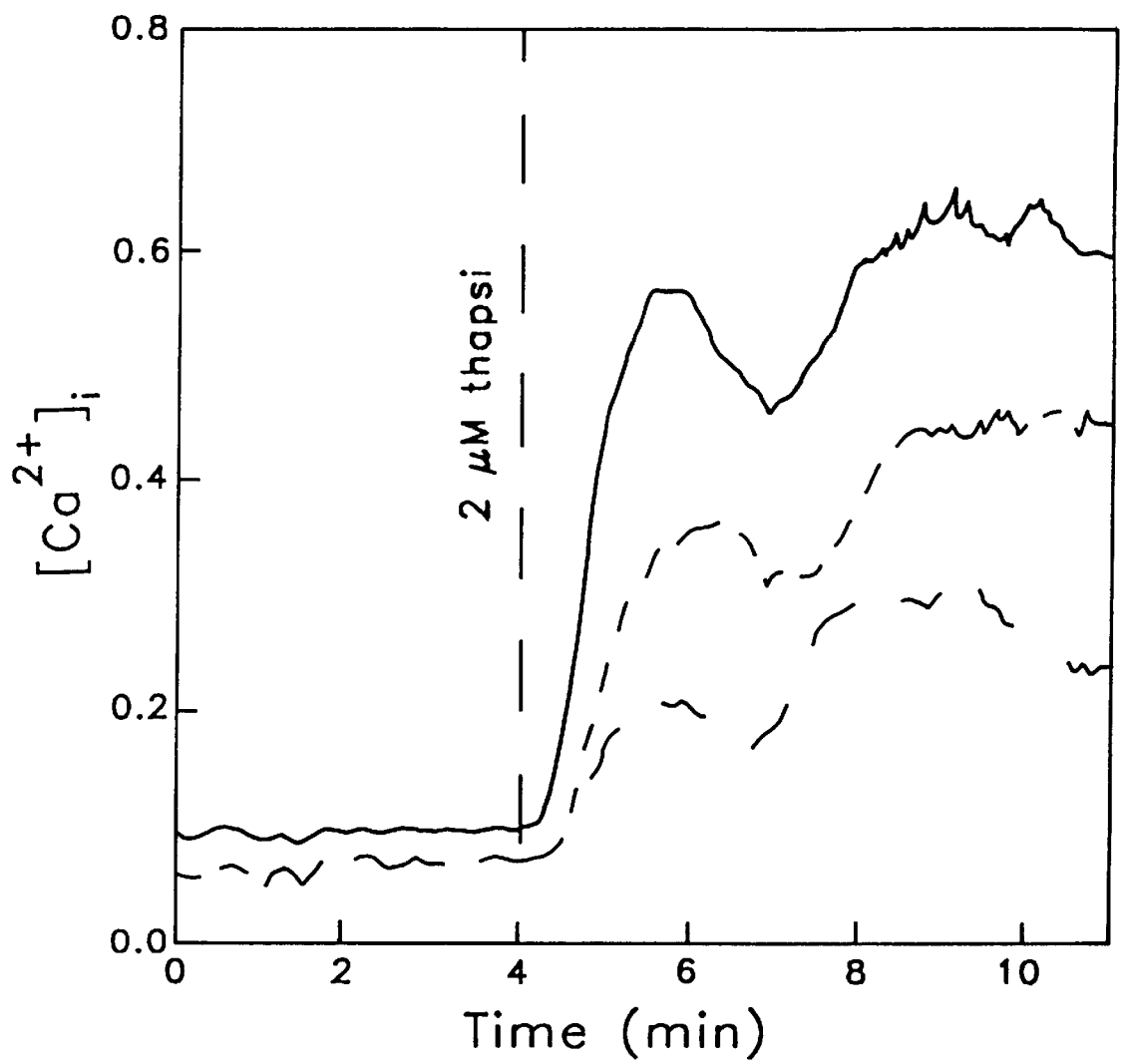

Elevation in intracellular calcium concentration leads to increased chloride ion secretion. To ensure that none of the effects of the inositol polyphosphate derivatives on chloride ion secretion were due to changes in calcium levels, the concentration of intracellular calcium was measured in cells treated with the inositol polyphosphate derivatives. As shown in FIG. 4, $Bt_2$-Ins(1,4,5,6)$P_4$/AM did not elevate intracellular calcium or the calcium response to thapsigargin. None of the compounds tested altered intracellular calcium levels by themselves or modified levels of intracellular calcium stimulated with carbachol or thapsigargin. Therefore, the effects of inositol polyphosphate derivatives on chloride ion secretion are not due to any effect on intracellular calcium concentrations.

These results demonstrate that cell permeable derivatives of Ins(3,4,5,6)$P_4$ reverse the decrease in calcium-mediated chloride ion secretion resulting from increased intracellular concentrations of Ins(3,4,5,6)$P_4$ due to treatment of cells with 1,2-$Bt_2$-Ins(3,4,5,6)$P_4$/AM, thereby enhancing calcium-mediated chloride ion secretion from these cells. In contrast, derivatives of the stereoisomer Ins(1,4,5,6)$P_4$ do not affect inhibition of chloride ion secretion mediated by Ins(3,4,5,6)$P_4$. Thus, cell permeable derivatives of Ins(3,4, 5,6)$P_4$ function as Ins(3,4,5,6)$P_4$ antagonists.

EXAMPLE IV

Reversal of Carbachol-mediated Decreases in Chloride Ion Secretion Using Ins(3,4,5,6)$P_4$ Antagonists This example demonstrates that carbachol-mediated decreases in chloride ion secretion can be reversed by cell permeable Ins(3,4,5,6)$P_4$ derivatives that function as antagonists of Ins(3,4,5,6)$P_4$.

In Example III above, intracellular Ins(3,4,5,6)$P_4$ was increased by the addition of the cell permeable derivative, $Bt_2$-Ins(3,4,5,6)$P_4$/AM, which is hydrolyzed by endogenous esterases to produce Ins(3,4,5,6)$P_4$. In this example, intracellular Ins(3,4,5,6)$P_4$ is increased by prolonged treatment of cells with carbachol.

$T_{84}$ colonic epithelial cells were treated with D,L-1,2-cyclohexylidene-Ins(3,4,5,6)$P_4$/AM, 1-Bu-2-Bt-Ins(3,4,5,6) $P_4$/AM, $Bu_2$-Ins(3,4,5,6)$P_4$/AM, 3-Bt-2-Bu-Ins(1,4,5,6)$P_4$/ AM, $Bu_2$-Ins(1,4,5,6)$P_4$/AM, 1-Bt-2-Bu-Ins(3,4,5,6)$P_4$/AM or 3-Bu-2-Bt-Ins(1,4,5,6)$P_4$/AM and the short circuit current was measured.

One set of cells was preincubated for 30 min with an inositol polyphosphate derivative. The other two sets of cells were preincubated with vehicle, alone. Measurement of $I_{SC}$ was initiated at time 0. At 5 min, carbachol ($10^{-4}$ M) was added to one set of cells preincubated with vehicle alone (designated "Carbachol" in FIG. 5) and to the set of cells preincubated with inositol polyphosphate derivatives (designated "Carbachol+D,L-1,2-Cyclohexylidene-Ins(3,4, 5,6)$P_4$/AM" in FIG. 5A). At 30 min, 1 $\mu$M thapsigargin was added. Data were collected for n=4 to 6 experiments.

Figure 5A:
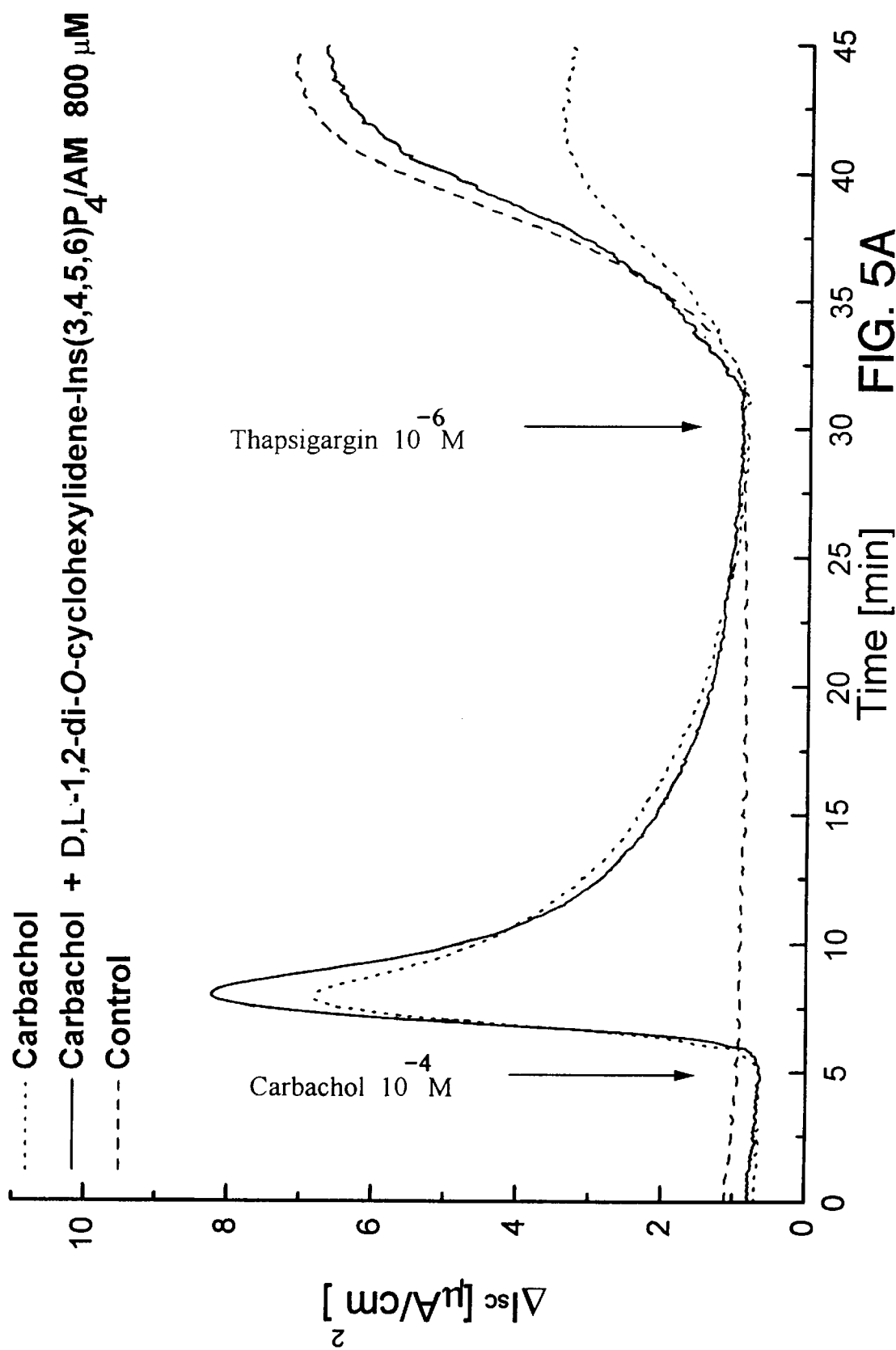
FIG. 5 shows enhanced chloride ion secretion in colonic epithelial $T_{84}$ cells treated with D,L-1,2-cyclohexylidene-Ins(3,4,5,6)$P_4$/AM (FIG. 5A); 1-Bu-2-Bt-Ins(3,4,5,6)$P_4$/AM (FIG. 5B); $Bu_2$-Ins(3,4,5,6)$P_4$/AM (FIG. 5C); 3-Bt-2-Bu-Ins(1,4,5,6)$P_4$/AM (FIG. 5D); $Bu_2$-Ins(1,4,5,6)$P_4$/AM (FIG. 5E); 1-Bt-2-Bu-Ins(3,4,5,6)$P_4$/AM (FIG. 5F); and 3-Bu-2-Bt-Ins(1,4,5,6)$P_4$/AM (FIG. 5G).

FIG. 5A shows an experiment using D,L-1,2-cyclohexylidene-Ins(3,4,5,6)$P_4$/AM. The addition of carbachol caused a transient increase in short circuit current in cells preincubated with the Ins(3,4,5,6)$P_4$ derivative and in cells treated with carbachol alone. At 30 min, following the return of $\Delta I_{SC}$ to control levels, 1 $\mu$M thapsigargin was added to stimulate increased intracellular calcium. The expected increase in $\Delta I_{SC}$ was observed with thapsigargin treated control cells, whereas $\Delta I_{SC}$ was attenuated in cells receiving prolonged treatment with carbachol. Pretreatment with D,L-1,2-cyclohexylidene-Ins(3,4,5,6)$P_4$/AM reversed the inhibitory effect of carbachol on calcium-mediated chloride ion secretion. Thus, D,L-1,2-cyclohexylidene-Ins(3,4, 5,6)$P_4$/AM functions as an antagonist of Ins(3,4,5,6)$P_4$.

Figure 5B:
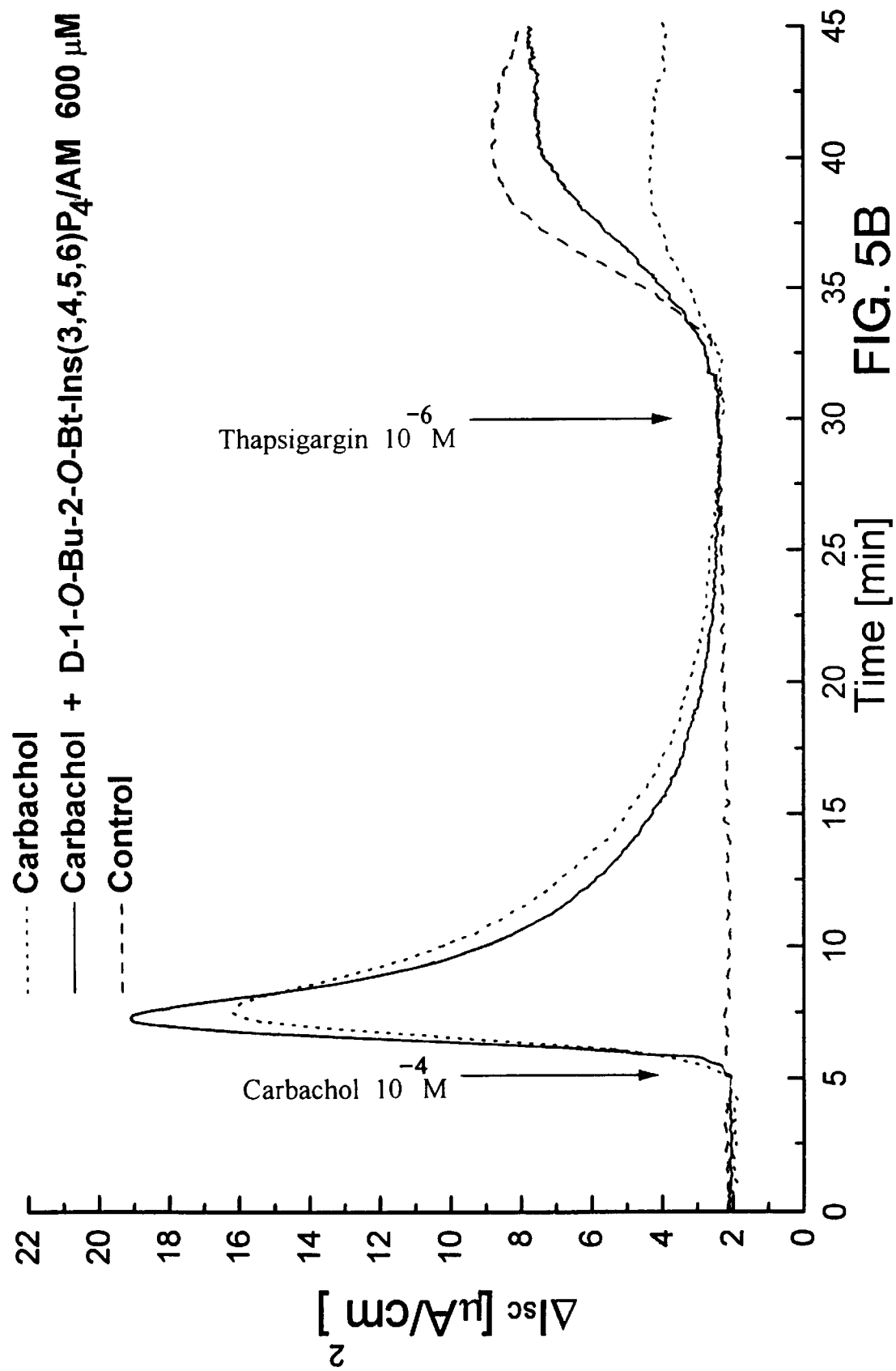
Figure 5E:
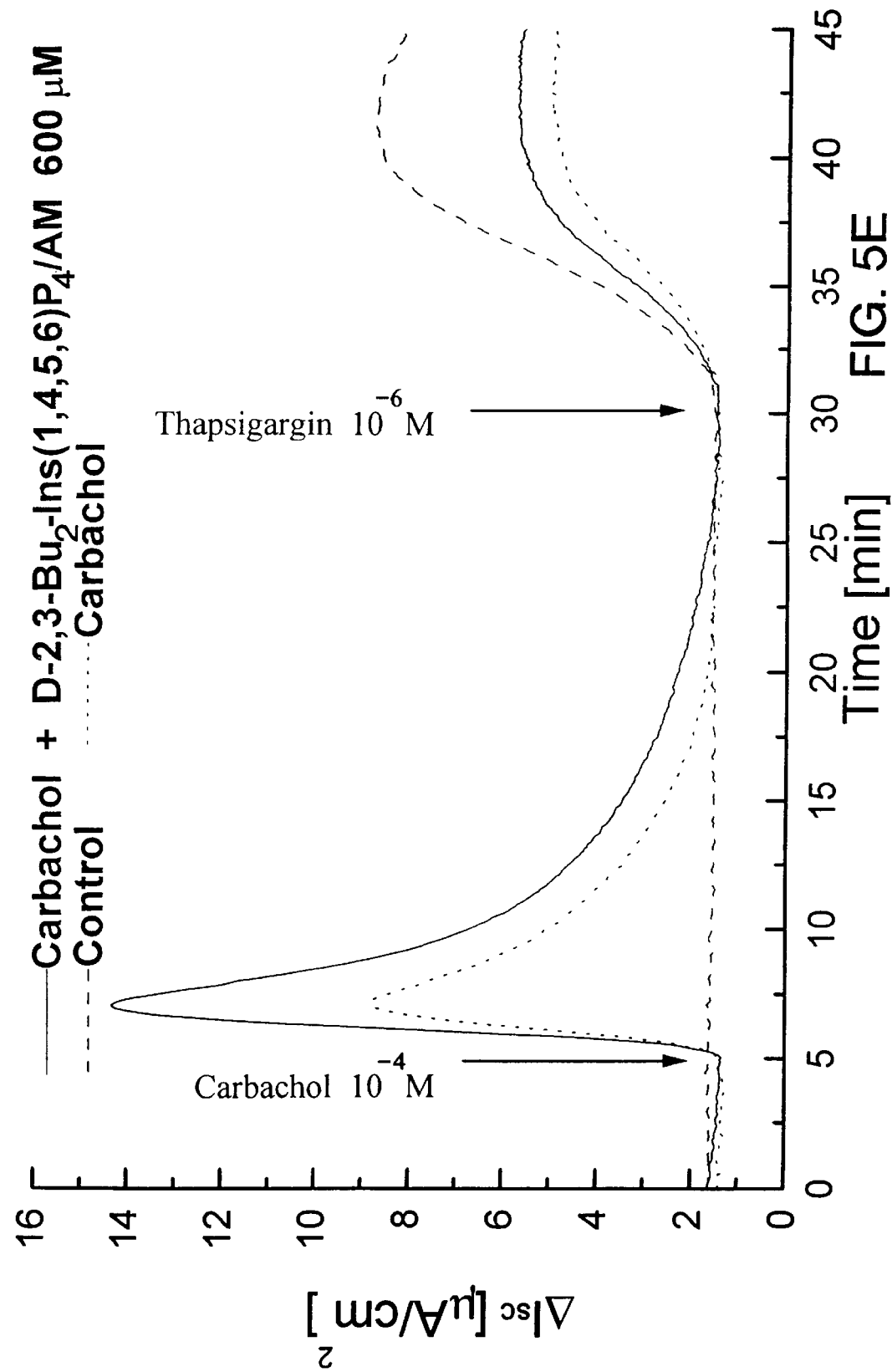
Figure 5F:
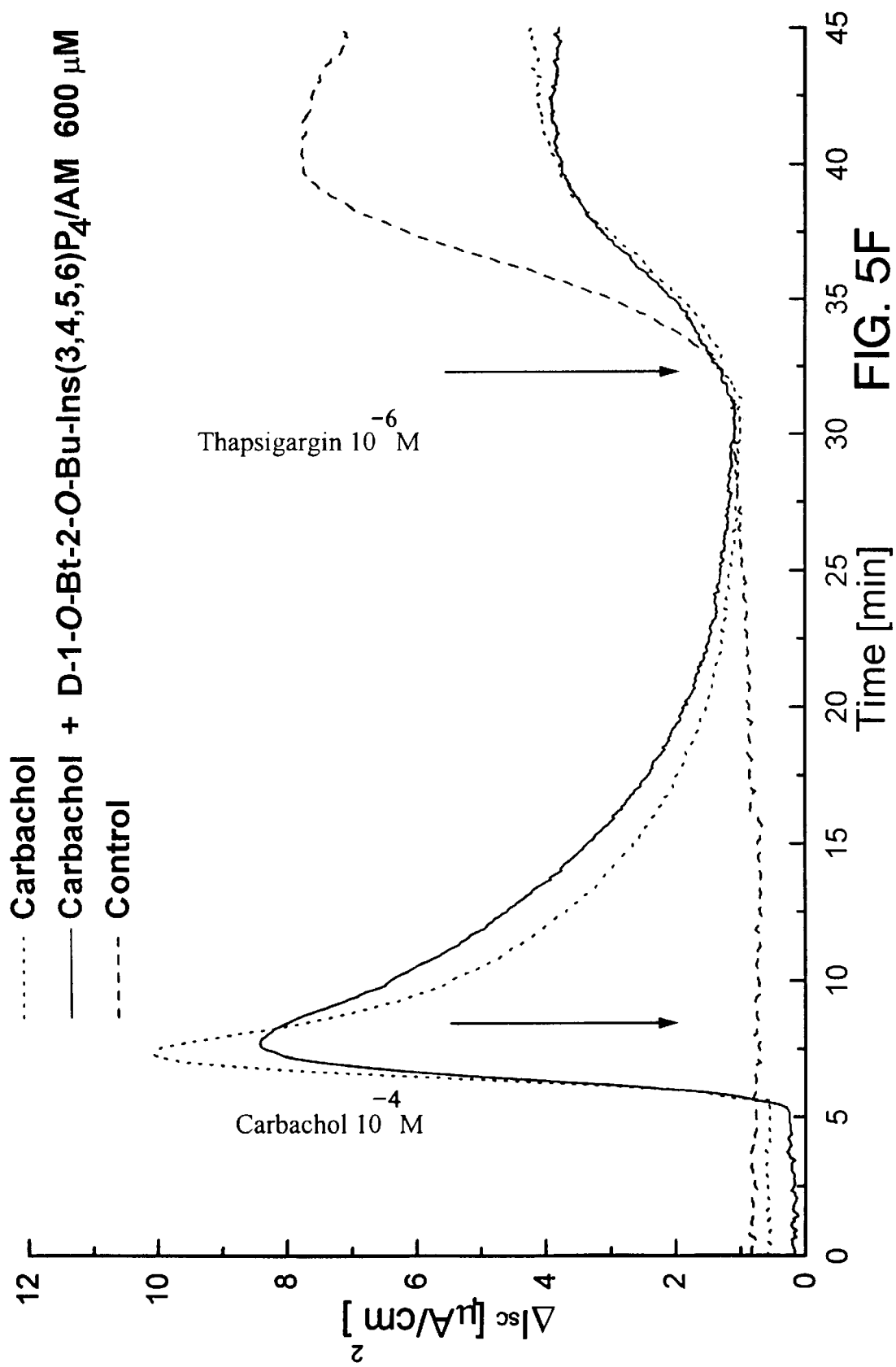
Figure 5G:
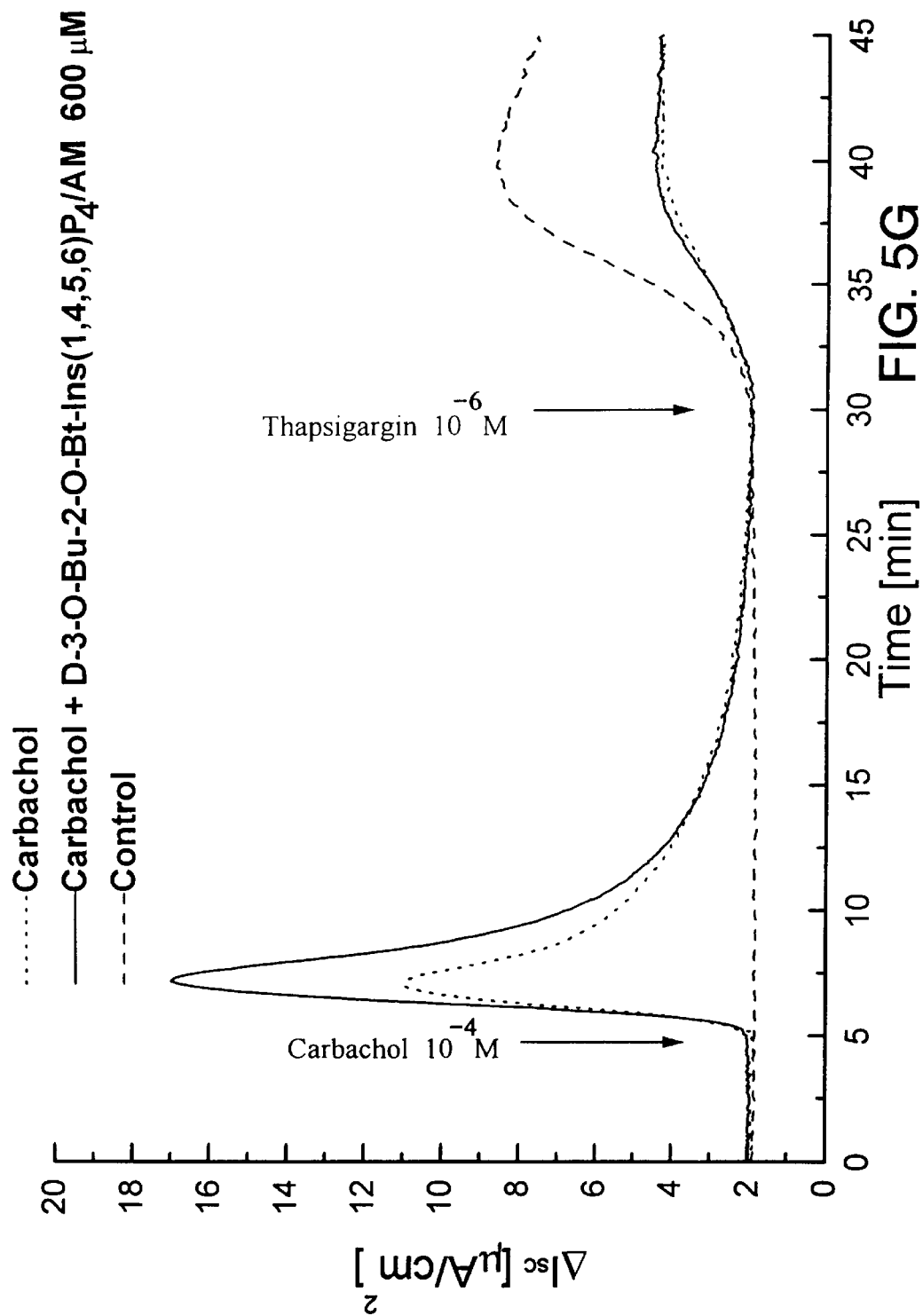

As shown in FIG. 5, the Ins(3,4,5,6)$P_4$ derivatives, D,L-1,2-cyclohexylidene-Ins(3,4,5,6)$P_4$/AM, 1-Bu-2-Bt-Ins(3,4, 5,6)$P_4$/AM and $Bu_2$-Ins(3,4,5,6)$P_4$/AM, reversed the carbachol-mediated inhibition of chloride ion secretion stimulated by thapsigargin, indicating that these Ins(3,4,5, 6)$P_4$ derivatives function as antagonists of Ins(3,4,5,6)$P_4$ (FIG. 5A to 5C, respectively). In contrast, the 1-Bt-2-Bu-Ins(3,4,5,6)$P_4$/AM as well as 3-Bt-2-Bu-Ins(1,4,5,6)$P_4$/AM, 2,3-$Bu_2$-Ins(1,4,5,6)$P_4$/AM and 3-Bu-2-Bt-Ins(1,4,5,6)$P_4$/AM did not reverse carbachol-mediated inhibition of chloride ion secretion stimulated by thapsigargin (FIG. 5D to 5G, respectively).

These results demonstrate that cell permeable derivatives of Ins(3,4,5,6)$P_4$ reverse the inhibitory effect of prolonged treatment with carbachol on calcium-mediated chloride ion secretion and, therefore, function as antagonists of Ins(3,4, 5,6)$P_4$.

EXAMPLE V

Elevation of Intracellular Ins(1,3,4)$P_3$ Levels Increases Ins(3,4,5,6)$P_4$ and Decreases Calcium-mediated Chloride Ion Secretion This example demonstrates that treatment of cells with a cell permeable derivative of Ins(1,3,4)$P_3$ increases Ins(3,4, 5,6)$P_4$, thereby decreasing calcium-mediated chloride ion secretion.

Almost 30 inositol polyphosphates have been identified in cells. Ins(1,3,4,5)$P_4$ is converted to Ins(1,3,4)$P_3$ by a 5' inositol polyphosphate phosphatase. In an in vitro assay system, Ins(1,3,4)$P_3$ inhibited inositol 1 kinase, which catalyzes the conversion of Ins(3,4,5,6)$P_4$ to Ins(1,3,4,5,6)$P_5$ (Tan et al., *J. Biol. Chem.* 272:2285 (1997)), which is incorporated herein by reference.

The cell permeable derivative D,L-$Bt_3$-Ins(1,3,4)$P_3$/AM was synthesized. Colonic epithelial $T_{84}$ cells were preincubated for 30 min with 400 $\mu$M D,L-$Bt_3$-Ins(1,3,4)$P_3$/AM prior to mounting in Ussing chambers and measuring $\Delta I_{SC}$. At 10 min, carbachol ($10^{-4}$ M) was added to transiently stimulate calcium-mediated chloride ion secretion. Data were the average of 8 experiments with p<0.04, unpaired, two-sided student's t-test.

Incubation of cells with 400 $\mu$M D,L-$Bt_3$-Ins(1,3,4)$P_3$/AM caused a three-fold increase in Ins(3,4,5,6)$P_4$ measured in cells labeled with ($^3$H)-inositol, indicating that Ins(1,3,4) $P_3$ increased Ins(3,4,5,6)$P_4$ in vivo. Control cells, which were preincubated with vehicle had a peak $\Delta I_{SC}$ of 15.2±2.8.

Cells preincubated with D,L-$Bt_3$-Ins(1,3,4)$P_3$/AM had a peak $\Delta I_{SC}$ of 7.9±1.6. Thus, calcium-mediated chloride ion secretion was decreased approximately 50% by treating cells with the cell permeable D,L-$Bt_3$-Ins(1,3,4)$P_3$/AM derivative.

These results demonstrate that cell permeable Ins(1,3,4) $P_3$ derivatives can increase the intracellular concentration of Ins(3,4,5,6)$P_4$, resulting in decreased calcium-mediated chloride ion secretion and, therefore, function as agonists of Ins(3,4,5,6)$P_4$.

EXAMPLE VI

Salmonella Invasion of Human Colonic Epithelial Cells Increases the Intracellular Concentration of Ins(1,4,5,6)$P_4$ This example demonstrates that invasion of human colonic epithelial cells by Salmonella increases concentrations of intracellular Ins(1,4,5,6)$P_4$.

Invasive enteric bacteria enter and penetrate the intestinal epithelium to gain access to the underlying mucosa and initiate systemic infection. Previous studies showing that Salmonella invasion of epithelial cells caused an increase in inositol polyphosphate turnover indicated that inositol polyphosphates could play a role in the response of epithelial cells to bacterial invasion (Ruschkowski et al., *FEMS Microbiol. Lett.* 74:121 (1992)). To characterize changes in inositol polyphosphates induced by bacterial invasion, the effect of invading bacteria on colonic epithelial cells was assessed.

Confluent colonic epithelial $T_{84}$ cells in 6 well plates were incubated for 4 days with 50 $\mu$Ci/well of ($^3$H)-inositol in inositol-free 50% Dulbecco's modified Eagle's (DME) medium and 50% Ham's F12 media supplemented with 5% dialyzed newborn calf serum. Cultures were washed three times with prewarmed medium (50% DME, 50% Ham3 s F12 and 1 mg/ml bovine serum albumin) and infected with $5 \times 10^8$ bacteria/well in the same media for various periods of time. Cultures were washed twice with ice-cold phosphate buffered saline (PBS) and lysed for 5 min on ice in 10% trichloroacetic acid and 10 mM phytic acid. Extracts were neutralized using FREON/alamine and resolved on an Adsorbosphere SAX column to separate the ($^3$H)-inositol polyphosphates. Radioactive peaks were quantitated as described previously using an HPLC equipped with an on-line radioactivity detector (Kachintorn et al., supra, 1993). To quantitate enantiomers unresolved on HPLC, the peak corresponding to ($^3$H)-Ins(3,4,5,6)$P_4$ and Ins(1,4,5,6) $P_4$ was separated from all other ($^3$H)-Ins$P_4$ isomers by HPLC, desalted, then incubated with partially purified Ins (1,4,5,6)$P_4$ 3-kinase with an internal standard of ($^{32}$P)-labeled Ins(1,4,5,6)$P_4$ as described previously (Vajanaphanich et al., supra, 1994). By comparing the relative amounts of ($^3$H)- and ($^{32}$P)-labeled Ins(1,3,4,5,6)$P_5$ formed, the ratio of ($^3$H)-Ins(3,4,5,6)$P_4$ to ($^3$H)-Ins(1,4,5,6) $P_4$ in the original peak was determined.

Monolayers of $T_{84}$ cells were labeled with ($^3$H)-inositol and infected for varying periods of time with *Salmonella dublin*. During the 60 min period immediately following infection, there were no significant changes in the levels of myo-inositol hexakisphosphate (Ins$P_6$) or other inositol polyphosphates such as Ins(1,4,5)$P_3$ that typically accumulate when phospholipase C is activated. In contrast, levels of unresolved enantiomers ($^3$H)-Ins(3,4,5,6)$P_4$ and ($^3$H)-Ins(1, 4,5,6)$P_4$ increased within 10 minutes after infection with S. dublin. Approximately 85% of this peak corresponded to ($^3$H)-Ins(1,4,5,6)$P_4$. A maximum 14-fold increase over control uninfected cells was reached 30–40 minutes after infection (see Table IV). Levels of ($^3$H)-Ins(1,4,5,6)P$_4$ decreased slowly after 40 min and returned to near baseline by 3 h after infection (see Table IV). Similar observations were made using another human intestinal epithelial cell line, LS174T. ($^3$H)-Ins(1,4,5,6)P$_4$ was found to increase 11.3-fold after *S. dublin* infection, indicating that the changes in cellular inositol polyphosphates after infection represent a general response of epithelial cells.

Infection of T$_{84}$ cells with another invasive Salmonella strain, *Salmonella typhi* BRD691, also increased ($^3$H)-Ins (1,4,5,6)P$_4$ levels (see Table IV). In contrast, a mutant strain of *S. dublin*, SB133, that attaches normally to epithelial cells but does not invade them, increased ($^3$H)-Ins(1,4,5,6)P$_4$ levels only minimally, indicating that invasion of host cells by Salmonella was required for this response. However, bacterial invasion alone was not sufficient to increase Ins(1, 4,5,6)P$_4$ levels, since infection of T$_{84}$ cells with several other invasive gram negative bacteria, including *Shigella flexneri*, *Shigella dysenteriae*, *Yersinia enterocolitica* and enteroinvasive *Escherichia coli* (serotype O29:NM), caused only small increases in ($^3$H)-Ins(1,4,5,6)P$_4$ levels. Furthermore, addition of non-invasive gram negative bacteria such as enterohemorrhagic *E. coli* (serotype O157) or a non-pathogenic *E. coli* (DH5α) to T$_{84}$ monolayers had little effect on ($^3$H)-Ins(1,4,5,6)P$_4$ levels. Addition of 10 μg/ml bacterial lipopolysaccharide (LPS) had no effect on ($^3$H)-Ins(1,4,5,6)P$_4$ levels.

TABLE IV

Increase in Ins(1,4,5,6)P$_4$ Levels after Salmonella Infection of Epithelial Cells

| Bacteria Added | Time after | ($^3$H)-(1,4,5,6)P$_4$ levels (Ratio Infected/Control) | n |
|---|---|---|---|
| *Salmonella dublin* lane | 30 | 13.9 ± 0.8 | 4 |
| *Salmonella dublin* lane | 60 | 10.3 ± 1.3 | 5 |
| *Salmonella dublin* lane | 420 | 3.6 | 2 |
| *Salmonella dublin* lane | 180 | 1.9 | 2 |
| *Salmonella typhi* BRD691 | 30 | 10.5 | 2 |
| *Salmonella dublin* SB133 (invA) | 30 | 1.9 ± 0.1 | 3 |
| *Shigella flexneri* | 60 | 1.9 | 2 |
| *Shigella dysenteriae* | 60 | 2.3 | 2 |
| *Yersinia enterocolitica* | 60 | 2.6 ± 0.1 | 3 |
| *Escherichia coli* O29:NM | 60 | 2.0 ± 0.1 | 5 |
| *Escherichia coli* O157 | 60 | 2.3 ± 0.2 | 4 |
| *Escherichia coli* DH5α | 60 | 2.1 ± 0.2 | 4 |
| LPS | 60 | 1.0 | 2 |

These results demonstrate that invasion of colonic epithelial cells with Salmonella increases the intracellular concentration of Ins(1,4,5,6)P$_4$. Increased chloride ion secretion occurs in secretory diarrhea, a pathological manifestation of Salmonella infection, suggesting a correlation with Ins(1,4,5,6)P$_4$ concentrations.

EXAMPLE VII

Ins(1,4,5,6)P$_4$ Reverses EGF-Induced Inhibition of Chloride Ion Secretion

This example demonstrates that increasing the intracellular concentration of Ins(1,4,5,6)P$_4$ by incubating cells with a cell permeable Ins(3,4,5,6)P$_4$ derivative reverses inhibition of chloride ion secretion induced by epidermal growth factor (EGF).

In Examples III and IV above, Ins(1,4,5,6)P$_4$ derivatives had no effect on the Ins(3,4,5,6)P$_4$-mediated decrease in chloride ion secretion. To test whether Ins(1,4,5,6)P$_4$ affects EGF induced inhibition of chloride ion secretion, T$_{84}$ cell monolayers were preincubated for 30 min with Bt$_2$Ins(1,4,5,6)P$_4$/AM. Measurement of $\Delta I_{SC}$ was initiated (see Example I) and, after 5 min of measurements, 16.3 nM EGF was added to the basolateral surface of the cells. After an additional 15 min incubation, 100 μM carbachol was added to acutely elevate intracellular calcium concentrations. Controls also were stimulated with carbachol but were not pretreated with EGF. Data are the means of duplicate measurements from a representative experiment (total of three experiments).

Figure 6:
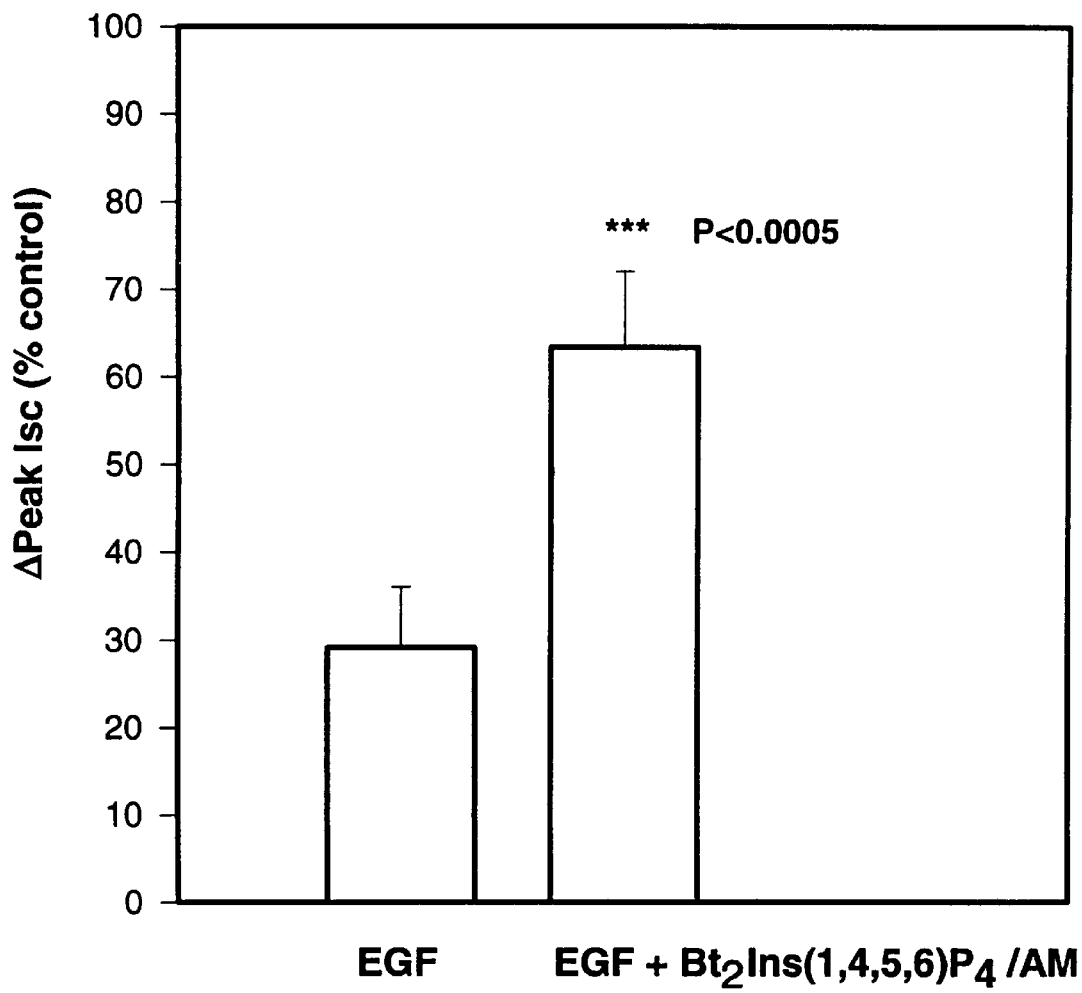
FIG. 6 shows enhanced chloride ion secretion in colonic epithelial $T_{84}$ cells treated with $Bt_2$-Ins(1,4,5,6)$P_4$/AM due to reversal of EGF-mediated inhibition of chloride ion secretion.

As shown in FIG. 6 and FIG. 7 (panels a and b), EGF inhibited carbachol stimulated chloride ion secretion. Preincubation with Bt$_2$Ins(1,4,5,6)P$_4$/AM, a cell permeable derivative that is hydrolyzed to Ins(1,4,5,6)P$_4$ by endogenous cellular esterases, significantly reversed EGF induced inhibition of chloride ion secretion. In contrast, the inhibitory function of EGF was not attenuated by addition of a cell permeable derivative of Ins(1,3,4,5,6)P$_5$ (FIG. 7, panel C). Addition of a cell permeable Ins(3,4,5,6)P$_4$ derivative, the enantiomer of Ins(1,4,5,6)P$_4$, also did not attenuate EGF inhibitory function on chloride ion secretion. Addition of Bt$_2$Ins(1,4,5,6)P$_4$/AM did not reverse EGF inhibition of cyclic AMP-mediated chloride ion secretion, indicating that the action of Ins(1,4,5,6)P$_4$ was specific for calcium-mediated chloride ion secretion.

These results demonstrate that increased levels of Ins(1,4,5,6)P$_4$, delivered to cells as a cell permeable derivative, enhances calcium-mediated chloride ion secretion by reversing EGF-mediated inhibition of chloride ion secretion.

EXAMPLE VIII

Ins(1,4,5,6)P$_4$ Reverses PtdInsP$_3$ Decreases in Calcium-mediated Chloride Ion Secretion This example demonstrates that a cell permeable derivative of PtdInsP$_3$ decreases calcium-mediated chloride ion secretion. A cell permeable Ins(1,4,5,6)P$_4$ derivative reverses the PtdInsP$_3$-mediated decrease in chloride ion secretion.

Figure 8:
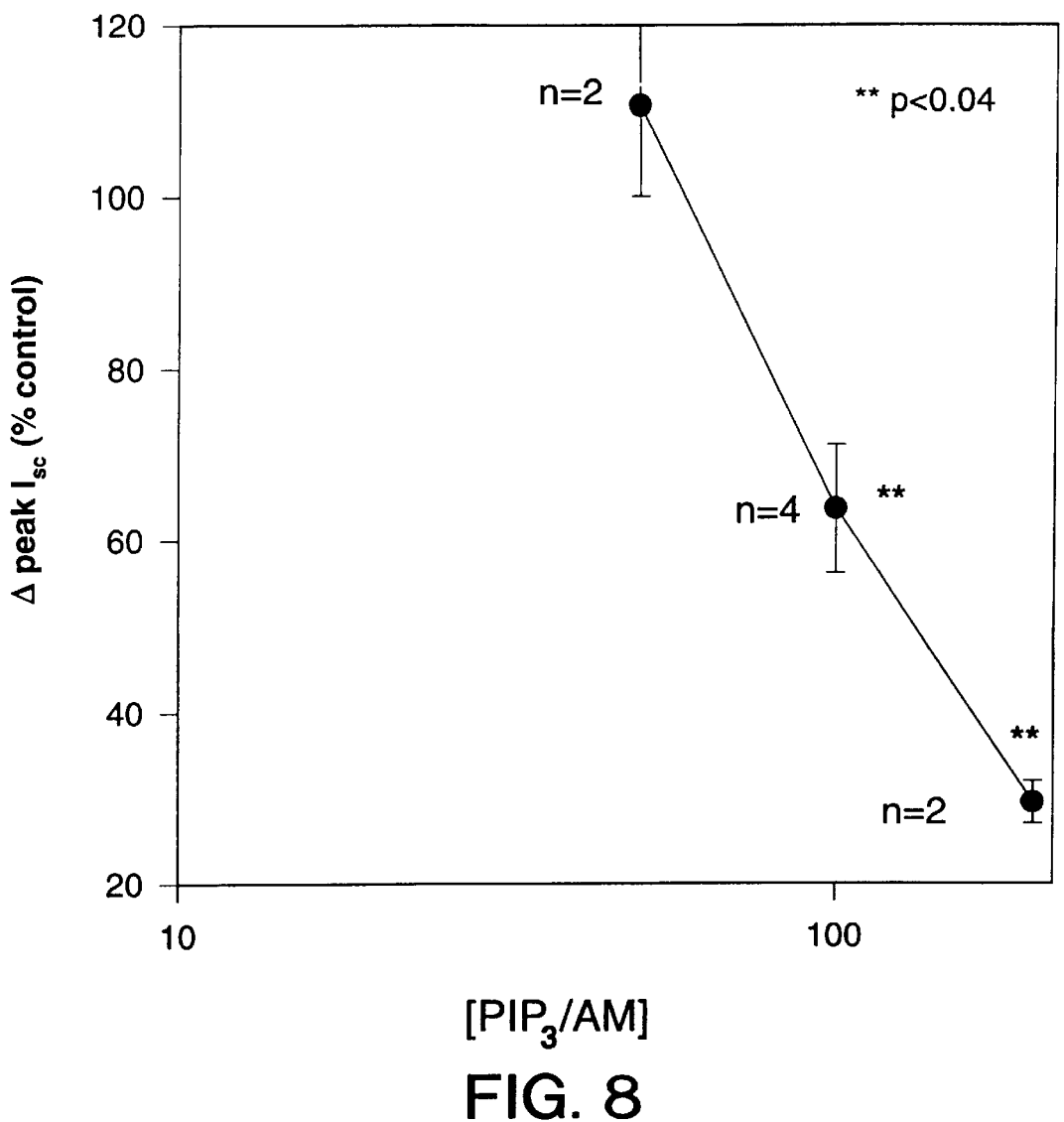
FIG. 8 shows decreased chloride ion secretion in colonic epithelial $T_{84}$ cells treated with increasing concentrations of PtdInsP$_3$/AM.

T$_{84}$ cell monolayers were preincubated for 30 min with PtdInsP$_3$/AM and $\Delta I_{SC}$ was measured. As shown in FIG. 8, increasing concentrations of PtdInsP$_3$/AM inhibited carbachol-stimulated chloride ion secretion, indicating that an inositol polyphosphate distinct from Ins(3,4,5,6)P$_4$ also inhibits calcium-mediated chloride ion secretion.

Additional cell permeable derivatives of the PI 3-kinase product PtdInsP$_3$ were synthesized and tested for the effect on chloride ion secretion. Cells were preincubated with diC$_{16}$-Bt-PtdInsP$_3$/AM or diC$_8$-Bt-PtdInsP$_3$/AM and $\Delta I_{SC}$ was measured as described in Example VII.

As shown in FIG. 7, pretreatment of T$_{84}$ cells with diC$_{16}$-Bt-PtdInsP$_3$/AM (FIG. 7d) inhibited calcium-mediated chloride ion secretion by up to 74%. Similarly, diC$_8$-BtPtdInsP$_3$/AM inhibited chloride ion secretion by 79%. No inhibition of calcium-mediated chloride ion secretion was observed when cells were pretreated with PtdInsP$_3$, which is not expected to enter cells. These cell permeable derivatives of PtdInsP$_3$ had no effect on calcium levels after carbachol stimulation. The level of decrease observed with these derivatives of PtdInsP$_3$ was comparable to that observed with EGF treatment of cells. Furthermore, addition of EGF to monolayers preincubated with cell permeable PtdInsP$_3$ derivatives did not result in additional inhibition of calcium-mediated chloride ion secretion, indicating that PtdInsP$_3$ and EGF function through the same mechanism.

Figure 7A:
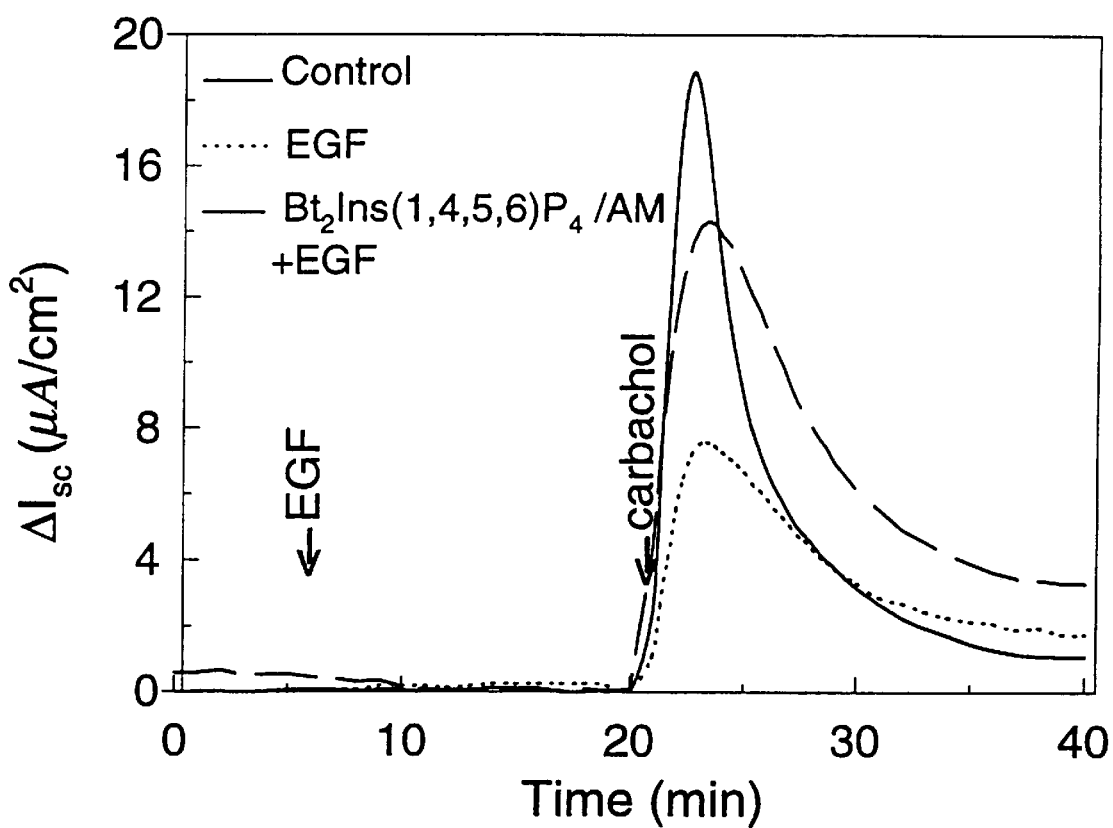
FIG. 7 shows decreased chloride ion secretion in colonic epithelial $T_{84}$ cells treated with EGF or treated with cell permeable derivatives of PtdInsP$_3$. $Bt_2$-Ins(1,4,5,6)$P_4$/AM enhances chloride ion secretion due to reversal of EGF- and PtdInsP$_3$-mediated inhibition of chloride ion secretion.
Figure 7B:
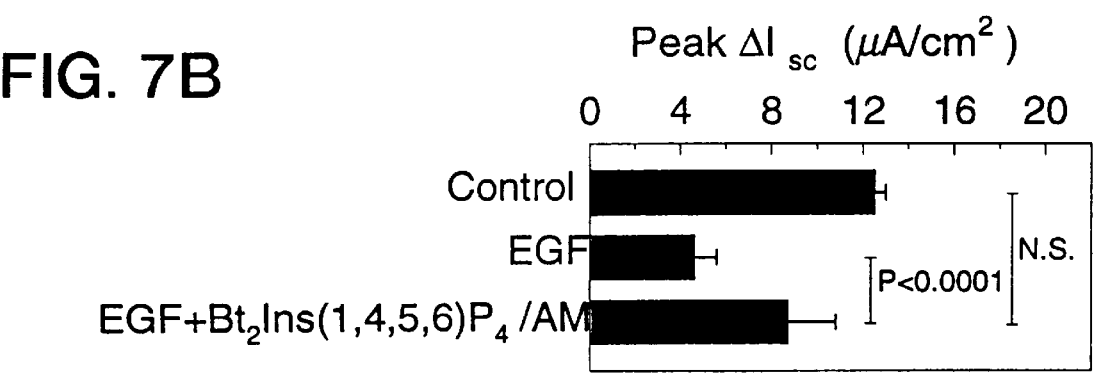
Figure 7C:
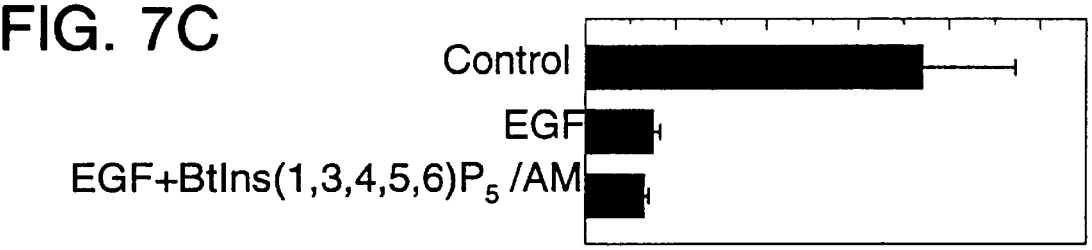
Figure 7D:
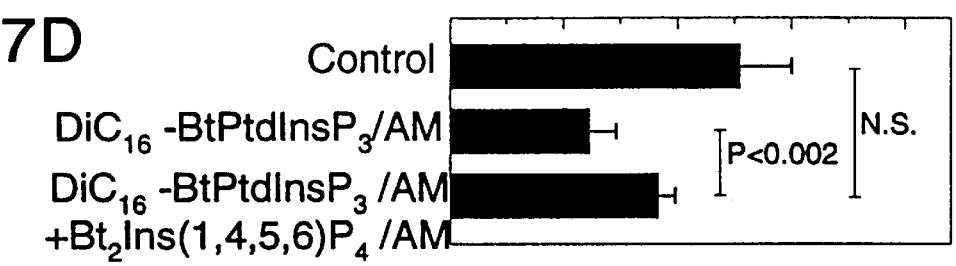

$T_{84}$ cells also were preincubated with cell permeable Ins(1,4,5,6)$P_4$ derivatives to determine whether Ins(1,4,5,6)$P_4$ can reverse PtdInsP$_3$-mediated decreases in chloride ion secretion. As shown in FIG. 7d, preincubation of $T_{84}$ monolayers with membrane-permeable Ins(1,4,5,6)$P_4$ derivatives partially reversed PtdInsP$_3$-mediated decreases in chloride ion secretion.

These results demonstrate that PtdInsP$_3$ decreases calcium-mediated chloride ion secretion. In addition, Ins(1,4,5,6)$P_4$ reverses PtdInsP$_3$ decreases in calcium-mediated chloride ion secretion.

EXAMPLE IX

Chloride Ion Transport in Human Nasal Epithelia

This example provides a primary human nasal epithelial cell system useful as a model for examining the effectiveness of compounds to alter chloride ion secretion in respiratory epithelia.

Primary human nasal epithelia are obtained by biopsy. For bioelectric and calcium measurement in monolayers, primary human nasal epithelial cells are plated on porous Transwell Coll filters (pore diameter, 0.4 μM; Costar) affixed to O-rings and studied 5–7 days after seeding, a time coincident with the development of maximal transepithelial potential difference. Cells are maintained in serum-free Hams' F12 medium supplemented with insulin (10 μg/ml), transferrin (5 μg/ml), endothelial cell growth supplement (3.75 μg/ml), hydrocortisone (5 nM), endothelial cell growth supplement (3.75 μg/ml), triiodothyronine (30 nM) and 1 mM CaCl$_2$. Human nasal epithelial monolayers are mounted in miniature Ussing chambers, 5–7 days after plating.

Transepithelial potential difference is monitored by a Voltage-Clamp/Pulse Generator (Physiologic Instruments, San Diego, Calif.) and the bioelectrics recorded on a two channel recorder. Monolayers are exposed to sodium free Ringers to calculate changes in transepithelial chloride resistance, a measure of the change from its native sodium absorptive state to a chloride ion secretory state. For intracellular calcium measurements, monolayers are loaded with Fura-2 and mounted over an objective of a microscope coupled to a microfluorimeter. The fluorescence intensity ratio is collected either from a field of 30–40 cells or from a single cell. ΔISC to intracellular calcium levels are normalized in each preparation. To ensure that the results reflect response from true monolayers, monolayers are routinely fixed and cross-sectional segments examined.

Primary human nasal epithelial cells are useful for treating with antagonists of Ins(3,4,5,6)$P_4$ and PtdInsP$_3$, such as those described in Examples III, IV, VII and VIII. Compounds effective at enhancing chloride ion secretion in primary human nasal epithelia are good candidates for alleviating symptoms of cystic fibrosis such as pulmonary insufficiency.

EXAMPLE X

Generation of CFTR$^-$ $T_{84}$ Cells

This example provides a method for preparing CFTR$^-$ $T_{84}$ cells, which are useful as a model of cystic fibrosis.

To screen Ins(3,4,5,6)$P_4$ derivatives and to ultimately determine if the CFTR regulates the expression of elements involved in Ins(3,4,5,6)$P_4$-mediated inhibition of chloride ion secretion, CFTR$^-$ $T_{84}$ cells are generated.

The CFTR gene(s) in $T_{84}$ cells are inactivated using a double selection approach, originally developed to generate gene knockout mutations in mouse embryonic stems cells (ES cells) (Mansour et al., *Nature* 336:348 (1988)), which is incorporated herein by reference. Mutagenic CFTR gene targeting constructs are generated in pSSC-9 vector (Chauhan and Gottesman, *Gene* 120:281 (1992)), which is incorporated herein by reference. This vector carries the neomycin resistance gene, driven by a thymidine kinase promoter, flanked on both sides by the hsv-tk genes. In addition, pSSC-9 carries convenient cloning sites on both sides of the gene, which can be used to insert gene targeting segments, and two Sfil restriction sites, which can be used to excise the mutagenic cassette in a linear form. Selection for the expression of the neomycin gene, by resistance to G418, allows screening for stably transfected clones. Subsequent selection against hsv-tk expression, using cyclovir, expands the clones in which the construct integrated via homologous recombination into the targeted site (Mansour et al., supra, 1988). An 8.5 kb fragment of the CFTR gene (TE 2611E8.5, containing exon 21) is used as a source of CFTR gene sequences (Rommens et al., *Science* 245:1059 (1989); and Rommens et al., *Am. J. Hum. Genet.* 45:932 (1989)), each of which is incorporated herein by reference. Alternatively, the polymerase chain reaction (PCR) can be used to directly clone appropriate sequences from $T_{84}$ cells. Several PCR primers for amplification of CFTR gene segments have been described (Zielinski et al., *Genomics* 10:214 (1991)), which is incorporated herein by reference. Fragments at least 2–4 kb long should be amplified to ensure sufficient sequence homology for homologous recombination. PCR primers carry restriction site extensions compatible with pSSC-9 cloning sites.

Mutagenic constructs are transfected into $T_{84}$ cells, using DNA transfection methods, for example, calcium phosphate or electroporation-based protocols (*Molecular Biology. A Laboratory Manual*, 2nd ed., Sambrook et al., Eds., Cold Spring Harbor Laboratory Press, Plainview, N.Y. (1989)), which is incorporated herein by reference. Stable transfectants are selected using G418, expanded and subjected to the second round of selection using cyclovir. Resistant clones, presumably derived by homologous recombination of the vector into the CFTR locus, are subjected to an additional round of selection, using increasing amounts of G418. This approach, developed to facilitate generation of double knockout mutants in mice using ES cells, can be also applied for selection of homozygous mutations in cell lines (Chen et al., *Proc. Natl. Acad. Sci. USA* 90:4528 (1993); and Mortenson, *Hypertension* 22:646 (1993)), each of which is incorporated herein by reference. Selected clones are analyzed by Southern blot and PCR analyses to verify that the neo cassette was inserted into the CFTR gene(s).

A "double construct method" can alternatively be used in which the mutagenesis of target genes is performed sequentially, using two different mutagenic constructs (Mortenson, supra, 1993; Feldhaus et al., *EMBO J.* 12:2763 (1993); and Porter and Itzhaki, *Eur. J. Biochem.* 218:273 (1993)), each of which is incorporated herein by reference. These constructs carry a neo gene or a gpt gene cassette, allowing for sequential transfection and selection of the neo gene using G418 and selection of the gpt gene using mycophenolic acid plus xanthine. Double knockout CFTR mutants of $T_{84}$ cells are used to assess the efficacy of Ins(3,4,5,6)$P_4$ and PtdInsP$_3$ antagonists.

These results demonstrate the generation of a CFTR$^-$ mutant of $T_{84}$ cells, which can be used as a model of cystic fibrosis. These cells provide a genetic background similar to that found in epithelial cells of cystic fibrosis patients. Antagonists of Ins(3,4,5,6)$P_4$ and PtdInsP$_3$, which effectively enhance chloride ion secretion in CFTR⁻ T$_{84}$ cells, are good candidates for enhancing chloride ion secretion in cystic fibrosis patients.

EXAMPLE XI

Preparation of Cell Permeable Inositol Polyphosphate Derivatives

This example describes the synthesis of cell permeable inositol polyphosphate derivatives.

The synthetic reactions for some cell permeable inositol polyphosphate derivatives were described previously (Roemer et al., supra, 1996; and Roemer et al., supra, 1995).

Figure 9:
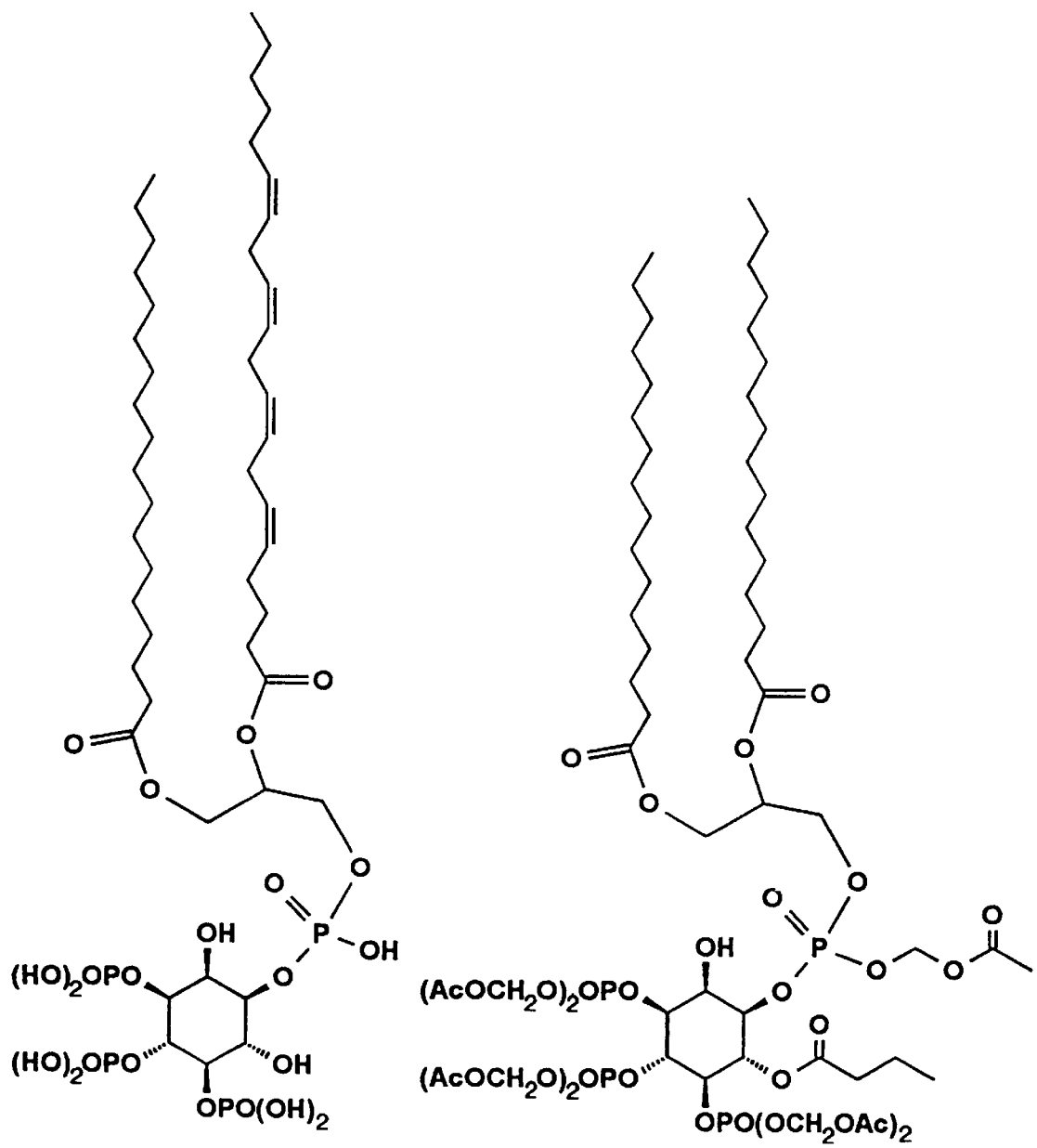
FIG. 9 shows the structure of cell permeable PtdInsP$_3$ and diC$_{16}$-Bt-PtdInsP$_3$/AM.
Figure 10A:
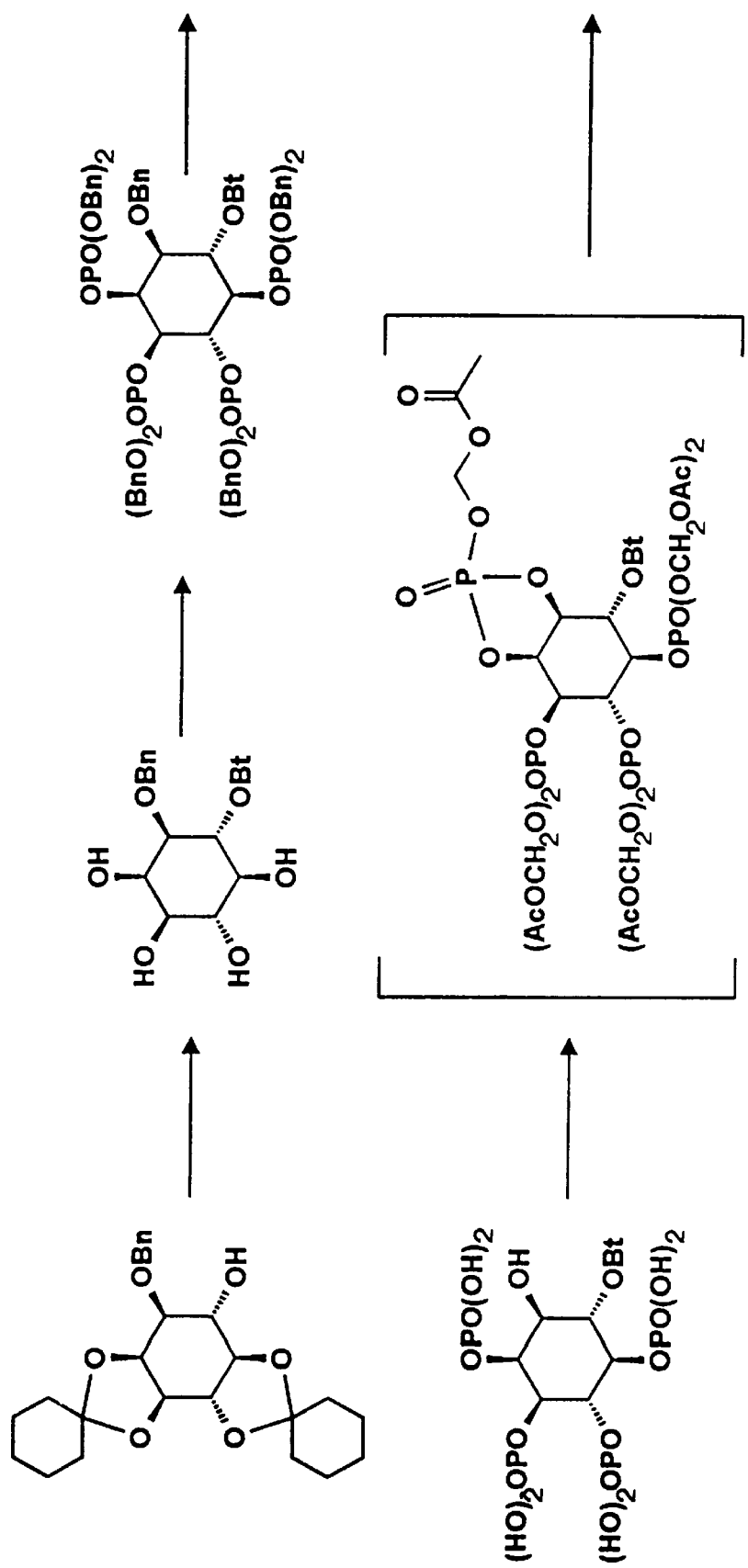
FIG. 10 shows a schematic of the synthesis of cell permeable PtdInsP$_3$/AM derivatives.
Figure 10B:
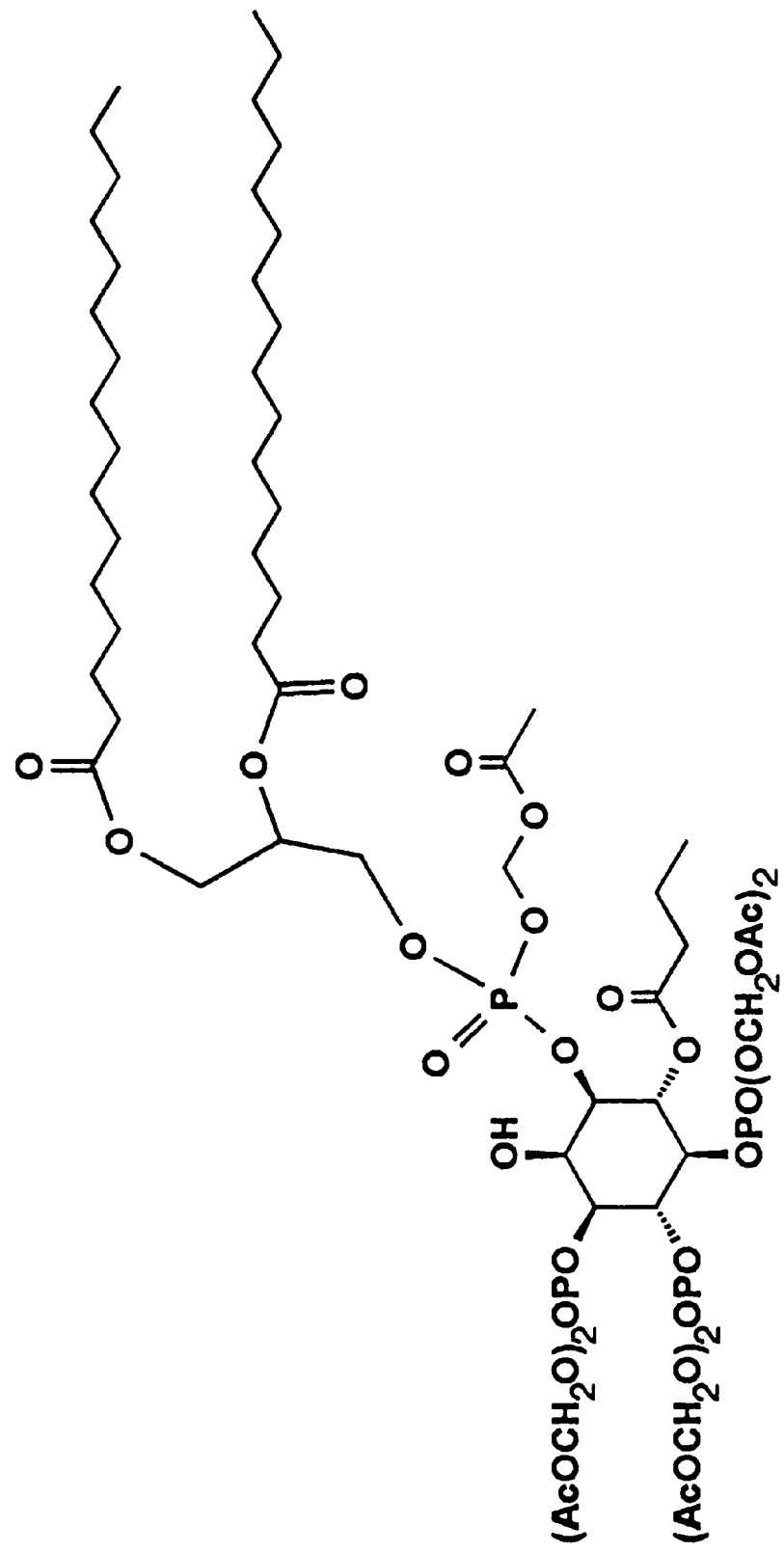
Figure 11:
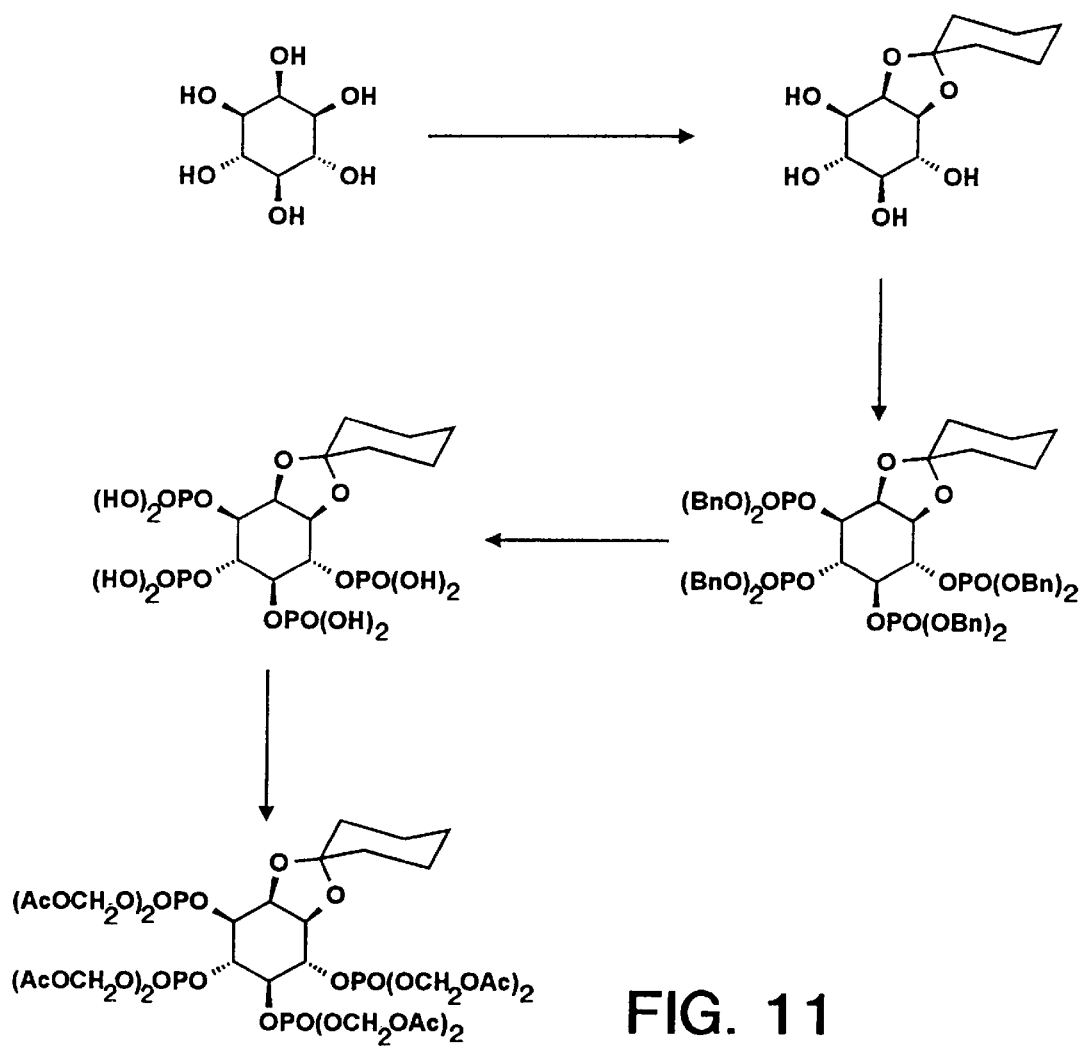
FIG. 11 shows a schematic of the synthesis of 1,2-cyclohexylidene-Ins(3,4,5,6)$P_4$ //AM.
Figure 12:
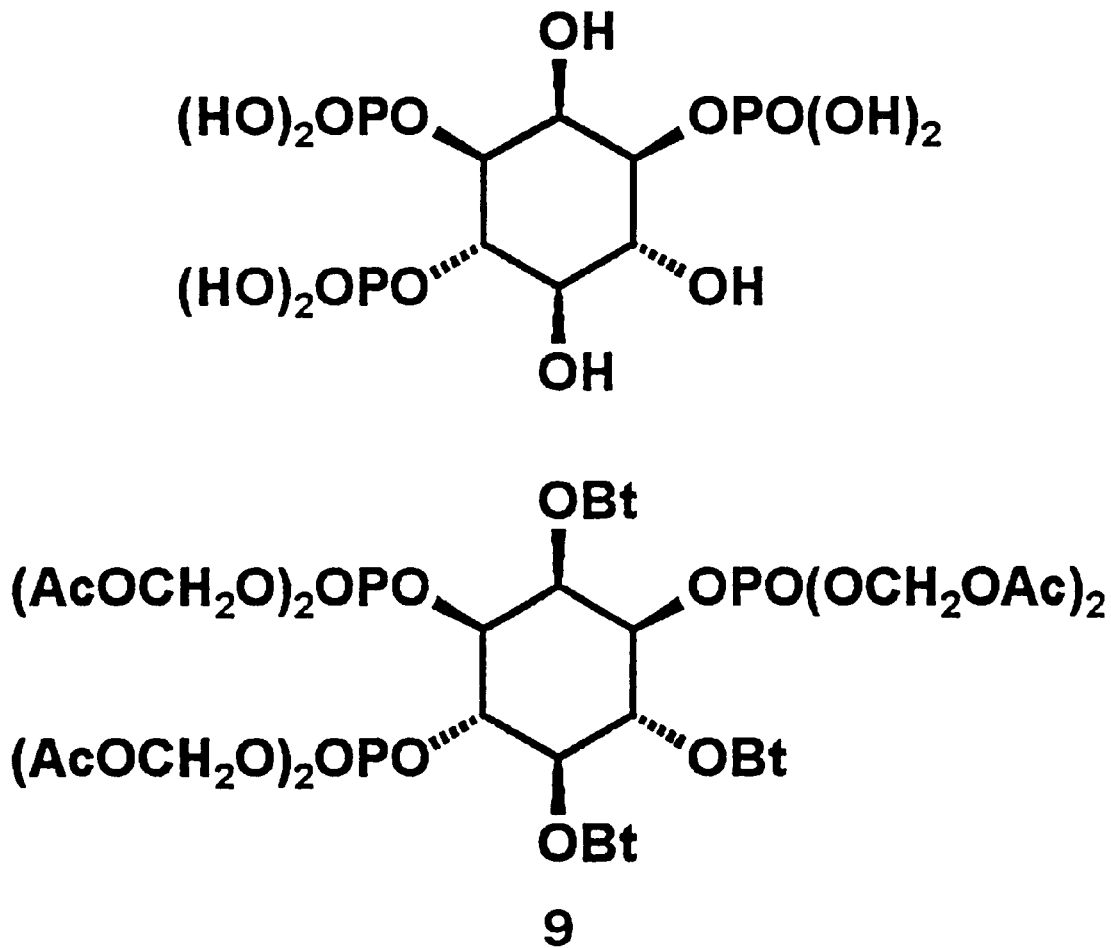
FIG. 12 shows structures of myo-inositol 1,3,4-trisphosphate and 2,5,6-Bt$_3$-Ins(1,3,4)P$_3$/AM. Only the D-configuration of the compounds is shown.
Figure 13:
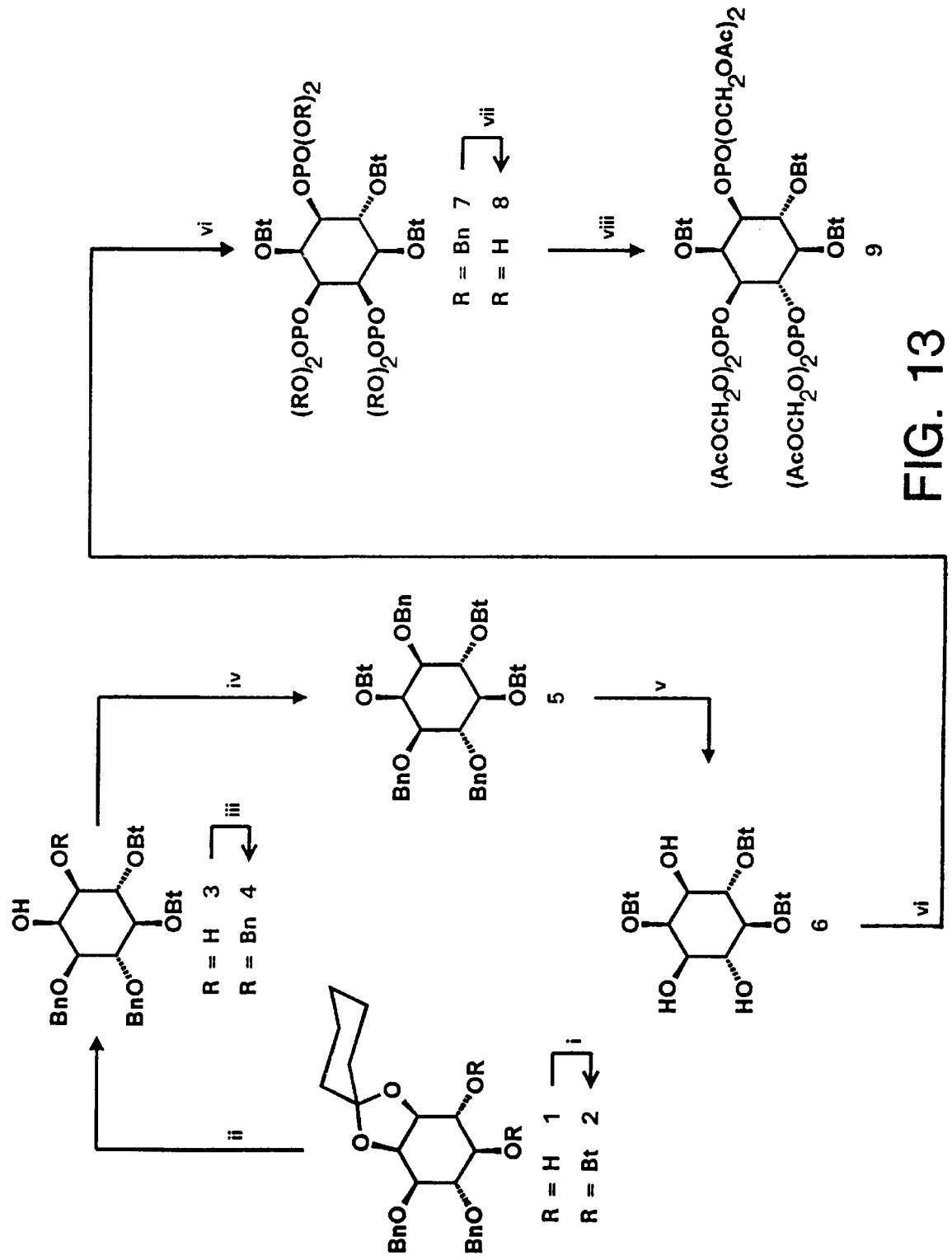
FIG. 13 shows a schematic for synthesis of cell permeable inositol polyphosphate derivatives.

The synthetic reactions of additional inositol polyphosphate derivatives are described below. FIG. 9 shows the structure of cell permeable PtdInsP$_3$ and diC$_{16}$-Bt-PtdInsP$_3$/AM. FIG. 10 shows a schematic of the synthesis of PtdInsP$_3$/AM derivatives. FIG. 11 shows a schematic of the synthesis of 1,2-cyclohexylidene-Ins(3,4,5,6)P$_4$//AM. FIG. 12 shows structures of myo-inositol 1,3,4-trisphosphate and 2,5,6-Bt$_3$-Ins(1,3,4)P$_3$/AM. Only the D-configuration of the compounds is shown. FIG. 13 shows a schematic for synthesis of cell permeable inositol polyphosphate derivatives. In FIG. 13, the following conditions were used: (i) Bt$_2$O, DMAP, pyr.; (ii) TFA, CH$_3$CN/H$_2$O; (iii) a Bu$_2$SnO, toluene, refl., b BnBr, CsF, DMF; (iv) Bt$_2$O, DMAP, pyr., v Pd/C (10%), AcOH; (vi) a (BnO)$_2$PNiPr$_2$, tetrazole, CH$_3$CN, b AcOOOH, −40° C.; (vii) Pd/C (10%), AcOH; and (viii) AMBr, DIEA, CH$_3$CN.

All chemical reagents were obtained in the highest purity available. Where necessary, solvents were dried and/or distilled before use. Acetonitrile was distilled from phosphorus (V) oxide and stored over 3 Å molecular sieves, as was dimethylformamide (DMF). Pyridine and toluene were stored over 4 Å molecular sieves Ethyl-diisopropylamine (DIEA) was dried over sodium wire. Palladium on charcoal (10%) and trifluoroacetic acid were from Acros Chemie. Dibenzyl N, N-diisopropylphosphoramidite, peracetic acid (32% v/w), tetrazole, sodium hydride and acetoxymethyl bromide were from Aldrich. Milwaukee, Wis. Butyric anhydride, DIEA and tris(triphenylphosphin)-rhodium (I)-chloride were from Merck Benzyl bromide, allyl bromide, butyl iodide, cesium fluoride and 4-dimethylamino pyridine (DMAP) were from Fluka. The ion-exchange resin Dowex 50 WX 8, H⁺-form, was from Serva, Heidelberg Germany. All other reagents were from Riedel-de Haën.

High performance liquid chromatography (HPLC) was performed on a LDC/Milton Roy Consta Metric III pump with a LDC/Milton Roy UV Monitor D (254 nm) or a Knaur refractive index detector. The analytical column was a Merck Hibar steel tube (250 mm×4 mm) filled with RP 18 material (Merck, LiChrosorb:10 μm). Preparative HPLC was performed using a Shimadzu LC 8A pump with a preparative LDC UV III Monitor (254 nm) or a Knaur refractive index detector and a Merck Prepbar steel column (25° mm×50 mm) filled with RP 18 material (Merck, LiChrospher 100, 10 μm). The eluents were methanol-water mixtures; composition are given in % methanol (MeOH).

$^1$H-NMR and $^{31}$P-NMR spectra were recorded on a Brucker AM 360 μM spectrometer Chemical shifts were measured in ppm relative to tetramethylsilane for $^1$H NMR spectra and external 85% H$_3$PO$_4$ for $^{31}$P NMR spectra. J-values are given in Hz. Mass spectra were recorded using a Finnigan Mat 8222 mass spectrometer with fast atom bombardment (FAB) ionization. High resolution masses were determined relative to known compounds with a mass not differing more than 10%. Melting points (MP) (uncorrected) were determined using a Büchi B-540 apparatus. Optical rotations were measured at the sodium D-line in a 10 cm cell with a Perkin-Elmer 1231 polarimeter. Ultrafiltration of the palladium/charcoal catalyst was performed with a Sartorius filtration apparatus SM 162 01 using filters from regenerated cellulose (Sartorius, SM 116 04)Sartorius Edgewood, N.Y. Element analysis were performed by Mikroanalytisches (Labor Beller, Gottingen, Germany).

D-1,4,5,6-tetra-O-benzyl-myo-inositol (ent-9) and D-3,4, 5,6-tetra-O-benzyl-myo-inositol (2) were synthesized as described before (Roemer et al., supra, 1996). The compound rac-1,2-Di-O-cyclohexylidene-myo-inositol was synthesized by the method of Angyal and Tate (Angyal and Tate, *J. Chem. Soc.* 1965:6949 (1965)), which is incorporated herein by reference.

General procedure for phosphorylation. The selectively protected myo-inositol derivative and tetrazole were dissolved under argon in dry acetonitrile before dibenzyl N,N-diisopropylphosphoramidite was added. After stirring at room temperature for the indicated time, the reaction mixture was cooled to −40° C. and peracetic acid (32% v/w; 1 mol equivalent for each mol equivalent of phosphoramidite) was added. After the mixture has reached room temperature the solvent was removed under reduced pressure and the residual oil was purified by preparative HPLC to give the desired inositol tetrakisphosphate derivative.

General procedure for removing the benzyl groups by hydrogenolysis. The fully protected myo-inositol tetrakisphosphate or the tetrabenzyl-inositol, respectively, in acetic acid were vigorously stirred with palladium on carbon (10%; 0.1 mol palladium for each mol of benzyl groups) under an hydrogen atmosphere in a self-built hydrogenation apparatus for the indicated time. The catalyst was removed by ultrafiltration and the filtrate was freeze dried to give the respective product.

General procedure for the introduction of acetoxymethyl esters. The thoroughly dried inositol tetrakisphosphate derivative (free acid) was suspended in dry acetonitrile under argon before dry DIEA (2.25 mol DIEA for each mol of hydroxy groups) and acetoxymethyl bromide (1 mol equivalent for each mol equivalent of DIEA) were added. After stirring of the mixture at room temperature in the dark for 4 days all volatile components were evaporated off under reduced pressure and the crude residue was purified by preparative HPLC with the solvent specified to give the inositol tetrakisphosphate octakis (acetoxymethyl) ester as a syrup.

D-3,4,5,6-Tetra-O benzyl-1-O-butyl-myo-inositol (10) Dry 9 (250 mg, 463 μmol) and dry dibutyltin oxide (116 mg, 167 μmol) were heated under reflux in dry toluene (100 ml) in a Soxhlet apparatus with activated molecular sieve (3 Å) for 18 h. The reaction mixture was cooled to room temperature and evaporated to dryness under diminished pressure. CsF (140 mg, 926 μmol) was added to the residual oil, and the mixture was kept under high vacuum for 2 h. The residual syrup was dissolved in dry DMF (10 ml) under argon and 1-butyl iodide (300 μl, 2.62 mmol) was added. After stirring the solution for 48 h, HPLC analysis (90% MeOH; 1.5 ml/min; t$_R$=7.43 min) showed no further reaction. Excess of 1-butyl iodide and DMF were removed in high vacuum. The crude product was chromatographed by preparative HPLC (93% MeOH; 40 ml/min; t$_R$=22.30 min) to give compound 10 (175 mg, 74%) as a solid. Mp: 75.4°–75.9° C. (from methanol). [∞]$^{24}$$_D$: +8.4° (c=0.98 in CHCl$_3$). $^1$H-NMR (CDCl$_3$, 360 MHZ): δ0.91 (3 H, t, J=7.25 Hz, CH$_3$), 1.34–1.44 (2 H, m, CH$_2$), 1.57–1.65 (2 H, m, CH$_2$), 2.46 (1 H, s (br), OH), 3.23 (1 H, dd, J=9.31, 2.33 Hz, H-1), 3.43 (1 H, dd, J=9.78, 2.80 Hz, H-3), 3.45 (1 H, dd, J=9.78, 9.31 Hz, H 4), 3.57 (1 H, dt, J=6.99, 6.52 Hz, OCCH$_2$CH$_2$CH$_3$), 3,57 (1 H, dt, J=6.99 Hz, OCCH$_2$CH$_2$CH$_3$), 3.91 (1H, dd, J=9.31, 9.31 Hz, H-5), 3.99 (1 H, dd, J=9.78, 9.31 Hz, H-6), 4.27 (1 H, dd, J=2.80, 2.33 Hz, H-2), 4.71–1.91 (8 H, m, CH$_2$Ph), 7.25–7.39 (20 H, m, CH$_2$Ph) MS: m/z (+ve ion FAB) 597 [(M+H)$^+$, 1], 91 [Bn$^-$, 100].

D-1,4,5,6-Tetra-O-benzyl-3-O-butyl-myo-inositol (ent-10). A similar reaction and work-up of the diol ent-9 gave compound ent-10. $[\alpha]^{24}_D$-8.7° (c=1.01 in CHCl$_3$). Spectral data were in accordance with those obtained for enantiomer 10.

D-3,4,5,6-Tetra-O-benzyl-1-O-butyl-2-O-butyryl-myo-inositol (11). A solution of 10 (178 mg, 298 μmol), butyric anhydride (210 μl, 596 μmol) and DMAP (38 mg, 30 μmol) in dry pyridine (3 ml) was stirred at room temperature for 18 h. The solvents were evaporated under high vacuum to give an oil. Residual pyridine was removed by evaporating three times with octane. The residue was dissolved in tert-butyl methyl ether (10 ml) and was washed once with phosphate buffer (10 ml), once with sodium hydrogen carbonate (10 ml), once with sodium hydrogen sulfate (10 ml), once again with phosphate buffer (10 ml) and then with brine (10 ml). The organic layer was dried over Na$_2$SO$_4$ and filtered. Evaporation of the solvent gave pure 11 (194 mg, 98%) as an oil, $[\alpha]^{24}_D$: −10.4° (c-1.97 in CHCl$_3$). $^1$H-NMR (CHCl$_3$, 360 MHZ) δ 0,91 (3 H, t, J=7.25 Hz, CH$_3$), 0.98 (3 H, t, J=7.46 Hz, CH$_3$), 1.32–1.42 (2 H, m, CH$_2$), 1.50–1.60 (2 H, m, CH$_2$), 1.69 (2 H, tq, J=7.46, 7.46 Hz, O(O)CCH$_2$CH$_2$CH$_3$), 2.39 (2H, t, J=7.46 Hz, O(O)CCH$_2$, CH$_2$CH$_3$,), 3.31 (1 H, dd, J=9.66, 2.63 Hz, H-1), 3.44 (1 H, dt, J=9.07, 6.81 Hz, OCH$_2$CH$_2$CH$_2$CH$_3$), 3.48 (1 H, dd, J=9.66, 3.07 Hz, H 3), 3.49 (1 H, dd, J=9.66, 9.22 Hz, H-5), 3.67 (1 H dt, J=8.78, 6.81 Hz, OCH$_2$CH$_2$CH$_2$CH$_3$), 3.81 (1 H, dd, J=9.66, 9.66 Hz, H-4), 3.86 (1 H, dd J=9.66, 9.22 Hz, H-6), 4.51–4.93 (8H, m, CH$_2$Ph), 5.83 (1 H,dd, J=3.07, 2.63 Hz, H-2), 7.26–7.36 (20 H, m, CH$_2$Ph). MS: m/z (+ve ion FAB) 665 [(M+H)$^+$, 21], 91 [Bn$^+$, 100].

D-1,4,5,6-Tetra-O-benzyl-3-O-butyl-2-O-butyryl-myo-inositol (ent-11). Compound ent-10 was butyrylated as described above for the other enantiomer to give compound ent-11. $[\alpha]^{24}_D$: +10.7° (c-2.05 in CHCl$_3$). Spectral data were in accordance with those of enantiomer 11.

D-1-O-Butyl-2-O-butyryl-myo-inositol (12). Compound 11 (178 mg, 267 μmol) was hydrogenated palladium (10%) on carbon under hydrogen as described in the general procedure to give tetrol 12 (81 mg, 99%) as a solid after freeze-drying. $[\alpha]^{24}_D$: +26.5° (c=2.0 in MeOH). $^1$H NMR ([D$_6$]DMSO, 360 MHZ): δ 0.84 (3 H, t, J=7.38 Hz, CH$_3$), 0.90(3 H, t, J=7.38 Hz, CH$_3$), 1.21–1.31 (2 H, m, CH$_2$), 1.36–1.44 (2 H, m, CH$_2$), 1.54 (2 H, tq, J=7.38, 700 Hz, O(O)CCH$_2$,CH$_2$CH$_3$), 2.24 (2 H, t, J=7.00 Hz, O(O)CCH$_2$, CH$_2$CH$_3$), 2.97 (1 H, dd, J-8.94, 8.55 Hz, H-5), 3.10 (1 H, dd, J=9.72, 2.72 Hz, H-1), 3.25–3.35 (4 H, m, H-3, H-4, H-6, OCH$_2$ CH$_2$CH$_3$), 3.50 (1 H, dt, J=8.94, 6.60 Hz, OCH$_2$CH$_2$ CH$_2$CH$_3$), 4.85 (4 H, s (br), OH), 5.36 (1 H dd, J=2.72, 2.33 Hz, H-2). MS: m/z (+ve ion FAB) 307 [(M+H)$^+$, 21], 71 [Bt+, 100]. MS: m/z (−ve ion FAB) 305 [(M−H$^+$)$^-$, 27], 87 [B+O$^-$, 100]. Anal. ( ) C: calculated, 54.89; found 54 45; H: calculated, 8.55, found 8.56.

D-3-O-Butyl-2-O-butyl-2-O-Butyryl-myo-inositol (ent-12). A similar reaction and work-up of the fully protected compound ent-11 afforded tetrol ent-12 $[\alpha]^{24}_D$: −26.6° (c=0.76 in MeOH). Spectral data were in accordance with those obtained for enantiomer 12.

D-1-O-butyryl-myo-inositol 3,4,5,6-tetrakis (dibenzyl) phosphate (20). A solution of tetrol 12 (63 mg 206 μmol) and tetrazole (174 mg, 2.47 mmol) in acetonitrile (2 ml) was treated with dibenzyl N, N-diisopropylphosphoramidite (834 μl, 2.47 mmol) for 18 h., oxidized with peracetic acid, and worked up as described. Purification by preparative HPLC (93% MeOH; 40 ml/min; t$_R$=26.45 min) gave compound 20 (165 mg, 60%) as an oil. $[\alpha]^{24}_D$: −4.9° (c=1.08 in CHCl$_3$). $^1$H-NMR (CDCl$_3$, 360 MHZ): δ 0.77 (3 H, t, J=7.27 Hz, CH$_3$), 0.93 (3 H, t, J=7.27 Hz, CH$_3$), 1.12–1.21 (2 H, m, CH$_2$), 1.31–1.46 (2 H, m, CH$_2$), 1.62 (2 H tq, J=7.26, 7.26 Hz, O(O)CCH$_2$CH$_2$CH$_3$), 2.24 (2 H, t J=7.26 Hz, O(O)CCH$_2$CH$_2$CH$_3$), 3.26 (1, H, dt, J=8.23, 5.81 Hz, OCH$_2$CH$_2$CH$_2$CH$_3$), 3.37 (1 H, dd, J=9,20, 2.90 Hz, H-1), 3.44 (1 H, dt, J=8.23, 7.26 Hz, OCH$_2$CH$_2$CH$_2$CH$_3$), 4.35 (1 H, ddd, J=9.69, 9.69, 2.42 Hz, H-3), 4.53 (1 H, ddd, J=9.69, 9.69, 9.69 Hz, H-5), 4.68 (1 H, ddd, J=9.69, 9.69, 9.20 Hz, H-6), 4.91 (1 H, ddd J=9.84, 9.69, 9.69 Hz, H-4), 4.92–5.02 (16 H, m, CH$_2$Ph), 5.91 (1 H, dd, J=2.90, 2.42 Hz, H-2), 7.11–7.30 (40 H, m, CH$_2$Ph), $^{31}$P NMR (CDCl$_3$, $^1$H decoupled, 145.8 MHZ): δ−1.81 (1 P, s), −1.18 (1 P, s), −0.72 (1 P, s), −0.66 (1 P, s). MS. m/z (+ve ion FAB) 1347 [(M+H)$^+$, 8]; 91 [Bn$^+$, 100].

D-3-O-Butyl-2-O-butyryl-myo-inositol 1,4,5,6-tetrakis (dibenzyl) phosphate (ent-20). Tetrol ent-12 was phosphitylated and oxidized as described above for compound 20 to give the fully protected phosphate ent-20. $[\alpha]^{24}_D$: +4.8° (c=2.09 in CHCl$_3$). Spectral data were in accordance with those obtained for enantiomer 20.

D-1-O-Butyl-2-O-butyryl-myo-inositol 3,4,5,6-tetrakis phosphate (21). Compound 20 (160 mg, 118 μmol) was hydrogenated with palladium (10%) on carbon as described in the general procedure to give title compound 21 (73 mg, 99%) as a solid after freeze-drying. $[\alpha]^{24}_D$: 4.1° (c=1.04 in H$_2$O, pH 1.6). $^1$H NMR (D$_2$O, 360 MHZ). δ 0.81 (3 H, t, J=7.30 Hz, CH$_3$). 0.91 (3 H, t, J-7.30 Hz, CH$_3$), 1.22–1.30 (2 H, m, CH$_2$), 1.42–1.49 (2 H, m CH$_2$), 1.62 (2 H, tq, J=7.30, 7.30 Hz, O(O)CCH$_2$CH$_2$CH$_3$), 2.36, 2.54 (2 H, m, O(O)CCH$_2$CH$_2$CH$_3$), 3.56 (1 H, dt, J=9.49, 6.46 Hz, OCH$_2$CH$_2$CH$_2$CH$_3$), 3.63 (1 H, dt, J=9.36, 6.74 Hz, OCH$_2$CH$_2$CH$_2$CH$_3$), 3.70 (1 H, dd, J=9.74, 2.62 Hz , H-1), 4.27 (1 H, ddd, J=9.36, 9.36, 9.36 Hz, H-5), 4.31 (1 H, ddd, J=9.74, 9,74, 2.25 Hz, H-3), 4.39 (I H, ddd, J=9.74, 9,36, 9.36 Hz, H-6), 4.49 (1 H, ddd, J-9.74, 9.36, 9.00 Hz, H-4), 5.75 (1 H, dd, J=2.62, 2.25 Hz, H-2), $^{31}$P NMR (D$_2$O, $^1$H decoupled, 145.8 MHZ): δ−0.10 (2 P, s), 0.50(1 P. s). 0.80 (1 P, s). MS: m/z (+ve ion FAB) 627 [(M+H)$^+$, 4], 71 [Bt$^+$, 100]. MS: m/z (−ve ion FAB) 625 [(M−H$^+$) 100].

D-3-O-Butyl-2-O-butyryl-myo-inositol 1,4,5,6-tetrakisphosphate (ent-21). A similar reaction with the fully protected substrate ent-20 afforded the free acid ent-21 after freeze drying $[\alpha]^{24}_D$: =4.1° (c=0.78 in H$_2$O, pH 1.6). Spectral data were in accordance with those obtained for enantiomer 21.

D-1-O-Butyl-myo-inositol 3,4,5,6-tetrakisphosphate (5). Compound 21 (17 mg, 27 μmol) was treated with 1 M KOH (260 μl) to adjust the pH value to 12.8. The solution was stirred at room temperature for 2 days. The reaction mixture was directly poured onto an ion-exchange column (Dowex 50 WX 8, Ht) for purification. Lyophilization gave compound 5 (14 mg, 94%)—$[\alpha]^{24}_D$: +4.9° (c=0.53 in H$_2$O, pH 1.6). $^1$H NMR (D$_2$O, 360 MHZ): δ 0.78 (3 H t, J=7.44 Hz, CH$_3$), 1.26 (2 H, tq, J=7.44, 7.44 Hz, CH$_2$), 1.43–1.52 (2H, m, $CH_2$), 3.42 (1 H, dd, J=9.60, 2.78 Hz, H-1), 3.52 (1 H, dt, J=9.71, 6.74 Hz, $OCH_2CH_2CH_2CH_3$) 3.59 (1 H, dt, J=9.81, 6.74 Hz, $OCH_2CH_2CH_2CH_3$) 4.16 (1 H, ddd, J=9.60, 9.60, 2.78 Hz, H-3) 4.21 (1 H, ddd, J=9.37, 9.37, 9.37 Hz, H-5), 4.35 (1H, dd, J=2.78, 2.78 Hz, H-2), 4.39 (1H, ddd, J=9.60, 9.60, 9.37 Hz, H-6), 4.60 (1 H, ddd, J-9.60, 9.60, 9.37 Hz, H-4), $^{31}$P NMR ($D_2O$, $^1$H decoupled, 145.8 MHZ): δ 0.10 (2P, s), 0.70 (1P, s), 1.05 (1P, s) MS:m/z (−ve ion FAB) 555 [(M−H$^+$), 100].

D-3-O-Butyl-myo-inositol 1,4,5,6-tetrakisphosphate (ent-5). The butyryl groups of substrate ent-21 were hydrolyzed by the same method described above to give the tetrakisphosphate ent-5—[α]$^{24}_D$: +4.6° (c=0.35 in $H_2O$, pH 1.6). Spectral data were in accordance with those obtained for enantiomer 5.

D-1-O-Butyl-2-O-butyryl-myo-inositol 3,4,5,6-tetrakisphosphate octakis(acetoxymethyl) ester (1). DIEA (131 μl, 768 μmol) and acetoxymethyl bromide (77 μl, 768 μmol) were added to a suspension of compound 21 (30 mg, 47 μmol) in acetonitrile (2 ml) as described in the general procedure. Purification by preparative HPLC (73% MeOH, 37.5 ml/min, $t_R$=19.30) gave compound 1 (31 mg, 55%) as a syrup. —[α]$^{24}_D$: +2.0° (c=1.00 in toluene). $^1$H NMR ([D]$_8$toluene, 360 MHZ): δ 0.85 (3 H, t, J-7.48 Hz, $CH_3$) 0.97 (3H, t, J=7.48 Hz, $CH_3$), 1.39 (2H, tq, J=7.48, 7.28 Hz, $CH_2$), 1.51–1.67 (4H, m, 2×$CH_2$) 1.75–1.75 (24 H, 8 s, 8×OAc), 2.08–2.13 (2 H, m, $CH_2$), 3.07 (1 H, dd, J-9.45, 2.76 Hz, H-1), 3.46 (1H, dt, J=7.68, 5.91 Hz, $OCH_2CH_2CH_2CH_3$), 3.62 (1 H, dt, J=7.74, 7.68 Hz, $OCH_2CH_2CH_2CH_3$), 4.62 (1H, ddd, J=9.84, 9.84, 2.76 Hz, H-3), 4.67 (1 H, ddd, J=9.84, 9.84, 9.45 Hz, H-5), 4.80 (1H, ddd, J=9.45, 9.45, 9.16 Hz, H-6) 5.04 (1H, ddd, J-9.84, 9.84, 9.45 Hz, H-4), 5.63–5.96 (16 H, m, $CH_2OAc$), 6.00 (1 H, dd, J=2.76, 2.76 Hz, H-2). $^{31}$P NMR ([D]$_8$-toluene, $^1$H decoupled, 145.8 MHZ): δ−5.14 (1 P, s), −4.49 (1P, s), −4.06 (1P, s), −3.99 (1 P, s), MS:m/z (+ve ion FAB) 1131 [(M-$CH_2OAc^+$+2H)$^+$, 58], 98.7 [((M-3 $CH_2OAc^+$+4H), 100], MS:m/z (−ve ion FAB) 1129 [(M-$CH_2OAc^+$)$^−$, 38], 241 [OP($OCH_2OAc$)$^−_2$, 100].

D-3-O-Butyl-2-O-butyryl-myo-inositol 1,4,5,6-tetrakisphosphate octakis(acetoxymethyl)ester (ent-1). Alkylation of the phosphate ent-21 as described above afforded the octakis(acetoxymethyl) ester ent-1. [α]$^{24}_D$: +1.9° (c=1.46 in toluene). Special data were in accordance with those obtained for enantiomer 1.

D-1-O-Allyl-3,4,5,6-tetra-O-benzyl-myo-inositol(13). Dry 9 (690 mg, 1.28 mmol) and dry dibutyltin oxide (324 mg, 1.3 mmol) were heated under reflux in dry toluene (150 ml) in a Soxhlet apparatus with activated molecular sieve (3 Å) for 20 h. The reaction mixture was cooled to room temperature and evaporated to dryness under diminished pressure. CsF (388 mg, 2.56 mol) was added to the residual oil, and the mixture was kept under high vacuum for 2 h. The residual syrup was dissolved in dry DMF (10 ml) under argon and 1-allyl iodide (329 μl, 3.58 mmol) was added. After stirring the solution for 20 h, HPLC analysis (95% MeOH; 1.5 ml/min; $t_R$=3.20 min) showed no further reaction. Excess of 1-allyl iodide and DMF were removed in high vacuum. The crude product was chromatographed by preparative HPLC (90% MeOH; 40 ml/min; $t_R$=26.15 min) to give compound 13 (448 mg, 60%) as a solid. Mp: 71–72° C. (from methanol).—[α]$^{24}_D$: +4.6° (c=0.98 in CHCl$_3$). $^1$H NMR (CDCl$_3$, 360 MHZ): δ 3.30 (1H, dd, J-973, 3.10 Hz, H-1), 3.41 (1H, dd, J=9.73, 2.65, H-3), 3.44 (1H, dd, J=9.51, 9.51, H-5), 3.95 (1H, dd, J-9.73, 9.51 Hz, H-6), 3.99 (1H, dd, J=9.73, 2.51 Hz, H-4), 4.18 (1H, dd, J=1.65, 1.33 Hz, $OCH_2CHCH_2$), 4.19 (1H, dd, J=2.65, 1.33 Hz, $OCH_2CHCH_2$), 4.20 (1H, dd, J-3.10, 2.65 Hz, H-2), 4.71–4.92 (8H, m, $CH_2Ph$), 5.19 (1H, ddt, J=11.50, 1.33, 1.33 Hz, $OCH_2CHCH_2$), 5.29 (1H, ddt, J-16.91, 2.65, 1.33 Hz, $OCH_2CHCH_2$), 5.94 (1H, dddd, J=16.91, 11.50, 1.33, 1.33 Hz, $OCH_2CHCH_2$), 7.26–7.37 (20 H, m, $CH_2Ph$). MS:m/z (+ve ion FAB) 581[(M+H)$^+$, 1], 91 [Bn$^+$, 100]. MS:m/z (ve ion FAB) 580 [M−H$^+$)$^+$6] 489 [M−Bn$^+$)$^+$, 100].

D-3-O-Allyl-1,4,5,6-tetra-O-benzyl-myo-inositol (ent-13). A similar reaction and work-up of the diol ent-9 gave compound ent-13.—[α]$^{24}_D$: +3.9° (c=0.82 in CHCl$_3$). Spectral data were in accordance with those obtained for enantiomer 13.

D-1-O-Allyl-3,4,5,6-tetra-O-benzyl-2-O-butyl-myo-inositol (14). Sodium hydride (46 mg, 1.92 mmol) was added to a stirred solution of 13 (445 mg, 767 μmol) in dry DMF (5 ml) at room temperature in the dark. The mixture was stirred for 5 h, after which 1-butyl iodide (306 μl, 2.68 mmol) was added. The suspension was stirred for 18 h at 80° C., after HPLC (95% MeOH; 1.5 ml/min; $t_R$=7.35) showed a product. Excess of 1-butyl iodide and DMF were evaporated off under reduced pressure. The mixture was then dissolved in tert-butyl methyl ether (40 ml) and washed once with phosphate buffer (20 ml). aqueous. sodium dithionate (20 ml) and brine (20 ml) successively. The organic layer was dried over $Na_2SO_4$, filtered, and the ether was evaporated off to give an oil. The crude oil was purified by preparative HPLC (93% MeOH; 40 ml/min; $t_R$=37.10 min) to give the title compound 14 (458 mg, 94%) as an oil.—[α]$^{24}_D$: +1.5° (c=2.29 in CHCl$_3$). $^1$H NMR (CDCl$_3$, 360 MHZ); δ 0.95 (3 H, t, J=7.27 Hz, $CH_3$), 1.39–1.49 (2H, m, $CH_2$), 1.58–1.66 (2H, m, $CH_2$), 3.24 (1H, dd, J=9.69, 2.42 Hz, H-1), 3.36 (1H, dd, J=9.93, 2.42, H-3), 3.46 (1H, dd, J=9.45, 9.45, H-5), 3.78 (2H, t, J=6.54 Hz, $OCH_2CH_2CH_2CH_3$), 3.89 (1H, dd, J=2.42, 2.42 Hz, H-2), 3.98 (1H, dd, J-9.45, 9.45, H-6), 4.03 (1H, dd, J-9.45, 9.45 Hz, H-4), 4.15 (1H, dd, J-5.81, 1.00 Hz, $OCH_2CHCH_2$), 4.16 (1H, dd, J-6.06, 1.00 Hz, $OCH_2CHCH_2$), 4.72, 4.95 (8H, m, $CH_2Ph$), 5.19 (1H, ddt, J-10.66, 1.45, 1.45 Hz, $OCH_2CHCH_2$), 5.32 (1H, ddt, J-16.95, 1.45, 1.45 Hz, $OCH_2CHCH_2$), 5.95 (1H, dddd, J-16.95, 10.66, 1.45, 1.45 Hz, $OCH_2CHCH_2$), 7.26–7.40 (20 H, m, $CH_2Ph$). MS:m/z (+ve ion FAB) 637 [(M+H)$^+$, 1], 91 (Bn$^+$, 100].

D-3-O-Allyl-1,4,5,6-tetra-O-benzyl-2-O-butyl-myo-inositol (ent-14). A similar reaction and work-up of compound ent-13 gave compound ent-14. [α]$^{24}_D$: −1.6° (c=1.87 in CHCl$_3$). Spectral data were in accordance with those obtained for enantiomer 14.

D-3,4,5,6-Tetra-O-benzyl-2-O-butyl-myo-inositol (15). Tris(triphenylphosphin)-rhodium(I)-chloride (140 mg, 150 μmol) and DIEA (25 μl, 140 μmol) were added to a suspension of 14 (458 mg, 720 μmol) in 50% ethanol (90 ml), before the suspension was heated under reflux for 7 h. The reaction mixture was cooled to room temperature before trifluoroacetic acid (7 ml) was added and the solution was stirred for an additional 24 h, after HPLC (90% MeOH; 1.5 ml/min; $t_R$=4.03 min) showed no starting material. After neutralization with aqueous. 2N $NH_4OH$ the ethanol was evaporated off under reduced pressure to give a syrup. The syrup was dissolved in tert-butyl methyl ether (40 ml) and washed once with phosphate buffer (20 ml) and brine (20 ml) successively. The organic layer was dried over $Na_2SO_4$, filtered, and the ether was evaporated off to give an oil. The crude oil was purified by preparative HPLC (92% MeOH; 40 ml/min; $t_R$=27.40 min) to give 15 (275 mg, 74%) as a solid.—[α]24$_D$: +24.6° (c=0.97 in CHCl$_3$). $^1$H NMR (CDCl$_3$, 360 MHZ): δ 0.92 (3H, t, J-7.36 Hz, $CH_3$), 1.32–1.43 (2H, m, CH$_2$), 1.53–1.61 (2H, m, CH$_2$), 3.41 (1H, dd, J=9.96, 2.60 Hz, H-1), 3.45 (1H, dd, J=9.52, 2.60 Hz, H-3), 3.46 (1H, dd, J=9.31, 9.31 Hz, H-5), 3.61 (1H, dt, J=9.09, 6.49 Hz, OCCH$_2$CH$_2$CH$_3$), 3.74 (1H, dd, J=9.52, 9.31 Hz, H-4), 3.86 (1H, dd, J=2.60, 2.60 Hz, H-2), 3.95 (1H, dt, J=8.95, 6.49 Hz, OCCH$_2$CH$_2$CH$_3$), 3.98 (1H, dd, J=9.96, 9.31, Hz, H-6), 4.79–4.94 (8H, m, CH$_2$Ph), 7.26–7.36 (20 H, m, CH$_2$Ph). MS:m/z (+ve ion FAB) 597[(M+H)$^+$, 1], 91 [Bn$^+$,100]. MS:m/z (−ve ion FAB) 595 [(M−H$^+$)$^-$, 100], [(M−Bn$^+$), 20]. C: calculated, 76.48; found 76.52; H: calculated, 7.43, found 7.40.

D-1,4,5,6-Tetra-O-benzyl-2-O-butyl-myo-inositol (ent-15). A similar reaction and work-up of the diol ent-15 gave compound ent-15. [α]$^{24}_D$: +24.9° (c=1.00 in CHCl$_3$). Spectral data were in accordance with those obtained for enantiomer 15.

D-3,4,5,6-Tetra-O-benzyl-2-O-butyl-1-O-butyryl myo inositol (16). A solution of alcohol 15 (178 mg, 298 μmol) in dry pyridine (4 ml) were treated with butyric anhydride (158 μl, 447 μmol) and DMAP (38 mg, 29 μmol) and stirred at room temperature. When HPLC analysis (90% MeOH; 1.5 ml/min, t$_R$=6.40 min) showed no more starting material (18 h), the reaction mixture was evaporated under reduced pressure to give a crude oil. To remove residual pyridine the oil was dissolved in octane and evaporated three times. The residue was dissolved in tert-butyl methyl ether (20 ml) and was washed once with phosphate buffer (10 ml), once with sodium hydrogen carbonate (10 ml), once with sodium hydrogen sulfate (10 ml), once again with phosphate buffer (10 ml) and then with brine (10 ml). The organic layer was dried over Na$_2$SO$_4$ and filtered. Evaporation of the solvent gave pure 16 (176 mg, 89%) as an oil.—[α]$^{24}_D$: −15.4° (c=1.00 in CHCl$_3$). $^1$H NMR (CHCl$_3$, 360 MHZ); δ 0.91 (3H, t, J=7.21 Hz, CH$_3$), 0.93 (3H, t, J=7.21 Hz, CH$_3$), 1.35–1.56 (4 H, m, 2×CH$_2$), 1.58–1.72 (2H, m, CH$_2$), 2.21–2.26 (2H, m, CH$_2$), 3.48 (1H, dd, J=9.61, 2.40 Hz, H-3), 3.51 (1H, dd, J=9.66, 9.37, Hz, H-5), 3.52 (2H, tq, J=8.97, 6.25, Hz, O(O)CCH$_2$CH$_2$CH$_3$), 3.76 (2H, t, J=9.13, 6.25 Hz, O(O)CCH$_2$CH$_2$CH$_3$), 3.94 (1H, dd, J-2.40, 2.40 Hz, H-2), 4.00 (1H, dd, J=9.61, 9.61 Hz, H-4), 4.02 (1H, dd, J=9.85, 9.31 Hz, H-6), 4.73 (1H, dd, J=9.85, 2.40 Hz, H-1), 4.65–4.93 (8H, m, CH$_2$Ph), 7.25–7.34 (20 H, m, CH$_2$Ph). MS:m/z (+ve ion FAB) 665 [(M+H)$^+$, 1], 91 [Bn$^+$, 100].

D-1,4,5,6-Tetra-O-benzyl-3-O-butyl-2-O-butyryl-myo-inositol (ent-16). Compound ent-15 was butyrylated as described above for the other enantiomer to give compound ent-16.—[α]$^{24}_D$: +15.9° (c=1.10 in CHCl$_3$). Spectral data were in accordance with those of enantiomer 16.

D-2-O-Butyl-1-O-butyryl-myo-inositol (17). Compound 16 (170 mg, 255 μmol) was hydrogenated with palladium (10%) on carbon under hydrogen as described in the general procedure to give tetrol 17 (75 mg, 97%) as a solid after freeze drying. [α]$^{24}_D$: +41.9° (c=1.10 in MeOH). $^1$H NMR ([D$_6$]DMSO, 360 MHZ). δ 0.87 (3H, t, J=7.16 Hz, CH$_3$), 0.89 (3H, t, J=7.33 Hz, CH$_3$), 1.28–1.48 (4H, m, 2×CH$_2$), 1.52–1.62 (2H, m, CH$_2$), 2.24–2.36 (2H, m, CH$_2$), 2.96 (1H, dd, J=9.21, 9.21 Hz, H-5), 3.26 (1H, dd, J=9.55, 2.39 Hz, H-3), 3.35 (1H, dd, J=9.55, 9.21 Hz, H-4), 3.44 (1H, dt, J=9.43, 6.39 Hz, OCH$_2$CH$_2$CH$_2$CH$_3$), 3.52 (1 H, dd, J=10.23, 9.21 Hz, H-6), 3.57 (1H, dd, J=2.39, 2.39 Hz, H-2), 4.47 (2 H, dt, J=9.21, 6.39 Hz, OCH2CH2CH3), 4.47 (1H, dd, J=10.23, 2.39 Hz, H-1), 4.71 (2H, s (br), OH), 4.82 (1H, s (br), OH), 4.86 (1H, s (br), OH), MS:m/z (+ve ion FAB) 307 [(M+H)$^+$, 100], MS:m/z (−ve ion FAB) 305 [(M+H)$^+$, 34], 87 (BtO$^-$, 100]. C: calculated, 54.89; found 54.90; H: calculated, 8.55, found 8.51.

D-2-O-Butyl-3-O-butyryl-myo-inositol (ent-17). A similar reaction and work-up of the fully protected compound ent-16 afforded tetrol ent-17.—[α]$^{24}_D$: −40.5° (c=1.00 in MeOH). Spectral data were in accordance with those obtained for enantiomer 17.

D-2-O-Butyl-1-O-butyryl-myo-inositol 3,4,5,6-tetrakis (dibenzyl)phosphate (22). A solution of compound 17 (55 mg, 178 μmol) and tetrazole (152 mg, 2.15 mmol) in acetonitrile (2 ml) was treated with dibenzyl N,N-diisopropylphosphoramidite (726 μl, 2.15 mmol) for 22 h, oxidized with peracetic acid, and worked up as described. Purification by preparative HPLC (92% MeOH; 40 ml/min; t$_R$=29.00 min) gave compound 22 (192 mg, 80%) as an oil.—[α]$^{24}_D$: −3.4° (c=1.02 in CHCl$_3$). $^1$H NMR (CDCl$_3$, 360 MHZ): δ 0.79 (3H, t, J=7.30 Hz, CH$_3$), 0.86 (3 H, t, J=7.30 Hz, CH$_3$), 1.23–1.38 (2H, m, CH$_2$), 1.41–1.57 (4H, m, 2×CH$_2$), 2.01–2.17 (2 H, m, CH$_2$), 3.54 (1H, dt, J=8.52, 6.63 Hz, OCH$_2$CH$_2$CH$_2$CH$_3$), 3.60 (1H, dt, J=8.52, 7.74 Hz, OCH$_2$CH$_2$CH$_2$CH$_3$), 4.13 (1H, dd, J=2.52, 2.52 Hz, H-2), 4.22 (1H, ddd, J=9.73, 9.73, 2.52 Hz, H-3), 4.43 (1H, ddd, J=9.51, 9.51 Hz, H-5), 4.44 (1H, ddd, J=9.51, 9.51, 9.28 Hz, H-6), 4.89 (1H, ddd, J-9.73, 9.73, 9.51 Hz, H-4), 4.91–5.08 (17 H, m, CH$_2$Ph, H-1), 7.13–7.27 (40 H, m, CH$_2$Ph). $^{31}$P NMR (CDCl$_3$, $^1$H decoupled, 145.8 MHZ): δ−1.64 (1P, s), −1.42 (1P, s), −0.76 (1P, s), −0.53 (1P, s). MS:m/z (+ve ion FAB) 1347 [(M+H)$^+$, 33], 71 [Bt$^+$, 100]. MS:m/z (−ve ion FAB) 1255 [(M−Bn$^+$)$^-$, 16], 277 [OPO(OBn)$_2^-$, 100].

D-2-O-Butyl-3-O-butyryl-myo-inositol 1,4,5,6-tetrakis (dibenzyl)phosphate (ent-22). Compound ent-12 was phosphitylated and oxidized as described above for compound 22 to give the fully protected phosphate ent-22. [α]$^{24}_D$: +3.1° (c=1.10 in CHCl$_3$). Spectral data were in accordance with those obtained for enantiomer 22.

D-2-O-Butyl-1-O-butyryl-myo-inositol 3,4,5,6-tetrakisphosphate (23). Compound 22 (190 mg, 141 μmol) was hydrogenated with palladium (10%) on carbon as described in the general procedure to give title compound 23 (87 mg, 99%) as a solid after freeze drying.—[α]$^{24}_D$: +9.9° (c=1.10 in H$_2$O, pH 1.6). $^1$H NMR (D$_2$O, 360 MHZ): δ 0.75 (3H, t, J=7.15 Hz, CH$_3$), 0.76 (3H, t, J=7.31 Hz, CH$_3$), 1.19–1.29 (2H, m, CH$_2$), 1.38–1.53 (4H, m, 2×CH$_2$), 2.30 (2H, t, J=7.47, O(O)CCH$_2$CH$_2$CH$_3$), 3.58 (1H, dt, J-9.64, 6.44 Hz, OCH$_2$CH$_2$CH$_2$CH$_3$), 3.67 (1H, dt, J=9.64, 6.36 Hz, OCH$_2$CH$_2$CH$_2$CH$_3$), 4.01 (1H, dd, J=2.54, 2.23 Hz, H-2), 4.22 (1H, ddd, J-9.22, 9.22, 8.90 Hz, H-5), 4.23 (1H, ddd, J=9.54, 9.54, 2.54 Hz, H-3), 4.43 (1H, ddd, J=9.90, 9.22, 9.22 Hz, H-6), 4.48 (1H, ddd, J-9.54, 9.54, 9.54 Hz, H-4), 4.94 (1H, dd, J=9.90, 2.23 Hz, H-1). $^{31}$P NMR (D$_2$O, $^1$H decoupled, 145.8 Hz), δ−0.20 (2P, s), 0.40 (1P, s), 0.50 (1P, s). MS:m/z (+ve ion FAB) 627 [(M+H)$^+$, 8], 71 [Bt$^+$, 100]. MS/m/z (−ve ion FAB) 625 [(M−H$^+$)$^+$, 35], 79 [OP(O)$_2$, 100].

D-2-O-Butyl-3-O-butyryl-myo-inositol 1,4,5,6-tetrakisphosphate (ent-23). A similar reaction with the fully protected substrate ent-23 afforded the free acid ent-23 after freeze drying. [α]$^{24}_D$: −9.7° (c=1.00 in H$_2$O, pH 1.6). Spectral data were in accordance with those obtained for enantiomer 23.

D-2-O-Butyl-myo-inositol 3,4,5,6-tetrakisphosphate (6). Compound 23 (33 mg, 52 μmol) was treated with 1 M KOH (453 μl) to adjust the pH value to 12.8. The solution was stirred at room temperature for 2 days. The reaction mixture was directly poured onto an ion-exchange column (Dowex 50 WX 8, H$^+$) for purification. Lyophilization gave compound 6 (27 mg, 93%).—[α]$^{24}_D$: −1.1° (c=0.89 in H$_2$O, pH 1.6). $^1$H NMR (D$_2$O, 360 MHZ): δ 0.77 (3H, t, J-7.37 Hz, CH$_3$), 1.21–1.31 (2H, m, CH$_2$), 1.39–1.52 (2H, m, CH$_2$), 3.63 (1H, dt, J=9.30, 6.18 Hz, OCH$_2$CH$_2$CH$_2$CH$_3$), 3.67

(1H, dd, J=10.00, 2.63 Hz, H-1), 3.75 (1H, dt, J-9.30, 6.56 Hz, OCH$_2$CH$_2$CH$_2$CH$_3$), 3.94 (1H, dd, J-2.63, 2.37 Hz, H-2), 4.13 (1H, ddd, J-9.21, 9.21, 9.21 Hz, H-5), 4.17 (1H, ddd, J-9.47, 9.47, 2.37 Hz, H-3), 4.30 (1H, ddd, J-9.47, 9.47, 9.21 Hz, H-4), 4.43 (1H, ddd, J-10.00, 9.73, 9.21 Hz, H-6). $^{31}$P NMR (D$_2$O, $^1$H decoupled, 145.8 MHZ): δ–0.18 (1P, s), 0.55 (2P, s), 0.95 (1P, s). MS:m/z (+ve ion FAB) 557[(M+H$^+$)$^-$, 100]. MS:m/z (ve ion FAB) 555[(M–H)$^-$, 100].

D-2-O-Butyl-myo-inositol 1,4,5,6-tetrakisphosphate (ent-6). The butyryl groups of substrate ent-23 were hydrolyzed by the same method described above to give the tetrakisphosphate ent-6.—[α]$^{24}_D$: +1.6° (c=0.60 in H$_2$O, pH 1.6). Spectral data were in accordance with those obtained for enantiomer 6.

D-2-O-Butyl-1-O-butyryl-myo-inositol 3,4,5,6-tetrakisphosphate octakis (acetoxymethyl) ester (2). DIEA (182 μl, 1.06 mmol) and acetoxymethyl bromide (107 μl, 1.06 mmol) were added to a suspension of compound 23 (37 mg, 59 μmol) in acetonitrile (2 ml) as described in the general procedure. Purification by preparative HPLC (72% MeOH, 40 ml/min, t$_R$=21.12) gave compound 2 (33 mg, 46%) as a syrup [α]$^{24}_D$+1.1° (c=1.07 in toluene). $^1$H NMR ([D]$_8$toluene, 360 MHZ): δ 0.93 (3 H, t, J=7.28 Hz, CH$_3$), 0.97 (3 H, t, J-7.48 Hz, CH$_3$), 1.39–1.49 (2 H, m, CH$_2$), 1.51–1.60 (2 H, m, CH$_2$), 1.77–1.86 (24 H, 8 s, 8×OAc), 2.39 (1 H, dt, J-16.67, 7.38 Hz, CH$_2$), 2.63 (1 H, dt, J=16.67, 7.68, CH$_3$), 3.78 (1, H, dt, J=9.45, 6.30 Hz, OCH$_2$CH$_2$CH$_2$CH$_3$), 3.87 (1 H, dt, J=9.06, 6.30 Hz, OCH$_2$CH$_2$CH$_2$CH$_3$), 4.40 (1 H, dd, J=2.36, 2.36 Hz, H-2), 4.68 (1 H, ddd, J=9.55, 9.55, 2.36 Hz, H-3), 4.79 (1 H, ddd, J=9.55, 9.45, 9.45 Hz, H-5), 5.03 (1 H, ddd, J=9.55, 9.55, 9.55 Hz, H-4), 5.09 (1 H, ddd, J=10.04, 9.55, 9.55 Hz, H-6), 5.21 (1 H, dd, J=10.04, 2.36 Hz, H-1). 5.58–5.93 (16 H, m, CH$_2$OAc). $^{31}$P NMR ([D]$_8$-toluene, $^1$H decoupled, 145.8 MHZ): δ–4.42 (1 P, s), –3.98 (1 P, s), –3.48 (2 P, s). MS: m/z (+ve ion FAB) 1131 [(M-CH$_2$OAc$^+$+2 H), 44], 987 [(M-3 CH$_2$OAc$^+$+4 H)$^+$, 100], MS: m/z (–ve ion FAB) 1129 [(M-CH$_2$OAc$^+$), 18], 241 [OP(OCH$_2$OAc)$_2$, 100].

D-2-O-Butyl-3-O-Butyryl-myo-inositol 1,4,5,6-tetrakisphosphate octakis (acetoxymethyl) ester (ent-2). Alkylation of the phosphate ent 23 as described above afforded the octakis (acetoxymethyl) ester ent-2. [α]$^{24}_D$: 1.3° (c=0.60 in toluene). Spectral data were in accordance with those obtained for enantiomer 2.

D-3,4,5,6-Tetra-O-benzyl-1,2-di-O-butyl-myo-inositol (18). Sodium hydride (13 mg, 522 μmol) was added to a stirred solution of 9 (94 mg, 174 μmol) in dry DMF (3 ml) at room temperature in the dark. The mixture was stirred for 5 h, after which 1-butyl iodide (120 μl, 1.04 mmol) was added. The suspension was stirred for 36 h at 80° C., after HPLC (95% MeOH; 1.5 ml/min; t$_R$=7.26) showed a product. Excess of 1-butyl iodide and DMF were evaporated off under reduced pressure. The mixture was then dissolved in tert-butyl methyl ether (30 ml) and washed once with phosphate buffer (10 ml), aqueous sodium dithionate (10 ml) and brine (10 ml) successively. The organic layer was dried over Na$_2$SO$_4$, filtered, and the ether was evaporated off to give an oil. The crude oil was purified by preparative HPLC (95% MeOH, 40 ml/min; t$_R$=27.24 min) to give the title compound 18 (100 mg, 88%) as an oil. [α]$^{24}_D$: +1.3° (c=1.00 in CHCl$_3$). $^1$H NMR (CDCl$_3$, 360 MHZ): δ 0.092 (3 H, t, J=7.52 Hz, CH$_3$) 1.36–1.47 (4 H, m, 2×CH$_2$), 1.55–1.63 (4 H, m, 2×CH$_2$), 3.14 (1 H, dd, J-9.57, 2.28 Hz, H-3), 3.34 (1 H, dd, J-10.02, 2.28, H-1), 3.43 (1 H, dd, J=9.34, 9.34, H-5), 3.52 (1 H, dt, J=9.11, 6.60 Hz, OCCH$_2$CH$_2$CH$_3$), 3.60 (1 H, dt, J=9.11, 6.60 Hz, OCCH$_2$CH$_2$CH$_3$), 3.75 (2 H, t, J-6.60 Hz, OCCH$_2$CH$_2$CH$_3$), 3.89 (1 H, dd, J=2.28, 2.28 Hz, H-2), 3.92 (1 H, dd, J-9.57, 9.34 Hz, H-4), 4.00 (1 H, dd, J=10.02, 9.34 Hz, H-6), 4.71–4.93 (8 H, m, CH$_3$Ph), 7.24–7.39 (20 H, m, CH$_2$Ph). MS: m/z (+ve ion FAB) 653 [(M+H)$^+$, 1], 91 [Bn$^+$, 100]. MS: m/z 653.383 (M+H)$^+$ (calculated for C$_{42}$H$_{53}$O$_6$ 653.384).

D-1,4,5,6-Tetra-O-benzyl-2,3-di-O-butyl-myo-inositol (ent-18). A similar reaction and work-up of the compound ent-9 gave compound ent-18. [α]$^{24}_D$: 1.2° (c=2.20 in CHCl$_3$). Spectral data were in accordance with those obtained for enantiomer 18.

D-1,2-Di-O-butyl-myo-inositol (19). Compound 18 (100 mg, 153 μmol) was hydrogenated with palladium (10%) on carbon under hydrogen as described in the general procedure to give tetrol 19 (40 mg, 92%) as a solid after freeze drying. (from ethanol) [α]$^{24}_D$: +18.7° (c=0.80 in MeOH). $^1$H NMR ([D$_6$]DMSO, 360 MHZ): δ 0.89 (3 H, t, J=7.52 Hz, CH$_3$), 0.91 (3 H, t, J=7.38 Hz, CH$_3$), 1.24–1.39 (4 H, m, CH$_2$), 1.41 1.53 (4 H, m, CH$_2$), 2.88 (1 H, dd, J=9.55, 2.63 Hz, H-3), 2.93 (1 H, dd, J=9.93, 2.63 Hz, H-1), 3.14 (1 H, dt, J=9.51, 6.42 Hz, OCCH$_2$CH$_2$CH$_2$CH$_3$), 3.31 (1 H, dd, J=9.52, 9.52 Hz, H-5), 3.39–3.67 (6 H, m, 3×OCCH$_2$CH$_2$CH$_2$CH$_3$, H-2, H-4, H-6), 4.43 (1 H, s, OH), 4.52 (1 H, S, OH), 4.59 (2 H, s (br), OH), MS: m/z (+ve ion FAB) 293 [(M+H)$^+$, 100]. MS: m/z (–ve ion FAB) 291 [(M–H$^+$), 100].

D-2,3-Di-O-butyl-myo-inositol (ent-19). A similar reaction and work-up of the fully protected compound ent-18 afforded tetrol ent-19. [α]$^{24}_D$: –18.9° (c=1.36 in MeOH). Spectral data were in accordance with those obtained for enantiomer 19.

D-1,2-Di-O butyl-myo-inositol 3,4,5,6-tetrakis(dibenzyl) phosphate (24). A solution of compound 19 (40 mg, 137 μmol) and tetrazole (115 mg, 1.64 mmol) in acetonitrile (2 ml) was treated with dibenzyl N-diisopropylphosphoramidite (552 μl, 1.64 mmol) for 18 h, oxidized with peracetic acid, and worked up as described. Purification by preparative HPLC (93% MeOH; 40 ml/min; t$_R$=26.05 min) gave compound 24 (133 mg, 73%) as an oil. [α]$^{24}_D$: –2.3° (c–1.00 in CHCl$_3$). $^1$H NMR (CDCl$_3$, 360 MHZ): δ 0.79 (3 H, t, J=7.31 Hz, CH$_3$). 0.86 (3 H, t, J=7.31 Hz, CH$_3$), 1.13–1.38 (4 H, m, 2×CH$_2$), 1.41–1.56 (4 H, m, 2×CH$_2$), 3.24 (1 H, dd, J=9.89, 2.15 Hz, H-1), 3.36 (1 H, dt, J=8.31, 7.41 Hz, OCH$_2$CH$_2$CH$_2$CH$_3$), 3.41 (1 H, dt, J=8.31, 5.87 Hz, OCH$_2$CH$_2$CH$_2$CH$_3$), 3.60 (1 H, dt, J=8.88, 6.55 Hz, OCH$_2$CH$_2$CH$_2$CH$_3$), 3.71 (1 H, dt, J=8.88, 6.55 Hz, OCH$_2$CH$_2$Ch$_2$Ch$_3$), 4.16 (1 H, ddd, J=9.89, 9.89, 2.47 Hz, H-3), 4.21 (1 H, dd, J=2.47, 2.15 Hz, H-2), 4.48 (1 H, ddd, J=9.67, 9.67, 9.67 Hz, H-5), 4.79 (1 H, ddd, J=9.89, 9.67, 9.67 Hz, H-6), 4.95 (1 H, ddd, J=9.89, 9.67, 9.67 Hz, H-4), 4.96–5.09 (16 H, m, CH$_2$Ph), 7.12–7.32 (40 H, m, CH$_2$Ph). $^{31}$P NMR (CDCl$_3$, $^1$H decoupled, 145.8 MHZ): δ–1.82 (1 P, s), –1.59 (1 P, s), –0.81 (1 P, s), –0.68 (1 P, s). MS: m/z (+ve ion FAB) 1333 [(M+H)$^+$, 2], 91 [Bn$^+$, 100]. MS: m/z (–ve ion FAB) 1241 [(M–Bn$^-$)$^-$, 8], 277 [OPO(OBn)$^-_2$, 100].

D-2.3-Di-O-butyl-myo-inositol 1,4,5,6-tetrakis (dibenzyl)phosphate (ent-24). Compound ent-19 was phosphitylated and oxidized as described above for compound 24 to give the fully protected phosphate ent-24. [α]$^{24}_D$: +2.5° (c=1.15 in CHCl$_3$). Spectral data were in accordance with those obtained for enantiomer 24.

D-1,2-Di-O-butyl-myo-inositol 3,4,5,6-tetrakisphosphate (7). Compound 24 (134 mg, 100 μmol) was hydrogenated with palladium (10%) on carbon as described in the general procedure to give title compound 7 (52 mg, 87%) as solid after freeze drying. (c=1.10 in H$_2$O, pH 1.6). $^1$H NMR (D$_2$O, 360 MHZ): δ 0.70 (3 H, t, J=7.37 Hz, CH$_3$), 0.71 (3 H, t, J=7.37 Hz, CH$_3$), 1.13–1.24 (4 H, m, 2×CH$_2$), 1.32–1.46 (4

H, m, 2×CH$_2$), 3.39 (1 H, dd, J=9.47, 2.33 Hz, H-1), 3.45 (1 H, dt, J=8.59, 8.16 Hz OCH$_2$CH$_2$CH$_2$CH$_3$), 3.51 (1 H, dt, J=8.59, 5.79 Hz, OCH$_2$CH$_2$CH$_2$CH$_3$), 3.56 (1 H, dt, J=9.47, 6.31 Hz, OCH$_2$CH$_2$CH$_2$CH$_3$), 3.65 (1 H, dt, J=9.47, 6.84 Hz, OCH$_2$CH$_2$CH$_2$CH$_3$), 4.02–4.08 (2 H, m, H-2, H-3), 4.11 (1 H, ddd, J=9.47, 9.47, 9.47 Hz, H-5), 4.27 (1 H, ddd, J=9.47, 9.47 9.47 Hz, H-4), 4.39 (1 H, ddd, J=9.47, 9.21, 9.21 Hz, H-6). $^{31}$P NMR (D$_2$O, $^1$H decoupled, 145.8 MHZ): δ–0.69 (1 P, s), –0.41 (2 P, s), –0.12 (1 P, s). MS: m/z (+ve ion FAB) 613 [(M+H)$^+$, 15], 81 [PO(OH)$^+_2$, 100]. MS: m/z (–ve ion FAB) 611 [(M–H$^+$)$^-$, 90] 79 [OP(O)$^-_2$, 100].

D-2,3-Di-O-butyl myo inositol 1,4,5,6-tetrakisphosphate (ent 7). A similar reaction with the fully protected substrate ent-24 afforded the free acid ent-7 after freeze drying. (c=1.00 in H$_2$O, pH 1.6). Spectral data were in accordance with those obtained for enantiomer 7.

D-1,2-Di-O-butyl-myo-inositol 3,4,5,6-tetrakisphosphate octakis (acetoxymethyl) ester (3). DIEA (187 μl, 1.00 mmol) and acetoxymethyl bromide (111 μl, 1.00 mmol) were added to a suspension of compound 7 (34 mg, 55 μmol) in acetonitrile (2 ml.) as described in the general procedure. Purification by preparative HPLC (73% MeOH, 40 ml/min, t$_R$=20.40) gave compound 3 (42 mg, 65%) as a syrup. [α]$^{24}_D$: –2.3° (c=1.03 in toluene). $^1$H NMR ([D]$_8$ toluene, 360 MHZ): δ 0.92 (3 H, t, J=7.28 Hz, CH$_3$), 0.99 (3 H, t, J=7.48 Hz, CH$_3$), 1.33–1.47 (4 H, m, 2×CH$_2$), 1.48–1.54 (2 H, m, CH$_2$), 1.61–1.69 (2 H, m, CH$_2$), 1.77–1.87 (24 H, 8 s, 8×OAc), 3.11 (1 H, dd, J=9.84, 2.36 Hz, H-1). 3.46 (1 H, dt, J=8.79, 7.28 Hz, OCH$_2$CH$_2$CH$_2$CH$_3$), 3.56 (1 H, dt, J=8.79, 7.28 Hz OCH$_2$CH$_2$CH$_2$CH$_3$), 3.84 (1 H, t, J=6.50 Hz, 2×OCH$_2$CH$_2$CH$_2$CH$_3$). 4.34 (1 H, dd, J=2.36, 2.36 Hz, H-2), 4.49 (1 H, ddd, J=9.45, 9.45, 2.36 Hz, H-3), 4.68 (1 H, ddd, J=9.65, 9.65, 9.65 Hz, H-5), 4.90 (1 H, ddd, J=9.65, 9.45, 9.45 Hz, H-4), 5.06 (1 H, ddd, J=9.84, 9.65, 9.65 Hz, H-6), 5.68–5.96 (16 H, m, CH$_2$OAc). $^{31}$P NMR ([D]$_8$-toluene, $^1$H decoupled, 145.8 MHZ) δ–5.12 (1 P, s), –3.98 (1 P, s), –3.69 (1 P, s), –3.42 (1 P, s) MS: m/z (+ve ion FAB) 1189 [(M+H)$^+$, 3], 1045 [(M–2×CH$_2$OAc$^+$+3 H)$^+$, 100], MS: m/z (–ve ion FAB) 1116 [(M–CH$_2$OAc$^+$)$^-$, 30], 241 [OP (OCH$_2$OAC)$^-_2$, 100].

D-2,3-Di-O-butyl-myo-inositol 1,4,5,6-tetrakisphosphate octakis (acetoxymethyl) ester (ent-3). Alkylation of the phosphate ent-7 as described above afforded the octakis (acetoxymethyl) ester ent-3. [α]$^{24}_D$: +2.5° (c=1.10 in toluene). Spectral data were in accordance with those obtained for enantiomer 3.

rac-1,2-Di-O-cyclohexylidene-myo-inositol 3,4,5,6-tetrakis (dibenzyl)phosphate (rac-26). A solution of compound rac-25 (130 mg, 500 μmol) and tetrazole (350 mg, 5.00 mmol) in acetonitrile (6 ml) was treated with dibenzyl N,N diisopropylphosphoramidite (1.68 ml, 5.00 mmol) for 26 h, oxidized with peracetic acid, and worked up as described. Purification by preparative HPLC (93% MeOH; 40 ml/min, t$_R$=22.35 min) gave compound rac-26 (306 mg, 47%) as an oil. $^1$H NMR (CDCl$_3$, 360 MHZ) δ 1.20–1.80 (10 H, m, CH$_2$ (cyclohex.)), 4.26 (1 H, dd, J=6.01, 6.01 Hz, H-1), 4.66 (1 H, dd, J=6.01, 3.43 Hz, H-2), 4.76–4.81 (2 H, m, H-3, H-5) 4.92–5.17 (18 H, m, CH$_2$Ph, H-4, H-6), 7.20–7.40 (40 H, m, CH$_2$h). $^{31}$P NMR (CDCl$_3$, $^1$H decoupled, 145.8 MHZ): δ–1.69 (1 P, s), –1.59 (1 P, s), –1.52 (1 P, s), –1.00 (1 P, s). MS: m/z (–ve ion FAB) 1209 [(M–Bn$^+$)$^-$, 1], 277 [OPO(OBn)$^-_2$, 100].

rac-1,2-Di-O-cyclohexylidene-myo-inositol 3,4,5,6-tetrakisphosphate (rac-8) ethyl-diisopropylamino salt. rac-26 (91 mg, 70 μmol) was dissolved in dry ethanol (4 ml), before dry ethyl-diisopropylamine (95 μl, 560 μmol) was added, followed by palladium (10%) on carbon (84 mg, 840 μmol). After stirring the solution at room temperature for 6 days under hydrogen atmosphere the catalyst was removed by ultrafiltration and the filtrate was freeze dried to give title compound rac-8 (108 mg, 96%). $^1$H NMR, (D$_2$O, 360 MHZ): δ 1.30–1.90 (10 H, m, CH$_2$ (cyclohex.)), (1 H, ddd, J=9.08, 9.08, 8.23 Hz, H-5), 4.18–4.26 (2 H, m, H-1, H-3), 4.32–4.40 (2 H, m, H-4, H-6), 4.55 (1 H, dd, J=1.26, 3.69 Hz, H-2). $^{31}$P NMR (D$_2$O, $^1$H decoupled, 145.8 MHZ): δ–0.24 (1 P, s), 0.10 (1 P, s), 0.85 (1 P, s), 0.90 (1 P, s).

rac-1,2-Di-O-cyclohexylidene-myo-inositol 3,4,5,6-tetrakisphosphate octakis (acetoxymethyl) ester (rac-4). DIEA (205 μl, 1.20 mmol) and acetoxymethyl bromide (120 μl, 1.20 mmol) were added to suspension of compound rac-8 (108 mg, 66 μmol) in acetonitrile (2 ml) as described in the general procedure. Purification by preparative HPLC (68% MeOH, 40 ml/min, t$_R$=19.35) gave compound rac-4 (50 mg, 65%) as a syrup. $^1$H NMR ([D]$_8$toluene, 360 MHZ): δ 1.20–1.75 (10 H, m, CH$_2$ (cyclohex.)), 1.811.92 (24 H, 8 s, 8×OAc), 4.28 (1 H, dd, J=5.51, 5.51 Hz, H-1). 4.77 (1 H, dd, J=5.51, 3.54 Hz, H-2), 4.91–4.99 (2 H, m, H-5, H-6), 5.07 (1 H, ddd, J=8.66, 8.27, 3.54 Hz, H 3 ), 5.17 (1 H, ddd, J=9.05, 8.66, 7.08 Hz, H-4), 5.65–5.94 (16 H, m, CH$_2$OAc). $^{31}$P NMR ([D]$_8$-toluene, $^1$H decoupled, 145.8 MHZ): δ–4.56 (1 P, s), –4.07 (1 P, s), –3.67 (1 P, s), –3.55 (1 P, s). MS: m/z (–ve ion FAB) 1083 [(M–CH$_2$OAc$^+$)$^-$, 35], 241 [OP (OCH$_2$OAc)$^-_2$, 100].

rac-3,4,5,6-Tetra-O-benzyl-2-deoxy-2-iodo-1-O-(4-methoxybenzyl)-myo-inositol (rac-56). A mixture of dry rac-55 (rac-3,4,5,6-tetra-O-benzyl-1-O-(4-methoxybenzyl)-myo-inositol) (1.32 g, 2 mmol), triphenylphosphine (2.15 g, 8.2 mmol), imidazole (549 mg, 8.2 mmol), and iodine (1.52 g, 6 mmol) were stirred under reflux in dry toluene (100 ml) for 41 h. The reaction mixture was cooled to room temperature, saturated aqueous sodium hydrogencarbonate (100 ml) was added, and the mixture was stirred for 10 min. Iodine was added in portions. When the toluene phase remained iodine-colored it was stirred for an additional 15 min. Excess of iodine was removed by the addition of aqueous sodium dithionite solution. The organic and the aqueous phase were separated in a separating funnel and the organic phase was washed (twice) with brine. The toluene phase was dried over Na$_2$SO$_4$ and filtered. Evaporation of the mixture and crystallization gave pure rac-56 (1.01 g, 73%). Mp.: 131.5°–132.4° C. (from methanol). $^1$H NMR (CDCl$_3$, 360 MHZ): δ 3.49 (1 H, dd, J=9.27, 9.27 Hz), 3.50 (1 H, dd, J=9.27, 9.27 Hz), 3.80 (3 H, s, OMe), (1 H, dd, J=9.78, 9.31 Hz, H-4), 4.06 (1H, dd, J=11.08, 11.08 Hz), 4.82–4.92 (10 H, m, 4×CH$_2$Ph and CH$_2$ in PMB), 6.87 (2 H, d, PMB ArH), 7.23–7.37 (22 H, m, 4×CH$_2$Ph and PMB ArH). MS: m/z (+ve ion FAB) 924 [(M+NBA+H)$^+$, 1], 121 [PMB$^+$, 100].

rac-3,4,5,6-Tetra-O-benzyl-2-deoxy-1-O-(4-methoxybenzyl)-myo-inositol (rac-57). Compound rac-56 was dissolved in dry toluene (150 ml) and AIBN (63 mg, 355 μmol) and Bu$_3$SnH (1.63 ml, 6.3 mmol) were added. The solution was heated under an argon atmosphere for 2 h. The reaction mixture was cooled and was washed once with phosphate buffer (30 ml) and once with brine (30 ml). The organic layer was dried over Na$_2$SO$_4$ and filtered. Evaporation of the mixture and crystallization gave 57 (692 mg, 76%). Mp.: 76.2°–76.8° C. (from methanol). $^1$H NMR (CDCl$_3$, 360 MHZ): δ 1.64 (1 H, ddd, J=12.73, 12.73, 12.73 Hz, H-2 (ax)), 2.39 (1 H, ddd, J=12.73, 4.39, 4.39 Hz, H-2 (eq)), 3.39–3.46 (2 H, m, H-1, H-3), 3.46 (1 H, dd, J=9.22, 8.87 Hz, H-5), 3.55 (1 H, dd, J=9.22, 9.22 Hz, H-4), 3.56 (1 H, dd, J=9.22, 9.22 Hz, H-6), 3.81 (3 H, s, OMe), 4.60–4.94

(10 H, m, 4×CH$_2$Ph and CH$_2$ in PMB), 6.86 (2 H, d, PMB ArH), 7.24–7.33 (22 H, m, 4×CH$_2$Ph and PMB ArH). MS: m/z (−ve ion FAB) 643 [(M−H$^+$)$^−$, 1], 523 [M−PMB$^+$)$^−$, 100].

rac-3,4,5,6-Tetra-O-benzyl-2-deoxy-myo-inositol (58). DDQ (367 mg, 1.62 mmol) was added to a solution of rac-57 (600 mg, 931 μmol) in CH$_2$Cl$_2$ (10 ml) containing small amounts of water (5%). After the suspension had been stirred at room temperature for 28 min HPLC analysis (90% MeOH; 1.5 ml/min; t$_R$=4.27 min) showed the reaction to be complete. The reaction mixture was evaporated under reduced pressure and purified by preparative HPLC (90% MeOH; 40 ml/min; 20.00 min) to give rac-58 (232 mg, 48%) as a solid. Mp.: 126.7° C. (from methanol). $^1$H NMR (CDCl$_3$, 360 MHZ): δ 1.64 (1 H, ddd, J=12.73, 12.73, 12.73, 12.73 Hz, H-2 (ax)), 2.39 (1 H, ddd, J=12.73, 4.39, 4.39 Hz, H-2 (eq)), 3.39–3.46 (2 H, m, H-1, H-3), 3.46 (1 H, dd, J=9.22, 8.87 Hz, H-5), 3.55 (1 H, dd, J=9.22, 9.22 Hz, H-4), 3.56 (1 H, dd, J=9.22, 9.22 Hz, H-6), 3.81 (3 H, s, OMe), 4.60–4.94 (10 H, m, 4×CH$_2$Ph and CH$_2$ in PMB), 6.86 (2 H, d, PMB ArH), 7.24–7.33 (22 H, m, 4×3 CH$_2$Ph and PMB ArH). MS: m/z (+ve ion FAB) 525 [(M+H)$^+$, 1], 91 [Bn$^+$)$^−$, 100].

rac-3,4,5,6-Tetra-O-benzyl-1-O-butyryl-2-deoxy-myo-inositol (rac-59). A solution of rac-58 (186 mg, 355 μmol) butyric anhydride (70 μl, 426 μmol) and DMAP (12 mg, 10 μmol) in dry pyridine (5 ml) was stirred at room temperature for 18 h. The solvents were evaporated under high vacuum to give an oil. Residual pyridine was removed by evaporating three times with octane. The residue was dissolved in tert-butyl methyl ether (30 ml) and was washed once with phosphate buffer (20 ml), once with sodium hydrogen carbonate (20 ml), once with sodium hydrogen sulfate (20 ml), once again with phosphate buffer (20 ml) and then with brine (20 ml). The organic layer was dried over Na$_2$SO$_4$ and filtered. Evaporation of the solvent gave pure rac-59 (196 mg, 94%) as a solid. Mp.: 110.1°–110.3° C. (from methanol). $^1$H NMR (CHCl$_3$, 360 MHZ): δ 0.91 (3 H, t, J=7.25 Hz, CH$_3$), 0.98 (3 H, t, J=7.46 Hz, CH$_3$), 1.32–1.42 (2 H, m, CH$_2$), 1.50–1.60 (2 H, m, CH$_2$), 1.69 (2 H, tq, J=7.46, 7.46 Hz, O(O)CCH$_2$CH$_2$CH$_3$), 2.39 (2 H, t, J=7.46 Hz, O(O)CCH$_2$CH$_2$CH$_3$), 3.31 (1 H, dd, J=9.66, 2.63 Hz, H-1), 3.44 (1 H, dt, J=9.07, 6.81 Hz, OCH$_2$CH$_2$CH$_2$CH$_3$), 3.48 (1 H, dd, J=9.66, 3.07 Hz, H-3), 3.49 (1 H, dd, J=9.66, 9.22 Hz, H-5), 3.67 (1 H, dt, J=8.78, 6.81 Hz, OCH$_2$CH$_2$CH$_2$CH$_3$), 3.81 (1 H, dd, J=9.66, 9.66 Hz, H-4), 3.86 (1 H, dd, J=9.66, 9.22 Hz, H-6), 4.51–4.93 (8H, m, CH$_2$Ph), 5.83 (1 H, dd, J=3.07, 2.63 Hz, H-2), 7.26–7.36 (20 H, m, CH$_2$Ph). MS: m/z (+ve ion FAB) 595 [(M+H)$^+$, 21], 91 [Bn$^+$, 100].

rac-1-O-butyryl-2-deoxy-myo-inositol (rac-60). Compound rac-59 (177 mg, 297 μmol) was hydrogenated with palladium (10%) on carbon under hydrogen as described in the general procedure to give tetrol rac-60 (68 mg, 98%) as a solid after freeze drying. Mp: 174.9°–175.9° C. (from ethanol). $^1$H NMR ([D$_6$]DMSO, 360 MHZ): δ 0.84 (3 H, t, J=7.38 Hz, CH$_3$), 0.90 (3 H, t, J=7.38 Hz, CH$_3$), 1.21–1.31 (2 H, m, CH$_2$), 1.36–1.44 (2 H, m, CH$_2$), 1.54 (2 H, tq, J=7.38 , 7.00 Hz, O(O)CCH$_2$CH$_2$CH$_3$), 2.24 (2 H, t, J=7.00 Hz, O(O)CCH$_2$CH$_2$CH$_3$), 2.97 (1 H, dd, J=8.94, 8.55 Hz, H-5), 3.10 (1 H, dd, J=9.72, 2.72 Hz, H-1), 3.25–3.35 (4 H, m, H-3, H-4, H-6, OCH$_2$CH$_2$CH$_2$CH$_3$), 3.50 (1 H, dt, J=8.94, 6.60 Hz, OCH$_2$CH$_2$CH$_2$CH$_3$), 4.85 (4 H, s (br), OH), 5.36 (1 H, dd, J=2.72, 2.33 Hz, H-2). MS: m/z (+ve ion FAB) 235 [(M+H)$^+$, 100]. MS: m/z (−ve ion FAB) 233 [(M−H$^+$)$^−$, 27], 87 [BtO$^−$, 100].

rac-1-O-butyryl-2-deoxy-myo-inositol 3,4,5,6-tetrakis(dibenzyl)phosphate (rac-61). A solution of tetrol rac-60 (44 mg, 190 μmol) and tetrazole (160 mg, 2.28 mmol) in acetonitrile (2 ml) was treated with dibenzyl NN-diisopropylphosphoramidite (767 μl, 2.28 mmol) for 36 h, oxidized with peracetic acid, and worked up as described. Purification by preparative HPLC (92% MeOH; 40 ml/min; t$_R$=21.55 min) gave compound rac-61 (172 mg, 71%) as an oil. $^1$H NMR (CDCl$_3$, 360 MHZ): δ 0.79 (3 H, t, J=7.57 Hz, CH$_3$), 1.45 (2 H, tqu, J=7.57, 7.57 Hz β-CH$_2$), 1.46 (1 H, ddd, J=12.92, 11.14, 11.14 Hz, H-2 (ax)), 2.08 (2 H, t, J=7.57 Hz, α-CH$_2$), 2.58 (1 H, ddd, J=12.92, 4.90, 4.90 Hz, H-2 (eq)), 4.28–4.37 (1 H, m, H-3), 4.44 (1 H, dd, J=9.24, 9.24, 9.24 Hz, H-5), 4.53 (1 H, ddd, J=9.24, 9.02, 9.02 Hz, H-4), 4.56 (1 H, ddd, J=9.24, 9.24, 9.24 Hz, H-6), 4.83–5.08 (17 H, m, 8×CH$_2$Ph, H-1), 7.12–7.32 (40 H, m, 8×CH$_2$Ph). $^{31}$P NMR (CDCl$_3$, $^1$H decoupled, 145.8 MHZ): δ−1.67 (1 P, s), −1.33 (1 P, s), −0.85 (1 P, s), −0.64 (1 P, s). MS: m/z (+ve ion FAB) 1275 [(M+H)$^+$, 4] 91 [Bn$^+$, 100]. MS: m/z (−ve ion FAB) 1183 [(M−Bn$^+$)$^−$, 16], 277 [OPO(OBn)$^−$, 100].

rac-1-O-butyryl-2-deoxy-myo-inositol 3,4,5,6-tetrakisphosphate (rac-62). Compound rac-61 (165 mg, 130 μmol) was hydrogenated with palladium (10%) on carbon as described in the general procedure to give title compound rac-62 (65 mg, 90%) as a solid after freeze drying. $^1$H NMR (D$_2$O, 360 MHZ): δ 0.67 (3 H, t, J=7.41 Hz, CH$_3$) 1.33–1.43 (2 H, m, β-CH$_2$), 1.62 (1 H, ddd, J=11.72, 11.71, 11.38 Hz, H-2 (ax)), 2.17 (2 H, m, α-CH$_2$), 2.25 (1 H, ddd, J=11.38, 2.24, 2.24 Hz, H-2 (eq)), 4.07–4.23 (4 H, m, H-3, H-4, H-5, H-6), 4.85 (1 H, m, H-1), $^{31}$P NMR (D$_2$O, $^1$H decoupled. 145.8 MHz): δ−0.39 (2 P, s), −0.13 (1 P, s), 0.41 (1 P, s). MS: m/z (+ve ion FAB) 555 [(M+H)$^+$, 100], 485 [M−Bt$^+$+2H+], 40]. MS: m/z (−ve ion FAB) 553 [(M−H$^+$)$^−$, 100].

rac-1-O-butyryl-2-deoxy-myo-inositol 3,4,5,6-tetrakisphosphate octakis(acetoxymethyl) ester (rac-51). DIEA (201 μl, 1.19 mmol) and acetoxymethyl bromide (119 μl, 1.19 mmol) were added to a suspension of compound rac-62 (37 mg, 66 μmol) in acetonitrile (2 ml) as described in the general procedure. Purification by preparative HPLC (69% MeOH, 40.00 ml/min, t$_R$=12.10) gave compound rac-51 (31 mg, 50%) as a syrup. $^1$H NMR ([D]$_8$ toluene, 360 MHZ): δ 0.96 (3 H, t, J=7.48 Hz, CH$_3$), 1.54 (1 H, ddd, J=12.70, 12.70, 12.31 Hz, H-2 (ax)), 1.63–1.74 (2 H, m, β-CH$_2$), 1.81–1.87 (24 H, 8 s, 8×OAc), 2.30 (1 H, dt, J=16.28, 7.68 Hz, α-CH$_2$), 2.52 (1 H, dt, J=16.28, 7.88 Hz, α-CH$_2$), 2.64 (1 H, ddd, J=12.31, 5.31, 5.31 Hz, H-2 (eq)), 4.40–4.59 (4 H, m, H-3, H-4, H-5, H-6), 5.03 (1 H, ddd, J=12.20, 9.53, 5.31 Hz, H-1), 5.65–5.95 (16 H, m, 8×CH$_2$OAc). $^{31}$P NMR ([D]$_8$-toluene, $^1$H decoupled, 145.8 MHZ): δ−4.68 (1 P, s), −4.32 (1 P, s), −3.77 (1 P, s), −3.65 (1 P, s). MS:m/z (+ve ion FAB) 1131 [(M+H)$^+$, 12], 987 [(M−2 CH$_2$OAc$^+$+3 H)$^+$, 100], MS; m/z (−ve ion FAB) 1059 [(M−Bt$^+$)$^−$, 16], 241 [OP(OCH$_2$OAc)$_2$, 100].

rac-2-deoxy-myo-inositol 3,4,5,6-tetrakisphosphate (rac-53). Compound 62 was treated with 1 M KOH (260 μl) to adjust the pH to 12.8. The solution was stirred at room temperature for 2 days. The reaction mixture was directly poured onto an ion-exchange column (Dowex 50 WX 8, H$^+$) for purification. Lyophilization gave compound rac-53. $^1$H NMR (D$_2$O, 360 MHZ): δ 1.55 (1 H, ddd, J=12.09, 12.09, 12.09 Hz, H-2 (ax)), 2.24 (1 H, ddd, J=12.09, 4.31, 4.31 Hz, H-2 (eq)), 4.79 (1 H, ddd, J=12.09, 8.77, 4.31 Hz, H-1), 5.14 (1 H, ddd, J=9.25, 9.25, 8.83 Hz, H-5), 5.18–5.73 (3 H, m, H-3, H-4, H-6) $^{31}$P NMR (D$_2$O, $^1$H decoupled, 145.8 MHZ): δ−0.08 (1 P, s) 0.28 (1 P, s), 0.34 (1 P, s), 0.90 (1 P, s). MS: m/z (+ve ion FAB) 485 [(M+H)$^+$, 100] MS (−ve ion FAB) 483 [(M−H$^+$)$^−$, 100].

rac-1-O-benzyl-6-O-butyryl-2,3-4,5-di-O-cyclohexylidene-myo-inositol (rac-100). A solution of rac- 1-O-benzyl-2,3-4,5-di-Q-cyclohexylidene-myo-inositol (200 mg, 465 μmol), butyric anhydride (144 μl, 571 μmol) and DMAP (6 mg, 50 μmol) in dry pyridine (3 ml) was stirred at room temperature for 36 h. The solvents were evaporated under high vacuum to give an oil. Residual pyridine was removed by evaporating three times with octane. The residue was dissolved in tert-butyl methyl ether (40 ml) and was washed once with phosphate buffer (20 ml), once with sodium hydrogen carbonate (20 ml), once with sodium hydrogen sulfate (20 ml), once again with phosphate buffer (20 ml) and then with brine (20 ml). The organic layer was dried over $Na_2SO_4$ and filtered. Evaporation of the solvent gave pure rac-100 (186 mg, 80%) as an oil. $^1$H NMR ($CHCl_3$, 360 MHZ): δ 0.94 (3 H, t, J=7.40 Hz, $CH_3$), 1.39–1.79 (12 H, m, $CH_2$ (cyclohex.), $CH_2$ (β-$CH_2$)), 2.23–2.37 (2 H, m, α-$CH_2$), 3.60 (1 H, dd, J=2.85, 2.08 Hz, H-1), 3.63 (1 H, dd, J=10.86, 8.09 Hz, H-5), 4.31 (1 H, dd, J=7.17, 2.85 Hz, H-2), 4.34 (1 H, dd, J=10.86, 8.56 Hz, H-4), 4.38 (1 H, dd, J=8.56, 7.17 Hz, H-3), 4.78 (2 H, AB, J=10.01 Hz, $CH_2$-Ph, 5.24 (1 H, dd, J=8.09, 2.08 Hz, H-6), 7.24–7.39 (5 H, m, $CH_2$Ph). MS: m/z (+ve ion FAB) 501 [(M+H)$^+$, 2], 91 [Bn$^+$, 100].

rac-1-O-benzyl-6-O-butyryl-myo-inositol (rac-101). A solution of rac-l00 (186 mg, 372 μmol) in $CH_3CN/H_2O$ (100:1, 8 ml) was stirred with trifluoroacetic acid (4 ml) at room temperature for 2 h. The solvent was evaporated in high vacuum to give the title compound rac-101 (125 mg, 98%) as an oil. $^1$H NMR ($CHCl_3$, 360 MHZ): δ 0.86 (3 H, t, J=7.35 Hz, $CH_3$), 1.44–1.56 (2 H, m, β-$CH_2$), 2.13–2.31 (2 H, m, α-$CH_2$), 3.12 (1 H, dd, J=9.13, 9.13 Hz, H-5), 3.15 (1 H, dd, J=9.58, 2.45 Hz, H-3), 3.32 (1 H, dd, J=10.05, 2.45 Hz, H-1), 3.44 (1 H, dd, J=9.36, 9.36 Hz, H-4), 4.01 (1 H, dd, J=2.45, 2.45 Hz, H-2), 4.44 (2 H, AB, J=9.93 Hz, $CH_2$Ph,), 5.12 (1 H, dd, J=10.05, 9.13 Hz, H-6), 7.24–7.34 (5 H, m, $CH_2$Ph). MS: m/z (+ve ion FAB)341 [(M+H)$^+$, 10] 91 [Bn$^+$, 100]. MS: m/z (–ve ion FAB) 339 [(M–H$^+$)$^-$, 14], 87 [BtO$^-$, 100].

rac-1-O-benzyl-6-O-butyryl-myo-inositol 2, 3, 4, 5-tetrakis (dibenzyl) phosphate (rac-102). A solution of compound rac-101 (145 mg, 426 μmol) and tetrazole (358 mg, 5.11 mmol) in acetonitrile (3 ml) was treated with dibenzyl N. N-diisopropylphosphoramidite (1.72 ml, 5.11 mmol) for 22 h, oxidized with peracetic acid, and worked up as described. Purification by preparative HPLC (94% MeOH; 40 ml/min; $t_R$=22.40 min) gave compound rac-102 (297 mg, 50%) as an oil. $^1$H NMR ($CDCl_3$, 360 MHZ); δ 0.78 (3H, t, J=7.38 Hz, $CH_3$), 1.21–1.52 (2H, m, β-$CH_2$), 2.06–2.20 (2 H, m, α-$CH_2$), 3.41 (1H, ddd, J,=10.01, 2.03, 2.03 Hz, H-3), 4.28–4.34 (2 H, m, H-1, H-5), 4.49 (1 H, ddd, J,=9.41, 9.41, 9.41 Hz, H-4), 4.78–5.18 (18 H, m, $CH_2$Ph), 5.50 (1 H, ddd, J,=9.15, 2.03, 2.03 Hz, H-2), 5.64 (1H, dd, J,=10.14, 10.14 Hz, H-6), 7.07–7.32 (45 H, m, $CH_2$Ph). $^{31}$P NMR ($CDCL_3$, $^1$H decoupled, 145.8 MHZ); δ-1.94 (1 P, s),-1.03 (1 P, s), -0.79 (1 P, s), -0.32 (1 P, s). MS: m/z (+ve ion FAB) 1381 [(M+H)$^+$, 1], 71 [Bt$^+$, 100]. MS; m/z (–ve ion FAB) 1279 [(M–Bn$^+$)$^-$, 16], 277 [OPO (OBn)$^-_2$, 100].

rac-6-O-butyryl-myo-inositol 2, 3, 4, 5-tetrakisphosphate (rac-103). Compound rac-102 (290 mg, 210 μmol) was hydrogenated with palladium (10%) on carbon as described in the general procedure to give title compound rac-103 (119 mg, 99%) as a solid after freeze drying. $^1$H NMR ($D_2O$, 360 MHZ): δ 0.87(3 H, t, J=7.38 Hz, $CH_3$), 1.51–1.61 (2 H, m, β-$CH_2$), 2.39 (2 H, d, J=7.52 Hz, α-$CH_2$) 2.96 (1 H, ddd, J,=9.36, 7.45, 2.03 Hz, H-1), 3.88 (1 H, ddd, J=9.51, 2.03, 2.03 Hz, H-3), 4.29 (1 H, ddd, J,=9.94, 9.51, 9.51 Hz, H-5), 4.30 (1 H, dddd, J=9.36, 9.36, 2.03, 2.03 Hz, H-2), 4.52 (1 H, ddd, J,=9.51, 9.51, 9.51 Hz, H-4), 5.22 (1H, dd, J=9.94, 9.94 Hz, H-6). $^{31}$P NMR ($D_2O$, $^1$H decoupled, 145.8 MHZ); δ 0.19 (2P, s), 0.42 (1 P, s), 0.89 (1 P, s). MS:m/z ($^+$ve ion FAB) 571 [(M+H)$^+$, 10], 71 [Bt$^+$, 100] MS: m/z (–ve ion FAB) 569 [M–H$^+$)$^-$, 35], 79 [OP(O)$^-_2$, 100].

rac-1-O-[1,2-dipalmitoyl-sn-glycerole]-6-O-butyryl-myo-inositol 3,4,5-trisphosphate hexakis(acetoxymethyl) ester (rac-104). DIEA (190 μl, 1.12 mmol) and acetoxymethyl bromide (126 μl, 1.26 mmol) were added to a suspension of compound rac-103 (40 mg, 70 μmol) in dry acetonitrile (1.5 ml). After stirring of the mixture at room temperature in the dark for 3 h, 1,2-dipalmitoyl-sn-glycerole (20 mg, 35 μmol) was added and the solution was stirred at 4° C. in the dark for 4 days. The solvent was evaporated under reduced pressure and the crude residue was extracted with toluene, to give the title compound rac-104 as a syrup.

rac-1-O-[1,2-dioctanoyl-sn-glycerole]-6-O-butyryl-myo-inositol. 3, 4, 5-trisphosphate hexakis (acetoxymethyl) ester (rac-105) DIEA (136 μl, 800 μmol) and acetoxymethyl bromide (90 μl, 900 μmol) were added to a suspension of compound rac-103 (28 mg, 50 μmol) in dry acetonitrile (1.5 ml.) After stirring of the mixture at room temperature in the dark for 3h, 1, 2-dipalmitoyl-sn-glycerole (23 mg, 70 μmol) was added and the solution was stirred at 4° C. in the dark for 4 days. The solvent was evaporated under reduced pressure and the crude residue was extracted with toluene, to give the title compound rac-105 as a syrup.

Materials—All chemical reagents were obtained in the highest purity available. Where necessary, solvents were dried and/or distilled before use. Acetonitrile was distilled from phosphorus(V) oxide and stored over molecular sieves 3 A, as was dimethylformamide (DMF). Pyridine and toluene were stored over molecular sieves 4 Å. Ethyldiisopropylamine (DIEA) was dried over sodium wire. Palladium on charcoal (10%) and trifluoroacetic acid were from Acros Chemie. Dibenzyl N,N-diisopropylphosphoramidite, peracetic acid (32% v/w), tetrazole and acetoxymethyl bromide were from Aldrich. Butyric anhydride, DIEA were from Merck. Benzyl bromide, cesium fluoride and 4-dimethylamino pyridine (DMAP) were from Fluka. All other reagents were from Riedel-de Haën. rac-3,4-Di-O-benzyl-1,2-cyclohexylidene-myo-inositol (1) was synthesized in the 3 steps from myo-inositol as described previously (Angyal et al., *J. Chem. Soc.* 4116 (1961); Jiang and Baker *Carbohydr. Chem.* 5:615 (1986)), each of which is incorporated herein by reference. All compounds were racemic.

3.4-Di-O-benzyl-5,6-di-O-butyryl-1.2-cyclohexylidene-myo-inositol (152)—A solution of 151 (130 mg, 295 μmol), butyric anhydride (193 μl, 1.18 mmol) and DMAP (40 mg, 33 μmol) in dry pyridine (2 ml) was stirred at room temperature for 2 days. The solvents were evaporated under high vacuum to give an oil. Residual pyridine was removed by evaporating three times with octane. The residue was dissolved in tert-butyl methyl ether (10 ml) and was washed once with phosphate buffer (10 ml), once with sodium hydrogen carbonate (10 ml), once with sodium hydrogen sulfate (10 ml), once again with phosphate buffer (10 ml) and then with brine (10 ml). The organic layer was dried over $Na_2SO_4$ and filtered. Evaporation of the solvent gave pure 152 (171 mg, 98%) as an oil. $^1$H NMR ($CHCl_3$, 360 MHz): δ 0.87 (3 H, t, J=7.30 Hz, $CH_3$), 0.91 (3 H, t, J=7.30 Hz, $CH_3$), 1.26–1.87 (14 H, m, $CH_2$ (cyclohex.), 2×β-$CH_2$ (Bt)), 2.12–2.17 (2 H, m, α-$CH_2$), 2.22–2.31 (2 H, m, α-$CH_2$), 3.76 (1H, dd, J=9.29, 4.05 Hz, H-3), 3.97 (1 H, dd, J=9.29, 8.85 Hz, H-4), 4.01 (1 H, dd, J=7.74, 5.09 Hz, H-1), 4.27 (1 H, dd, J=5.09, 4.05 Hz, H-2), 4.65–4.99 (4 H, m, 2×$CH_2$Ph), 4.96 (1 H, dd, J=10.51, 8.85 Hz, H-5), 5.29 (1 H, dd, J=10.51, 7.74 Hz, H-6), 7.26–7.38 (10 H, m, CH$_2$Ph). MS: m/z (+ve ion FAB) 581 [(M+H)$^+$, 1], 91 [Bn$^+$, 100]. MS: m/z 581.311 (M+H)$^+$ (calcd for C$_{34}$H$_{45}$O$_8$ 581.311).

3.4-Di-O-benzyl-5.6-di-O-butyryl-myo-inositol (153)—A solution of 152 (166 mg, 286 μmol) in 5 ml CH$_3$CN/H$_2$O (100:1) was stirred with trifluoroacetic acid (2 ml) at room temperature for 2 h. The reaction mixture was evaporated under diminished pressure and the product was extracted with tert.-butyl methyl ether. The organic layer was washed with brine, dried over Na$_2$SO$_4$, filtered and evaporated to give 153 as an oil (140 mg, 99%). $^1$H NMR (CHCl$_3$, 360 MHz): δ 0.88 (3 H, t, J=7.40 Hz, CH$_3$), 0.92 (3 H, t, J=7.40 Hz, CH$_3$), 1.50–1.66 (4 H, m, 2×β-CH$_2$), 2.11–2.13 (2 H, m, α-CH$_2$), 2.21–2.36 (2 H, m, α-CH$_2$), 3.05 (2 H, s (br), 2×OH), 3.54 (1H, dd, J=9.48, 2.77 Hz, H-3), 3.58 (1 H, dd, J=9.86, 2.77 Hz, H-1), 3.95 (1 H, dd, J=9.71, 9.48 Hz, H-4), 4.17 (1 H, dd, J=2.77, 2.77 Hz, H-2), 4.62–4.87 (4 H, m, 2×CH$_2$Ph), 5.01 (1 H, dd, J=9.71, 9.71 Hz, H-5), 5.29 (1 H, dd, J=9.86, 9.71 Hz, H-6), 7.23–7.34 (10 H, m, CH$_2$Ph). MS: m/z (+ve ion FAB) 523 [(M+Na)$^+$, 22], 91 [Bn$^+$, 100]. MS: m/z (−ve ion FAB) 499 [(M+H$^+$)$^-$, 2], 87 [Bt$^-$, 100]. MS: m/z 539.207 (M+K)$^+$ (calcd for C$_{28}$H$_{36}$O$_8$K 539.205).

1,3,4-Tri-O-benzyl-5.6-di-O-butyryl-myo-inositol (154)—Dry 153 (143 mg, 286 μmol) and dry dibutyltin oxide (71 mg, 300 μmol) were heated under reflux in dry toluene (100 ml) in a Soxhlet apparatus with activated molecular sieve (3 Å) for 4 h. The reaction mixture was cooled to room temperature and evaporated to dryness under diminished pressure. CsF (92 mg, 572 μmol) was added to the residual oil, and the mixture was kept under high vacuum for 2 h. The residual syrup was dissolved in dry DMF (5 ml) under argon and benzyl bromide (270 μl, 2.28 mmol) was added. After stirring the solution for 18 h, HPLC (Merck Hibar steel tube (250 mm×4 mm) filled with RP 18 material (Merck, Lichrosorb; 10 μm)) analysis (95% MeOH; 1.5 ml/min; t$_R$=3.20 min) showed no further reaction. Excess of benzyl bromide and DMF were removed in high vacuum. The crude product was chromatographed by preparative HPLC (Merck Prepbar steel column (250 mm×50 mm) filled with RP 18 material (Merck, LiChrospher; 10 μm)) (88% MeOH; 40 ml/min; t$_R$=17.20 min) to give compound 154 (448 mg, 75%) as a solid. $^1$H NMR (CHCl$_3$, 360 MHz): δ 0.87 (3 H, t, J=7.46 Hz, CH$_3$), 0.90 (3 H, t, J=7.25 Hz, CH$_3$), 1.48–1.68 (4 H, m, 2×β-CH$_2$), 2.09–2.22 (4 H, m, 2×α-CH$_2$), 2.52 (1 H, s (br), OH), 3.40 (1H, dd, J=9.99, 2.63 Hz, H-1), 3.44 (1 H, dd, J=9.66, 2.63 Hz, H-3), 4.03 (1 H, dd, J=9.88, 9.66 Hz, H-4), 4.19 (1 H, dd, J=2.63, 2.63 Hz, H-2), 4.51–4.88 (6 H, m, 3×CH$_2$Ph), 5.04 (1 H, dd, J=10.09, 9.88 Hz, H-5), 5.48 (1 H, dd, J=10.09, 9.99 Hz, H-6), 7.23–7.34 (15 H, m, CH$_2$Ph). MS: m/z (+ve ion FAB) 613 [(M+Na)$^+$, 6], 91 [Bn$^+$, 100]. MS: m/z 613.277 (M+Na)$^+$ (calcd for C$_{35}$H$_{42}$O$_8$Na 613.278).

1,3,4-Tri-O-benzyl-2,5,6-tri-O-butyryl-myo-inositol (155)—A solution of 154 (98 mg, 166 μmol), butyric anhydride (68 μl, 415 μmol) and DMAP (5 mg, 4 μmol) in dry pyridine (2 ml) was stirred at room temperature for 2 h. A similar work-up as described above for compound 2 gave pure 155 (106 mg, 99%) as an oil. $^1$H NMR (CHCl$_3$, 360 MHz): δ 0.87 (3 H, t, J=7.47 Hz, CH$_3$), 0.89 (3 H, t, J=7.96 Hz, CH$_3$), 0.96 (3 H, t, J=7.47 Hz, CH$_3$), 1.23–1.41 (2 H, m, CH$_2$), 1.51–1.60 (2 H, m, CH$_2$), 1.65–1.73 (2 H, m, CH$_2$), 2.13 (2 H, t, J=7.47 Hz, α-CH$_2$), 2.20 (2 H, t, J=7.47 Hz, α-CH$_2$), 2.43 (2 H, t, J=7.47 Hz, α-CH$_2$), 3.46 (1H, dd, J=10.03, 2.77 Hz, H-1), 3.53 (1 H, dd, J=9.82, 2.99 Hz, H-3), 3.86 (1 H, dd, J=9.82, 9.82 Hz, H-4), 4.40–4.83 (6 H, m, 3×CH$_2$Ph), 5.06 (1 H, dd, J=10.03, 9.82 Hz, H-5), 5.37 (1 H, dd, J=10.03, 10.03 Hz, H-6), 5.86 (1 H, dd, J=2.99, 2.77 Hz, H-2), 7.19–7.34 (15 H, m, CH$_2$Ph). MS: m/z (+ve ion FAB) 661 [(M+H)$^+$, 1], 91 [Bn$^+$, 100]. MS: m/z 661.338 (M+H)$^+$ (calcd for C$_{29}$H$_{49}$O$_9$ 661.334).

2,5,6-Tri-O-butyryl-myo-inositol (156)—155 (105 mg, 159 μmol) was dissolved in acetic acid (3ml), before palladium (10%) on charcoal (80 mg, 795 μmol) was added. After stirring the solution at room temperature for 6 h under hydrogen atmosphere the catalyst was removed by ultrafiltration and the filtrate was freeze dried to give title compound 156 (53 mg, 86%). Mp: 113.4°–114.4° C. (from MeOH). $^1$H NMR ([D]$_6$-DMSO): δ 0.94 (3 H, t, J=7.53 Hz, CH$_3$), 0.95 (3 H, t, J=7.53 Hz, CH$_3$), 0.99 (3 H, t, J=7.53 Hz, CH$_3$), 1.59–1.76 (6 H, m, 3×β-CH$_2$), 2.25–2.36 (4 H, m, 2×α-CH$_2$), 2.43 (2 H, t, J=7.32 Hz, α-CH$_2$), 3.72 (1H, dd, J=9.77, 2.84 Hz, H-3), 3.83 (1 H, dd, J=10.17, 2.84 Hz, H-1), 3.85 (1 H, dd, J=9.77, 9.77 Hz, H-4), 5.02 (1 H, dd, J=9.77, 9.77 Hz, H-5), 5.25 (1 H, dd, J=10.17, 9.77 Hz, H-6), 5.53 (1 H, dd, J=2.84, 2.84 Hz, H-2), MS: m/z (+ve ion FAB) 391 [(M+H)$^+$, 5], 71 [Bt$^+$, 100]. MS: m/z (−ve ion FAB) 389 [(M−H$^+$)$^-$, 11], 87 [BtO$^-$, 100]. Anal. Calcd for C$_{18}$H$_{30}$O$_9$: C, 55.37; H, 7.74. Found: C, 55.43; H, 7.84.

2,5,6-Tri-O-butyryl-myo-inositol 1,3,4-tris(dibenzyl) phosphate (157)—A solution of triol 156 (48 mg, 123 μmol) and tetrazole (104 mg, 1.48 mmol) in acetonitrile (2 ml) was treated with dibenzyl N,N-diisopropylphosphoramidite (500 μl, 1.48 mmol) for 18 h, cooled to −40° C. and oxidized with peracetic acid (32% v/w, 340 μl, 1.48 mmol) under vigorous stirring (Yu and Fraiser-Reid, *Tetrahedron Lett.* 29:979 (1988)), which is incorporated herein by reference. The mixture was allowed to warm to room temperature. The solvent was removed under reduced pressure and the residual oil was purified by preparative HPLC (92% MeOH; 40 ml/min; t$_R$=17.50 min) to give compound 157 (104 mg, 72%) as an oil. $^1$H NMR (CHCl$_3$, 360 MHz): δ 0.76 (3 H, t, J=7.32 Hz, CH$_3$), 0.78 (3 H, t, J=7.32 Hz, CH$_3$), 0.93 (3 H, t, J=7.32 Hz, CH$_3$), 1.32–1.50 (4 H, m, 2×β-CH$_2$), 1.57–1.67 (2 H, m, β-CH$_2$), 2.04 (2 H, t, J=7.57 Hz, α-CH$_2$), 2.13 (2 H, t, J=7.57 Hz, α-CH$_2$), 2.35 (2 H, t, J=7.57 Hz, α-CH$_2$), 4.38 (1 H, ddd, J=9.28, 9.28, 2.69 Hz, H-3), 4.47 (1H, ddd, J=9.99, 9.99, 2.69 Hz, H-1), 4.82–5.04 (13 H, m, 3×CH$_2$Ph, H-4), 5.14 (1 H, dd, J=9.77, 9.77 Hz, H-5), 5.45 (1 H, dd, J=9.99, 9.77 Hz, H-6), 6.04 (1 H, dd, J=2.69, 2.69 Hz, H-2), 7.20–7.34 (30 H, m, CH$_2$Ph). $^{31}$P-NMR (CHCl$_3$, $^1$H-decoupled, 145.8 MHz): δ−1.25 (1 P, s), −1.18 (1 P, s), −1.15 (1 P, s). MS: m/z (+ve ion FAB) 1171 [(M+H)$^+$, 4], 91 [Bn$^+$, 100]. MS: m/z (−ve ion FAB) 1079 [(M−Bn$^+$)$^-$, 45], 277 [OPO(OBn)$_2^-$, 100].

2,5,6-Tri-O-butyryl-myo-inositol 1,3,4-trisphosphate (158)—The free acid 157 (100 mg, 85 μmol) was hydrogenated as described above to give title compound 158 (47 mg, 88%) after freeze drying. $^1$H NMR (D$_2$O, 360 MHz): δ 0.83 (3 H, t, J=7.40 Hz, CH$_3$), 0.84 (3 H, t, J=7.40 Hz, CH$_3$), 0.92 (3 H, t, J=7.40 Hz, CH$_3$), 1.46–1.56 (4 H, m, 2×β-CH$_2$), 1.61–1.71 (2 H, m, β-CH$_2$), 2.32 (2 H, t, J=7.22 Hz, α-CH$_2$), 2.34 (2 H, t, J=7.22 Hz, α-CH$_2$), 2.47 (2 H, t, J=7.22 Hz, α-CH$_2$), 4.44–4.55 (2H, m, H-1, H-3), 4.61 (1 H, ddd, J=9.57, 9.39, 9.39 Hz, H-4), 5.26 (1 H, dd, J=9.57, 9.57 Hz, H-5), 5.35 (1 H, dd, J=9.75, 9.57 Hz, H-6), 5.77 (1 H, s (br), H-2). $^{31}$P-NMR (D$_2$O, $^1$H-decoupled, 145.8 MHz): δ−0.94 (1 P, s), −0.09 (1 P, s), −0.06 (1 P, s). MS: m/z (+ve ion FAB) 669 [(M+K)$^+$, 20], 71 [Bt$^+$, 100]. MS: m/z (−ve ion FAB) 629 [(M−H$^+$)$^-$, 30], 97 [OP(OH)$_2^-$, 100].

2,5,6-Tri-O-butyryl-myo-inositol 1,3,4-trisphosphate hexakis(acetoxymethyl) ester (159)—DIEA (209 μl, 1.23 mmol) and acetoxymethyl bromide (123 μl, 1.23 mmol) were added to a suspension of compound 158 (39 mg, 61

μmol) in dry acetonitrile (2 ml). After stirring of the mixture at room temperature in the dark for 4 days all volatile components were evaporated off under reduced pressure and the crude residue was purified by preparative HPLC (73% MeOH, 40 ml/min, $t_R$=20.25) to give compound 159 (44 mg, 67%) as a syrup. $^1$H NMR ([D]$_8$toluene, 360 MHz): δ 0.83 (3 H, t, J=7.28 Hz, CH$_3$), 0.92 (3 H, t, J=7.28 Hz, CH$_3$), 0.97 (3 H, t, J=7.48 Hz, CH$_3$), 1.50–1.60 (2 H, m, β-CH$_2$), 1.67–1.76 (4 H, m, 2×β-CH$_2$), 1.79–1.96 (18 H, 6∃3 s, 6×OAc), 2.08–2.13 (2 H, m, α-CH$_2$), 2.33–2.47 (2 H, m, α-CH$_2$), 2.52–2.61 (2 H, m, α-CH$_2$), 5.05 (1H, ddd, J=9.64, 9.64, 2.17 Hz, H-3), 5.09 (1 H, ddd, J=9.64, 9.06, 9.06 Hz, H-4), 5.11 (1 H, ddd, J=9.84, 9.84, 2.17 Hz, H-1), 5.50–5.83 (14 H, m, 6×CH$_2$OAc, H-5, H-6), 6.21 (1 H, dd, J=2.17, 2.17 Hz, H-2). $^{31}$P-NMR (D$_2$O, $^1$H-decoupled, 145.8 MHz): δ−4.17 (1 P, s), −4.05 (1 P, s), −3.97 (1 P, s). MS: m/z (+ve ion FAB) [(M+K)$^+$, 20], 71 [Bt$^+$, 100]. MS: m/z (−ve ion FAB) [(M−H$^+$)$^−$, 30], 97 [, 100].

Although the invention has been described with reference to the examples provided above, it should be understood that various modifications can be made without departing from the spirit of the invention. Accordingly, the invention is limited only by the claims.

We claim:

1. A cell permeable agonist of an inositol polyphosphate, comprising an inositol polyphosphate derivative or a mimic thereof.

2. The cell permeable agonist of claim 1, wherein said inositol polyphosphate is myo-inositol 3,4,5,6-tetrakisphosphate.

3. The cell permeable agonist of claim 2, wherein said cell permeable agonist is a derivative of myo-inositol 3,4,5,6-tetrakisphosphate.

4. The derivative of claim 3, wherein said derivative is D,L-1-O-butyryl-2-O-deoxy-inositol 3,4,5,6-tetrakisphosphate octakis (acetoxymethyl) ester.

5. The cell permeable agonist of claim 2, wherein said cell permeable agonist is a derivative of myo-inositol 1,3,4-trisphosphate.

6. The derivative of claim 5, wherein said derivative is D,L-2,5,6-tri-O-acyl-myo-inositol 1,3,4-trisphosphate hexakis(acetoxymethyl)ester.

7. The derivative of claim 6, wherein said derivative is D,L-2,5,6-tri-O-butyryl-myo-inositol 1,3,4-trisphosphate hexakis(acetoxymethyl)ester.

8. The cell permeable agonist of claim 1, wherein said inositol polyphosphate is phosphatidylinositol 3,4,5-trisphosphate.

9. The cell permeable agonist of claim 8, wherein said cell permeable agonist is a derivative of phosphatidylinositol 3,4,5-trisphosphate.

10. The derivative of claim 9, wherein said derivative is di-palmitoyl-D,L-O-acyl-phosphatidylinositol 3,4,5-trisphosphate heptakis(acetoxymethyl)ester.

11. The derivative of claim 10, wherein said derivative is sn-di-O-palmitoyl-D,L-6-O-butyryl-phosphatidylinositol 3,4,5-trisphosphate heptakis(acetoxymethyl)ester.

12. The derivative of claim 9, wherein said derivative is sn-di-O-octanoyl-D,L-6-O-butyryl-phosphatidylinositol 3,4,5-trisphosphate heptakis(acetoxymethyl)ester.

13. A method for decreasing chloride ion secretion from a cell, comprising contacting the cell with the cell permeable agonist of claim 1.

14. The method of claim 13, wherein said inositol polyphosphate is myo-inositol 3,4,5,6-tetrakisphosphate.

15. The method of claim 14, wherein said cell permeable agonist is a derivative of myo-inositol 3,4,5,6-tetrakisphosphate.

16. The method of claim 15, wherein said derivative is 1,2-di-O-acyl-myo-inositol 3,4,5,6-tetrakisphosphate octakis(acetoxymethyl)ester.

17. The method of claim 16, wherein said derivative is 1,2-di-O-butyryl-myo-inositol 3,4,5,6-tetrakisphosphate octakis(acetoxymethyl)ester.

18. The method of claim 16, wherein said derivative is 1,2-di-O-butyryl-scyllo-inositol 3,4,5,6-tetrakisphosphate octakis(acetoxymethyl)ester.

19. The method of claim 15, wherein said derivative is D,L-1-O-butyryl-2-O-deoxy-inositol 3,4,5,6-tetrakisphosphate octakis (acetoxymethyl) ester.

20. The method of claim 14, wherein said cell permeable agonist is a derivative of myo-inositol 1,3,4-trisphosphate.

21. The method of claim 20, wherein said derivative is D,L-2,5,6-tri-O-acyl-myo-inositol 1,3,4-trisphosphate hexakis(acetoxymethyl)ester.

22. The method of claim 21, wherein said derivative is D,L-2,5,6-tri-O-butyryl-myo-inositol 1,3,4-trisphosphate hexakis(acetoxymethyl)ester.

23. The method of claim 13, wherein said inositol polyphosphate is phosphatidylinositol 3,4,5-trisphosphate.

24. The method of claim 23, wherein said cell permeable agonist is a derivative of phosphatidylinositol 3,4,5-trisphosphate.

25. The method of claim 24, wherein said derivative is di-palmitoyl-D,L-O-acyl-phosphatidylinositol 3,4,5-trisphosphate heptakis(acetoxymethyl)ester.

26. The method of claim 25, wherein said derivative is sn-di-O-palmitoyl-D,L-6-O-butyryl-phosphatidylinositol 3,4,5-trisphosphate heptakis(acetoxymethyl)ester.

27. The method of claim 24, wherein said derivative is sn-di-O-octanoyl-D,L-6-O-butyryl-phosphatidylinositol 3,4,5-trisphosphate heptakis(acetoxymethyl)ester.

28. A method for decreasing chloride ion secretion in an individual, comprising administering to the individual the cell permeable agonist of claim 1.

29. The method of claim 28, wherein said inositol polyphosphate is myo-inositol 3,4,5,6-tetrakisphosphate.

30. The method of claim 29, wherein said cell permeable agonist is a derivative of myo-inositol 3,4,5,6-tetrakisphosphate.

31. The method of claim 30, wherein said derivative is 1,2-di-O-acyl-myo-inositol 3,4,5,6-tetrakisphosphate octakis(acetoxymethyl)ester.

32. The method of claim 31, wherein said derivative is 1,2-di-O-butyryl-myo-inositol 3,4,5,6-tetrakisphosphate octakis(acetoxymethyl)ester.

33. The method of claim 31, wherein said derivative is 1,2-di-O-butyryl-scyllo-inositol 3,4,5,6-tetrakisphosphate octakis(acetoxymethyl)ester.

34. The method of claim 30, wherein said derivative is D,L-1-O-butyryl-2-O-deoxy-inositol 3,4,5,6-tetrakisphosphate octakis (acetoxymethyl) ester.

35. The method of claim 29, wherein said cell permeable agonist is a derivative of myo-inositol 1,3,4-trisphosphate.

36. The method of claim 35, wherein said derivative is D,L-2,5,6-tri-O-acyl-myo-inositol 1,3,4-trisphosphate hexakis(acetoxymethyl)ester.

37. The method of claim 36, wherein said derivative is D,L-2,5,6-tri-O-butyryl-myo-inositol 1,3,4-trisphosphate hexakis(acetoxymethyl)ester.

38. The method of claim 28, wherein said inositol polyphosphate is phosphatidylinositol 3,4,5-trisphosphate.

39. The method of claim 38, wherein said cell permeable agonist is a derivative of phosphatidylinositol 3,4,5-trisphosphate.

40. The method of claim 39, wherein said derivative is di-palmitoyl-D,L-O-acyl-phosphatidylinositol 3,4,5-trisphosphate heptakis(acetoxymethyl)ester.

41. The method of claim 40, wherein said derivative is sn-di-O-palmitoyl-D,L-6-O-butyryl-phosphatidylinositol 3,4,5-trisphosphate heptakis(acetoxymethyl)ester.

42. The method of claim 39, wherein said derivative is sn-di-O-octanoyl-D,L-6-O-butyryl-phosphatidylinositol 3,4,5-trisphosphate heptakis(acetoxymethyl)ester.

43. A method for alleviating a sign or symptom associated with secretory diarrhea in an individual, comprising administering the cell permeable agonist of claim 1 to the individual.

44. The method of claim 43, wherein said inositol polyphosphate is myo-inositol 3,4,5,6-tetrakisphosphate.

45. The method of claim 44, wherein said cell permeable agonist is a derivative of myo-inositol 3,4,5,6-tetrakisphosphate.

46. The method of claim 45, wherein said derivative is 1,2-di-O-acyl-myo-inositol 3,4,5,6-tetrakisphosphate octakis(acetoxymethyl)ester.

47. The method of claim 46, wherein said derivative is 1,2-di-O-butyryl-myo-inositol 3,4,5,6-tetrakisphosphate octakis(acetoxymethyl)ester.

48. The method of claim 46, wherein said derivative is 1,2-di-O-butyryl-scyllo-inositol 3,4,5,6-tetrakisphosphate octakis(acetoxymethyl)ester.

49. The method of claim 45, wherein said derivative is D,L-1-O-butyryl-2-O-deoxy-inositol 3,4,5,6-tetrakisphosphate octakis(acetoxymethyl) ester.

50. The method of claim 44, wherein said agonist is a derivative of myo-inositol 1,3,4-trisphosphate.

51. The method of claim 50, wherein said derivative is D,L-2,5,6-tri-O-acyl-myo-inositol 1,3,4-trisphosphate hexakis(acetoxymethyl)ester.

52. The method of claim 51, wherein said derivative is D,L-2,5,6-tri-O-butyryl-myo-inositol 1,3,4-trisphosphate hexakis(acetoxymethyl)ester.

53. The method of claim 43, wherein said inositol polyphosphate is phosphatidylinositol 3,4,5-trisphosphate.

54. The method of claim 53, wherein said cell permeable agonist is a derivative of phosphatidylinositol 3,4,5-trisphosphate.

55. The method of claim 54, wherein said derivative is di-palmitoyl-D,L-O-acyl-phosphatidylinositol 3,4,5-trisphosphate heptakis(acetoxymethyl)ester.

56. The method of claim 55, wherein said derivative is sn-di-O-palmitoyl-D,L-6-O-butyryl-phosphatidylinositol 3,4,5-trisphosphate heptakis(acetoxymethyl)ester.

57. The method of claim 54, wherein said derivative is sn-di-O-octanoyl-D,L-6-O-butyryl-phosphatidylinositol 3,4,5-trisphosphate heptakis(acetoxymethyl)ester.

58. A method for alleviating a sign or symptom associated with brain swelling in an individual, comprising administering the cell permeable agonist of claim 1 to the individual.

59. The method of claim 58, wherein said inositol polyphosphate is myo-inositol 3,4,5,6-tetrakisphosphate.

60. The method of claim 59, wherein said cell permeable agonist is a derivative of myo-inositol 3,4,5,6-tetrakisphosphate.

61. The method of claim 60, wherein said derivative is 1,2-di-O-acyl-myo-inositol 3,4,5,6-tetrakisphosphate octakis(acetoxymethyl)ester.

62. The method of claim 61, wherein said derivative is 1,2-di-O-butyryl-myo-inositol 3,4,5,6-tetrakisphosphate octakis(acetoxymethyl)ester.

63. The method of claim 61, wherein said derivative is 1,2-di-O-butyryl-scyllo-inositol 3,4,5,6-tetrakisphosphate octakis(acetoxymethyl)ester.

64. The method of claim 60, wherein said derivative is D,L-1-O-butyryl-2-O-deoxy-inositol 3,4,5,6-tetrakisphosphate octakis(acetoxymethyl) ester.

65. The method of claim 59, wherein said cell permeable agonist is a derivative of myo-inositol 1,3,4-trisphosphate.

66. The method of claim 65, wherein said derivative is D,L-2,5,6-tri-O-acyl-myo-inositol 1,3,4-trisphosphate hexakis(acetoxymethyl)ester.

67. The method of claim 66, wherein said derivative is D,L-2,5,6-tri-O-butyryl-myo-inositol 1,3,4-trisphosphate hexakis(acetoxymethyl)ester.

68. The method of claim 58, wherein said inositol polyphosphate is phosphatidylinositol 3,4,5-trisphosphate.

69. The method of claim 68, wherein said agonist is a derivative of phosphatidylinositol 3,4,5-trisphosphate.

70. The method of claim 69, wherein said derivative is di-palmitoyl-D,L-O-acyl-phosphatidylinositol 3,4,5-trisphosphate heptakis(acetoxymethyl)ester.

71. The method of claim 70, wherein said derivative is sn-di-O-palmitoyl-D,L-6-O-butyryl-phosphatidylinositol 3,4,5-trisphosphate heptakis(acetoxymethyl)ester.

72. The method of claim 69, wherein said derivative is sn-di-O-octanoyl-D,L-6-O-butyryl-phosphatidylinositol 3,4,5-trisphosphate heptakis(acetoxymethyl)ester.

* * * * *